(12) United States Patent
Sasada et al.

(10) Patent No.: US 8,480,926 B2
(45) Date of Patent: Jul. 9, 2013

(54) LIQUID-CRYSTALLINE COMPOUND AND ORGANIC SEMICONDUCTOR DEVICE CONTAINING THE COMPOUND

(75) Inventors: Yasuyuki Sasada, Chiba (JP); Tetsuharu Miwa, Chiba (JP)

(73) Assignee: JNC Corporation, Tokyo (JP)

( * ) Notice: Subject to any disclaimer, the term of this patent is extended or adjusted under 35 U.S.C. 154(b) by 71 days.

(21) Appl. No.: 13/175,940

(22) Filed: Jul. 4, 2011

(65) Prior Publication Data
US 2012/0007062 A1    Jan. 12, 2012

(30) Foreign Application Priority Data

Jul. 6, 2010 (JP) ................ 2010-153722
Jun. 30, 2011 (JP) ................ 2011-145505

(51) Int. Cl.
C09K 19/34 (2006.01)
C07D 285/12 (2006.01)
C07D 285/14 (2006.01)
H01L 51/00 (2006.01)
H01L 21/337 (2006.01)

(52) U.S. Cl.
USPC ........ 252/299.61; 548/136; 548/142; 257/40; 257/E51.006; 257/E51.025; 438/30; 438/142; 438/188

(58) Field of Classification Search
USPC ........ 548/134, 136, 142; 252/299.61; 438/30, 438/142, 188; 257/40, E51.006, E51.025
See application file for complete search history.

(56) References Cited

FOREIGN PATENT DOCUMENTS

| JP | 2003096457 A | * | 4/2003 |
| JP | 2009-137848 | | 6/2009 |
| JP | 2009-242339 | | 10/2009 |
| JP | 2010-003831 | | 1/2010 |

OTHER PUBLICATIONS

Liao et al., "An unprecedented ambipolar charge transport material exhibiting balanced electron and hole mobilities", The Royal Society of Chemistry, Chem. Commun., Feb. 9, 2007, pp. 1831-1833, Issue 18.

* cited by examiner

Primary Examiner — Shean C Wu
(74) Attorney, Agent, or Firm — Jianq Chyun IP Office

(57) ABSTRACT

Disclosed is a visible light-transmissive liquid-crystalline compound having good hole and electron-transport characteristics and useful as an organic semiconductor material. The compound is represented by a formula (1):

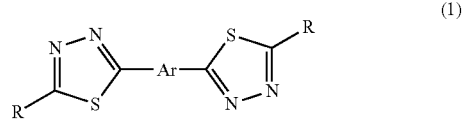

(1)

wherein R independently represents hydrogen, or alkyl having from 1 to 24 carbon atoms, and any —$CH_2$— in the alkyl may be replaced by —O—, —S—, —CO— or —$SiH_2$—, any —$(CH_2)_2$— may be replaced by —CH=CH— or —C≡C—, and any hydrogen may be replaced by halogen; Ar represents naphthylene, anthrylene, phenanthrylene, or phenylene; and every hydrogen in phenylene is replaced by halogen, and any hydrogen in naphthylene, anthrylene and phenanthrylene may be replaced by halogen.

18 Claims, 1 Drawing Sheet

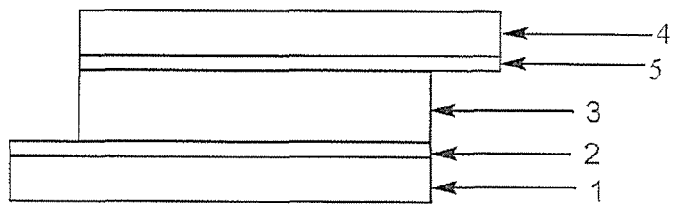

LIQUID-CRYSTALLINE COMPOUND AND ORGANIC SEMICONDUCTOR DEVICE CONTAINING THE COMPOUND

CROSS-REFERENCE TO RELATED APPLICATION

This application claims the priority benefit of Japan application no. 2010-153722, filed on Jul. 6, 2010, and Japan application no. 2011-145505, filed on Jun. 30, 2011. The entirety of each of the above-mentioned patent applications is hereby incorporated by reference herein and made a part of this specification.

BACKGROUND OF THE INVENTION

1. Field of the Invention

The present invention relates to a novel liquid-crystalline compound and to an organic semiconductor film and an organic semiconductor device containing the compound.

The present invention relates to a compound with a thiadiazole group introduced into both ends of the aromatic ring therein, and to an organic semiconductor film and an organic semiconductor device containing the compound.

2. Background Art

Recently, thin-film devices such as typically OFET (organic field-effect transistor) devices using an organic semiconductor material have become specifically noted.

In particular, forming an integrated circuit with an organic semiconductor, if possible, could make it possible to form the integrated circuit inexpensively, as compared with the existing production process of forming integrated circuits using silicon.

In integrated circuits generally used at present, employed is a configuration called CMOS (complementary metal oxide semiconductor). In this configuration, the gate electrode of the n-channel transistor and the gate electrode of the p-channel transistor are connected to each other and the drain electrode of the n-channel transistor and the drain electrode of the p-channel transistor are connected to each other. The configuration is characterized by strong resistance to noise and low power consumption.

CMOS requires both the p-type semiconductor that assumes the role of hole transport and the n-type semiconductor that assumes the role of electron transport. When one compound could assume the two roles, then the production process could be thereby simplified. Examples of the compound of the type are described, for example, in Patent Reference 1.

In order to attain suitable carrier transport characteristics of an organic semiconductor, an important matter is configuration control of organic semiconductor molecules. One method of configuration control thereof comprises controlling the configuration of organic semiconductor molecules via a liquid-crystal phase not having a crystal-analogous layer structure or columnar structure. In fact, there are seen many publications relating to organic semiconductors having a liquid-crystal phase (for example, Patent Reference 2).

There are known some compounds, each one of which has a liquid-crystal phase and has both a hole-transport capability and an electron-transport capability by itself (for example, Patent Reference 3).

However, the compounds described in the above-mentioned Patent References 1 to 3 have absorption in the visible region. Accordingly, in some cases, they may be often unfavorable for use in transistors for display devices to be used under visible light.

There are known some compounds that does not absorb visible light and has both a hole-transport capability and an electron-transport capability by itself. But that compounds have low level electron mobility and hole mobility (for example, Nonpatent Reference 1).

CITATION LIST

Patent References

Patent Reference 1: JP 2009-242339 A
Patent Reference 2: JP 2009-137848 A
Patent Reference 3: JP 2010-003831 A

Nonpatent References

Nonpatent Reference 1: Yuan-Li Liao et al., Chem. Commun., 1831 (2007)

SUMMARY OF THE INVENTION

An object of the present invention is to provide a visible light-transmissive liquid-crystalline compound having suitable hole and electron-transport characteristics and useful as an organic semiconductor material.

Another object is to provide, using the liquid-crystalline compound, an organic semiconductor film, a semiconductor device and a transistor having suitable hole and electron-transport characteristics and having a low defect density.

The present inventors assiduously investigated the above-mentioned problems. As a result, the inventors have found that a rod-like compound with a thiadiazole group introduced into both ends of the aromatic ring therein can solve the problems, and have completed the present invention.

Concrete constitutive embodiments of the invention are shown below.

[1] A compound represented by a formula (1):

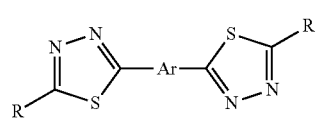

[In the formula (1),

R independently represents hydrogen, or alkyl having from 1 to 24 carbon atoms, and any —$CH_2$— in the alkyl may be replaced by —O—, —S—, —CO— or —$SiH_2$—, any —$(CH_2)_2$— may be replaced by —CH=CH— or —C≡C—, and any hydrogen may be replaced by halogen;

Ar represents naphthylene, anthrylene, phenanthrylene, or phenylene; and every hydrogen in phenylene is replaced by halogen, and any hydrogen in naphthylene, anthrylene and phenanthrylene may be replaced by halogen.]

[2] The compound described in [1], wherein in the formula (1), R is independently hydrogen, alkyl having from 1 to 20 carbon atoms, alkoxy having from 1 to 20 carbon atoms, alkenyl having from 2 to 20 carbon atoms, alkynyl having from 2 to 20 carbon atoms, alkoxyalkyl having from 2 to 20 carbon atoms, alkenyloxy having from 2 to 20 carbon atoms, thioalkyl having from 1 to 20 carbon atoms, alkylthioalkyl having from 2 to 20 carbon atoms, or thioalkenyl having from 2 to 20 carbon atoms, and any hydrogen in these groups may be replaced by fluorine.

[3] The compound described in [1] or [2], wherein in the formula (1), Ar is naphthylene, anthrylene, phenanthrylene, or phenylene; and every hydrogen in phenylene is replaced by chlorine or fluorine, and any hydrogen in naphthylene, anthrylene and phenanthrylene may be replaced by fluorine.

[4] The compound described in any of [1] to [3], which has an electron mobility and a hole mobility of from $1.0 \times 10^{-4}$ to $1.0 \times 10^{2}$ cm$^2$/Vs.

[5] A composition for organic semiconductor, which comprises a compound represented by a formula (2):

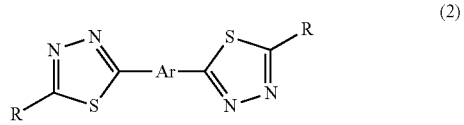

(2)

[In the formula (2),

R independently represents hydrogen, or alkyl having from 1 to 24 carbon atoms, and any —CH$_2$— in the alkyl may be replaced by —O—, —S—, —CO— or —SiH$_2$—, any —(CH$_2$)$_2$— may be replaced by —CH═CH— or —C≡—, and any hydrogen may be replaced by halogen;

Ar represents phenylene, naphthylene, anthrylene, or phenanthrylene, and any hydrogen in these rings may be replaced by halogen.]

[6] The composition for organic semiconductor described in [5], wherein in the formula (2), R is independently hydrogen, alkyl having from 1 to 20 carbon atoms, alkoxy having from 1 to 20 carbon atoms, alkenyl having from 2 to 20 carbon atoms, alkynyl having from 2 to 20 carbon atoms, alkoxyalkyl having from 2 to 20 carbon atoms, alkenyloxy having from 2 to 20 carbon atoms, thioalkyl having from 1 to 20 carbon atoms, alkylthioalkyl having from 2 to 20 carbon atoms, or thioalkenyl having from 2 to 20 carbon atoms, and any hydrogen in these groups may be replaced by fluorine.

[7] The composition for organic semiconductor described in [5] or [6], wherein in the formula (2), Ar is phenylene, naphthylene, anthrylene, or phenanthrylene, and any hydrogen in these rings may be replaced by fluorine.

[8] A liquid-crystal composition for organic semiconductor wherein the composition for organic semiconductor described in any of [5] to [7] has a smectic phase or a nematic phase.

[9] An organic semiconductor film formed of the compound described in any of [1] to [4], or the composition for organic semiconductor described in any of [5] to [7], or the liquid-crystal composition for organic semiconductor described in [8].

[10] An organic semiconductor device comprising an electrode and the organic semiconductor film described in [9].

[11] A field effect transistor comprising a gate electrode, a dielectric layer, a source electrode, a drain electrode and a semiconductor layer, wherein the semiconductor layer comprises the organic semiconductor film described in [9].

[12] A semiconductor device comprising an n-channel transistor (1) and a p-channel transistor (2), wherein the n-channel transistor (1) is the transistor described in [11], the p-channel transistor (2) is formed of an arbitrary material, the drain electrode of the n-channel transistor (1) and the drain electrode of the p-channel transistor (2) are connected to each other via a material having a transistor on-resistance of less than 10%, and the gate electrode of the n-channel transistor (1) and the gate electrode of the p-channel transistor (2) are connected to each other via a material having a transistor on-resistance of less than 10%.

[13] A semiconductor device comprising an n-channel transistor (3) and a p-channel transistor (4), wherein the n-channel transistor (3) is formed of an arbitrary material, the p-channel transistor (4) is the transistor described in [11], the drain electrode of the n-channel transistor (3) and the drain electrode of the p-channel transistor (4) are connected to each other via a material having a transistor on-resistance of less than 10%, and the gate electrode of the n-channel transistor (3) and the gate electrode of the p-channel transistor (4) are connected to each other via a material having a transistor on-resistance of less than 10%.

[14] A semiconductor device comprising an n-channel transistor (1) and a p-channel transistor (4), wherein the n-channel transistor (1) and the p-channel transistor (4) each are the transistor described in [11], the drain electrode of the n-channel transistor (1) and the drain electrode of the p-channel transistor (4) are connected to each other via a material having a transistor on-resistance of less than 10%, and the gate electrode of the n-channel transistor (1) and the gate electrode of the p-channel transistor (4) are connected to each other via a material having a transistor on-resistance of less than 10%.

The liquid-crystalline compound having a thiadiazole group at both ends of the aromatic ring therein of the invention has a suitable carrier mobility for both electron and hole and is excellent in compatibility with organic solvents and others, not having visible light absorption, and is therefore useful as an organic semiconductor material.

In addition, the organic semiconductor film, the semiconductor device and the transistor of the invention have suitable hole and electron-transport characteristics and have a low defect density.

BRIEF DESCRIPTION OF THE DRAWING

FIG. 1 is a schematic cross-sectional view of a test cell in a TOF method for determining the carrier mobility according to the TOF method.

In the drawing, 1 and 4 each are a glass substrate, 2 and 5 each are an ITO electrode, and 3 is a charge-transport material (compound (1) to compound (4)).

DESCRIPTION OF THE PREFERRED EMBODIMENTS

The compound and its use of the invention are described in detail hereinunder.

In the following, the compound represented by the above-mentioned formula (1) maybe referred to as "compound (1)", and "compound (1)" may mean at least one compound represented by the formula (1). The same may apply to other compounds represented by other formulae. In case where one compound represented by a chemical formula has multiple groups all represented by the same symbol, these groups may be the same or different.

"Any or arbitrary" as referred to herein means that not only the number but also the position is arbitrarily defined. In the invention, "any —CH$_2$—" means that not only the number but also the position thereof is arbitrarily defined, but it is unfavorable that continuing multiple —CH$_2$—'s are replaced by the same group. The substituent of which the position bonding to the carbon that constitutes a ring is not specifically defined means that the bonding position thereof is free within a range not causing any chemical problem.

In the invention, the compound having a liquid-crystal phase such as a smectic phase, a nematic phase or the like, and the compound not having a liquid-crystal phase but useful as an ingredient of a liquid-crystal composition may be generically referred to as "liquid-crystalline compound".

<<Compound (1)>>

The compound (1) is a liquid-crystalline compound with a thiadiazole group introduced into both ends of the aromatic ring therein, and is excellent in compatibility with organic solvents, etc.

The compound (1) is a liquid-crystalline compound, and therefore when a semiconductor film is formed of the compound (1) or of a composition containing the compound (1), then a semiconductor film having a reduced defect density can be obtained, and consequently the compound (1) is favorable for use as an organic semiconductor material.

The compound (1) has the property of not being in a molten state in an ordinary usage environment (e.g., at 0 to 100° C.) for organic semiconductor devices. Accordingly, the compound (1) is favorable for use as a material (organic semiconductor material) for organic semiconductor devices.

The compound (1) does not absorb visible light. Consequently, the compound (1) is favorable for use as a material for semiconductor devices to be used under visible light.

The compound (1) can transport electrons and holes. The reason may be considered because the molecular orbital change in the compound (1) in electron addition thereto or electron removal therefrom is not so large and the potential barrier in the compound (1) can be small.

The electron mobility and the hole mobility of the compound (1) each are preferably from $1.0 \times 10^{-4}$ to $1.0 \times 10^{2}$ cm$^2$/Vs, more preferably from $1.0 \times 10^{-3}$ to $1.0 \times 10^{2}$ cm$^2$/Vs. When the electron mobility and the hole mobility thereof are within the above range, then the compound (1) can be favorably used as a material for semiconductor devices.

In the formula (1), R independently represents hydrogen, or alkyl having from 1 to 24 carbon atoms. Any —CH$_2$— in the alkyl may be replaced by —O—, —S—, —CO— or —SiH$_2$—, any —(CH$_2$)$_2$— may be replaced by —CH=CH— or —C≡C—, and any hydrogen may be replaced by halogen.

The alkyl group may be linear or branched. When the alkyl group is linear, then the temperature range of the liquid-crystal phase of the compound tends to be broad; and when the alkyl group is branched, then the clear point of the compound may lower but the compatibility thereof with other organic semiconductor materials may tend to better.

In the compound (1), when the carbon number of R is small, then the compound may tend to have excellent properties as an organic semiconductor. On the other hand, when the carbon number of R is large, then the compound (1) may tend to have a liquid-crystal phase with ease. Accordingly, in the invention, it is possible to control the phase transition temperature of the liquid-crystal phase and the temperature range of the liquid-crystal phase thereof by suitably selecting the terminal groups of the compound, whereby the compound can be controlled to have any desired carrier mobility and the possible temperature range for the carrier movement can be suitably controlled. Consequently, the compound (1) is favorably used as an organic semiconductor material.

Suitably selecting the terminal groups of the compound (1) enables configuration control of the molecules of the compound, and therefore, the organic semiconductor film containing the compound (1) may have a reduced defect density. Accordingly, the compound (1) is favorably used as a material for organic semiconductor devices.

Especially in case where the compound (1) is a compound having a liquid-crystal phase, the compound (1) has self alignability (self-organization). Accordingly, the compound (1) can readily reduce the structural defect that may be occurred in organic semiconductor films for use for devices such as transistor, etc.

Preferred examples of R in the above formula (1) include hydrogen, as well as alkyl, alkoxy, alkoxyalkyl, alkoxyalkoxy, thioalkyl, alkylthioalkyl, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, thioalkenyl, alkynyl, alkynyloxy, sila-alkyl and disila-alkyl each having from 1 to 24 carbon atoms of which any hydrogen may be replaced with halogen.

As the halogen, preferred are fluorine and chlorine, and more preferred is fluorine.

More preferred examples of R in the above formula (1) include hydrogen, alkyl having from 1 to 20 carbon atoms, alkoxy having from 1 to 20 carbon atoms, alkenyl having from 2 to 20 carbon atoms, alkynyl having from 2 to 20 carbon atoms, alkoxyalkyl having from 2 to 20 carbon atoms, alkenyloxy having from 2 to 20 carbon atoms, thioalkyl having from 1 to 20 carbon atoms, alkylthioalkyl having from 2 to 20 carbon atoms, and thioalkenyl having from 2 to 20 carbon atoms. Any hydrogen in these groups may be replaced by fluorine.

Even more preferred examples of R in the above formula (1) include alkyl having from 1 to 20 carbon atoms, alkoxy having from 1 to 20 carbon atoms, alkoxyalkyl having from 2 to 20 carbon atoms, alkynyl having from 2 to 20 carbon atoms, thioalkyl having from 1 to 20 carbon atoms, alkylthioalkyl having from 2 to 20 carbon atoms, fluoroalkyl having from 1 to 20 carbon atoms, and fluoroalkoxy having from 1 to 20 carbon atoms. "Fluoroalkyl" means alkyl in which any one or more hydrogen are replaced by fluorines.

Still more preferred examples of R in the above formula (1) include alkyl having from 1 to 20 carbon atoms, alkoxy having from 1 to 20 carbon atoms, thioalkyl having from 1 to 20 carbon atoms, polyfluoroalkyl having from 1 to 20 carbon atoms, and polyfluoroalkoxy having from 1 to 20 carbon atoms.

Most preferred examples of R in the above formula (1) include alkyl having from 1 to 20 carbon atoms, alkoxy having from 1 to 20 carbon atoms, and thioalkyl having from 1 to 20 carbon atoms.

Specific examples of the above alkyl include —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Specific examples of the above alkoxy include —OC$_2$H$_5$, —OC$_3$H$_7$, —OC$_4$H$_9$, —OC$_5$H$_{11}$, —OCH(CH$_3$)C$_3$H$_7$, —OC$_6$H$_{13}$, —OCH(CH$_3$)C$_4$H$_9$, —OC$_7$H$_{15}$, —OCH(CH$_3$)C$_5$H$_{11}$, —OC$_8$H$_{17}$, —OCH(CH$_3$)C$_6$H$_{13}$, —OC$_9$H$_{19}$, —OCH(CH$_3$)C$_7$H$_{15}$, —OC$_{10}$H$_{21}$, —OCH(CH$_3$)C$_8$H$_{17}$, —OC$_{11}$H$_{23}$, —OC$_9$H$_{19}$, —OC$_{12}$H$_{25}$, —OCH(CH$_3$)C$_{10}$H$_{21}$, —OC$_{13}$H$_{27}$, —OC$_{14}$H$_{29}$ and —OC$_{15}$H$_{31}$.

Specific examples of the above alkoxyalkyl include —(CH$_2$)$_2$—O—CH$_3$, —(CH$_2$)$_2$—O—C$_2$H$_5$, —(CH$_2$)$_3$—O—CH$_3$, —(CH$_2$)$_2$CH$_3$, —(CH$_2$)$_3$—O—C$_2$H$_5$, —(CH$_2$)$_2$—O—(CH$_2$)$_3$CH$_3$, —(CH$_2$)$_3$—O—(CH$_2$)$_2$CH$_3$, —(CH$_2$)$_4$—O—C$_2$H$_5$, —(CH$_2$)$_2$—O—(CH$_2$)$_4$CH$_3$, —(CH$_2$)$_3$—O—(CH$_2$)$_3$CH$_3$, —(CH$_2$)$_4$—O—(CH$_2$)$_2$CH$_3$, —(CH$_2$)$_5$—O—C$_2$H$_5$ and —(CH$_2$)$_6$—O—CH$_3$.

Specific examples of the above alkenyl include —CH$_2$CH=CHCH$_3$, —(CH$_2$)$_2$CH=CH$_2$, —CH$_2$CH=CHC$_2$H$_5$, —(CH$_2$)$_2$CH=CHCH$_3$, —(CH$_2$)$_3$CH=CH$_2$, —CH$_2$CH=CH(CH$_2$)$_2$CH$_3$, —(CH$_2$)$_2$CH=CHC$_2$H$_5$, —(CH$_2$)$_3$CH=CHCH$_3$, —(CH$_2$)$_4$CH=CH$_2$, —CH$_2$CH=CH(CH$_2$)$_3$CH$_3$, —(CH$_2$)$_2$CH=CH(CH$_2$)$_2$CH$_3$, —(CH$_2$)$_3$CH=CHC$_2$H$_5$, —(CH$_2$)$_4$CH=CHCH$_3$, —(CH$_2$)$_5$CH=CH$_2$, —CH$_2$CH=CH(CH$_2$)$_5$CH$_3$, —(CH$_2$)$_2$CH=CH(CH$_2$)$_4$CH$_3$, —(CH$_2$)$_3$CH=CH(CH$_2$)$_3$CH$_3$, —(CH$_2$)$_4$CH=CH(CH$_2$)$_2$CH$_3$, —(CH$_2$)$_5$CH=CHC$_2$H$_5$, —(CH$_2$)$_6$CH=CHCH$_3$ and —(CH$_2$)$_7$CH=CH$_2$.

Specific examples of the above alkenyloxy include —OCH$_2$CH=CHCH$_3$, —O(CH$_2$)$_2$CH=CH$_2$, —OCH$_2$CH=CHC$_2$H$_5$, —O(CH$_2$)$_2$CH=CHCH$_3$, —O(CH$_2$)$_3$CH=CH$_2$, —OCH$_2$CH=CH(CH$_2$)$_2$CH$_3$, —O(CH$_2$)$_2$CH=CHC$_2$H$_5$, —O(CH$_2$)$_3$CH=CHCH$_3$, —O(CH$_2$)$_4$CH=CH$_2$, —OCH$_2$CH=CH(CH$_2$)$_3$CH$_3$, —O(CH$_2$)$_2$CH=CH(CH$_2$)$_2$CH$_3$, —O(CH$_2$)$_3$CH=CHC$_2$H$_5$, —O(CH$_2$)$_4$CH=CHCH$_3$, —O(CH$_2$)$_5$CH=CH$_2$, —OCH$_2$CH=CH(CH$_2$)$_5$CH$_3$, —O(CH$_2$)$_2$CH=CH(CH$_2$)$_4$CH$_3$, —O(CH$_2$)$_3$CH=CH(CH$_2$)$_3$CH$_3$, —O(CH$_2$)$_4$CH=CH(CH$_2$)$_2$CH$_3$, —O(CH$_2$)$_5$CH=CHC$_2$H$_5$, —O(CH$_2$)$_6$CH=CHCH$_3$ and —O(CH$_2$)$_7$CH=CH$_2$.

Specific examples of the above alkynyl include —C≡CC$_2$H$_5$, —C≡C(CH$_2$)$_2$CH$_3$, —C≡C(CH$_2$)$_3$CH$_3$, —C≡C(CH$_2$)$_4$CH$_3$, —C≡C(CH$_2$)$_5$CH$_3$, —C≡C(CH$_2$)$_6$CH$_3$ and —C≡C(CH$_2$)$_7$CH$_3$.

Specific examples of the above thioalkyl include —SC$_2$H$_5$, —SC$_3$H$_7$, —SC$_4$H$_9$, —SC$_5$H$_{11}$, —SCH(CH$_3$)C$_3$H$_7$, —SC$_6$H$_{13}$, —SCH(CH$_3$)C$_4$H$_9$, —SC$_7$H$_{15}$, —SCH(CH$_3$)C$_5$H$_{11}$, —SC$_8$H$_{17}$, —SCH(CH$_3$)C$_6$H$_{13}$, —SC$_9$H$_{19}$, —SCH(CH$_3$)C$_7$H$_{15}$, —SC$_{10}$H$_{21}$, —SCH(CH$_3$)C$_8$H$_{17}$, —SC$_{11}$H$_{23}$, —SCH(CH$_3$)C$_9$H$_{19}$, —SC$_{12}$H$_{25}$, —SCH(CH$_3$)C$_{10}$H$_{21}$, —SC$_{13}$H$_{27}$, —SC$_{14}$H$_{29}$ and —SC$_{15}$H$_{31}$.

Specific examples of the above alkylthioalkyl include —(CH$_2$)$_2$—S—CH$_3$, —(CH$_2$)$_2$—S—C$_2$H$_5$, —(CH$_2$)$_3$—S—CH$_3$, —(CH$_2$)$_2$—S—(CH$_2$)$_2$CH$_3$, —(CH$_2$)$_3$—S—C$_2$H$_5$, —(CH$_2$)$_2$—S—(CH$_2$)$_3$CH$_3$, —(CH$_2$)$_3$—S—(CH$_2$)$_2$CH$_3$, —(CH$_2$)$_4$—S—C$_2$H$_5$, —(CH$_2$)$_2$—S—(CH$_2$)$_4$CH$_3$, —(CH$_2$)$_3$—S—(CH$_2$)$_3$CH$_3$, —(CH$_2$)$_4$—S—(CH$_2$)$_2$CH$_3$, —(CH$_2$)$_5$—S—C$_2$H$_5$ and —(CH$_2$)$_6$—S—CH$_3$.

Specific examples of the alkyl in which at least one hydrogen is replaced by halogen include —CH$_2$CF$_3$, —(CH$_2$)$_2$CF$_3$, —(CH$_2$)$_3$CF$_3$, —(CH$_2$)$_3$CH$_2$F, —(CH$_2$)$_3$CF$_2$CF$_3$, —(CH$_2$)$_3$(CF$_2$)$_2$CF$_3$, —CH$_2$CHF(CH$_2$)$_3$CH$_3$, —(CH$_2$)$_3$(CF$_2$)$_3$CF$_3$, —CH$_2$CHF(CH$_2$)$_4$CH$_3$, —(CH$_2$)$_3$(CF$_2$)$_4$CF$_3$, —CH$_2$CHF(CH$_2$)$_5$CH$_3$, —(CH$_2$)$_3$(CF$_2$)$_5$CF$_3$, —CH$_2$CHF(CH$_2$)$_6$CH$_3$, —(CH$_2$)$_3$(CF$_2$)$_6$CF$_3$ and —CH$_2$CHF(CH$_2$)$_7$CH$_3$.

Specific examples of the alkoxy in which at least one hydrogen is replaced by halogen include —OCH$_2$CF$_3$, —O(CH$_2$)$_2$CF$_3$, —O(CH$_2$)$_3$CF$_3$, —O(CH$_2$)$_3$CH$_2$F, —O(CH$_2$)$_3$CF$_2$CF$_3$, —O(CH$_2$)$_3$(CF$_2$)$_2$CF$_3$, —OCH$_2$CHF(CH$_2$)$_3$CH$_3$, —O(CH$_2$)$_3$(CF$_2$)$_3$CF$_3$, —OCH$_2$CHF(CH$_2$)$_4$CH$_3$, —O(CH$_2$)$_3$(CF$_2$)$_4$CF$_3$, —OCH$_2$CHF(CH$_2$)$_5$CH$_3$, —O(CH$_2$)$_3$(CF$_2$)$_5$CF$_3$, —OCH$_2$CHF(CH$_2$)$_6$CH$_3$, —O(CH$_2$)$_3$(CF$_2$)$_6$CF$_3$ and —OCH$_2$CHF(CH$_2$)$_7$CH$_3$.

Specific examples of the alkenyl in which at least one hydrogen may be replaced by halogen include —CH$_2$CF=CFCF$_3$, —(CH$_2$)$_2$CH=CF$_2$, —CH$_2$CF=CFC$_2$F$_5$, —(CH$_2$)$_2$CF=CFCF$_3$, —(CH$_2$)$_3$CH=CF$_2$, —CH$_2$CF=CF(CF$_2$)$_2$CF$_3$, —(CH$_2$)$_2$CF=CFC$_2$F$_5$, —(CH$_2$)$_3$CF=CFCF$_3$, —(CH$_2$)$_4$CH=CF$_2$, —CH$_2$CF=CF(CF$_2$)$_3$CF$_3$, —(CH$_2$)$_2$CF=CF(CF$_2$)$_2$CF$_3$, —(CH$_2$)$_3$CF=CFC$_2$F$_5$, —(CH$_2$)$_4$CF=CFCF$_3$, —(CH$_2$)$_5$CH=CF$_2$, —CH$_2$CF=CF(CF$_2$)$_5$CF$_3$, —(CH$_2$)$_2$CF=CF(CF$_2$)$_4$CF$_3$, —(CH$_2$)$_3$CF=CF(CF$_2$)$_3$CF$_3$, —(CH$_2$)$_4$CF=CF(CF$_2$)$_2$CF$_3$, —(CH$_2$)$_5$CF=CFC$_2$F$_5$, —(CH$_2$)$_6$CF=CFCF$_3$ and —(CH$_2$)$_7$CH=CF$_2$.

Specific examples of preferred R include —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —OC$_2$H$_5$, —OC$_3$H$_7$, —OC$_4$H$_9$, —OC$_5$H$_{11}$, —OCH(CH$_3$)C$_3$H$_7$, —OC$_6$H$_{13}$, —OCH(CH$_3$)C$_4$H$_9$, —OC$_7$H$_{15}$, —OCH(CH$_3$)C$_5$H$_{11}$, —OC$_8$H$_{17}$, —OCH(CH$_3$)C$_6$H$_{13}$, —OC$_9$H$_{19}$, —OCH(CH$_3$)C$_7$H$_{15}$, —OC$_{10}$H$_{21}$, —OCH(CH$_3$)C$_8$H$_{17}$, —OC$_{11}$H$_{23}$, —OCH(CH$_3$)C$_9$H$_{19}$, —OC$_{12}$H$_{25}$, —OCH(CH$_3$C$_{10}$H$_{21}$, —(CH$_2$)$_2$—O—CH$_3$, —(CH$_2$)$_3$—O—CH$_3$, —(CH$_2$)$_3$—O—C$_2$H$_5$, —(CH$_2$)$_4$—O—C$_2$H$_5$, —(CH$_2$)$_5$—O—C$_2$H$_5$, —(CH$_2$)$_6$—O—CH$_3$, —(CH$_2$)$_2$CH=CH$_2$, —(CH$_2$)$_3$CH=CH$_2$, —(CH$_2$)$_4$CH=CH$_2$, —(CH$_2$)$_5$CH=CH$_2$, —(CH$_2$)$_7$CH=CH$_2$, —O(CH$_2$)$_3$CH=CH$_2$, —O(CH$_2$)$_4$CH=CH$_2$, —O(CH$_2$)$_5$CH=CH$_2$, —O(CH$_2$)$_7$CH=CH$_2$, —SC$_4$H$_9$, —SC$_5$H$_{11}$, —SCH(CH$_3$)C$_3$H$_7$, —SC$_6$H$_{13}$, —SCH(CH$_3$)C$_4$H$_9$, —SC$_7$H$_{15}$, —SCH(CH$_3$)C$_5$H$_{11}$, —SC$_8$H$_{17}$, —SCH(CH$_3$)C$_6$H$_{13}$, —SC$_9$H$_{19}$, —SCH(CH$_3$)C$_7$H$_{15}$, —SC$_{10}$H$_{21}$, —SCH(CH$_3$)C$_8$H$_{17}$, —SC$_{11}$H$_{23}$, —SCH(CH$_3$)C$_9$H$_{19}$, —SC$_{12}$H$_{25}$, —SCH(CH$_3$)C$_{10}$H$_{21}$, —(CH$_2$)$_2$—S—CH$_3$, —(CH$_2$)$_2$—S—C$_2$H$_5$, —(CH$_2$)$_3$—S—CH$_3$, —(CH$_2$)$_3$—S—C$_2$H$_5$, —(CH$_2$)$_4$—S—C$_2$H$_5$, —(CH$_2$)$_5$—S—C$_2$H$_5$, —(CH$_2$)$_6$—S—CH$_3$, —(CH$_2$)$_3$CF$_2$CF$_3$, —(CH$_2$)$_3$(CF$_2$)$_2$CF$_3$, —CH$_2$CHF(CH$_2$)$_3$CH$_3$, —(CH$_2$)$_3$(CF$_2$)$_3$CF$_3$, —CH$_2$CHF(CH$_2$)$_4$CH$_3$, —(CH$_2$)$_3$(CF$_2$)$_4$CF$_3$, —CH$_2$CHF(CH$_2$)$_5$CH$_3$, —(CH$_2$)$_3$(CF$_2$)$_5$CF$_3$, —CH$_2$CHF(CH$_2$)$_6$CH$_3$, —(CH$_2$)$_3$(CF$_2$)$_6$CF$_3$, —CH$_2$CHF(CH$_2$)$_7$CH$_3$, —O(CH$_2$)$_3$CF$_2$CF$_3$, —O(CH$_2$)$_3$(CF$_2$)$_2$CF$_3$, —OCH$_2$CHF(CH$_2$)$_3$CH$_3$, —O(CH$_2$)$_3$(CF$_2$)$_3$CF$_3$, —OCH$_2$CHF(CH$_2$)$_4$CH$_3$, —O(CH$_2$)$_3$(CF$_2$)$_4$CF$_3$, —OCH$_2$CHF(CH$_2$)$_5$CH$_3$, —O(CH$_2$)$_3$(CF$_2$)$_5$CF$_3$, —OCH$_2$CHF(CH$_2$)$_6$CH$_3$, —O(CH$_2$)$_3$(CF$_2$)$_6$CF$_3$ and —OCH$_2$CHF(CH$_2$)$_7$CH$_3$.

Specific examples of more preferred R include —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —OC$_2$H$_5$, —OC$_3$H$_{17}$, —OC$_4$H$_9$, —OC$_5$H$_{11}$, —OCH(CH$_3$)C$_3$H$_7$, —OC$_6$H$_{13}$, —OCH(CH$_3$)C$_4$H$_9$, —OC$_7$H$_{15}$, —OCH(CH$_3$)C$_5$H$_{11}$, —OC$_8$H$_{17}$, —OCH(CH$_3$)C$_6$H$_{13}$, —OC$_9$H$_{19}$, —OCH(CH$_3$)C$_7$H$_{15}$, —OC$_{10}$H$_{21}$, —SC$_4$H$_9$, —SC$_5$H$_{11}$, —SCH(CH$_3$)C$_3$H$_7$, —SC$_6$H$_{13}$, —SCH(CH$_3$)C$_4$H$_9$, —SC$_7$H$_{15}$, —SCH(CH$_3$)C$_5$H$_{11}$, —SC$_8$H$_{17}$, —SCH(CH$_3$)C$_6$H$_{13}$, —SC$_9$H$_{19}$, —SCH(CH$_3$)C$_7$H$_{15}$, —SC$_{10}$H$_{21}$, —SCH(CH$_3$)C$_8$H$_{17}$, —(CH$_2$)$_3$CF$_2$CF$_3$, —(CH$_2$)$_3$(CF$_2$)$_2$CF$_3$, —(CH$_2$)$_3$(CF$_2$)$_3$CF$_3$, —(CH$_2$)$_3$(CF$_2$)$_4$CF$_3$, —(CH$_2$)$_3$(CF$_2$)$_5$CF$_3$, —(CH$_2$)$_3$(CF$_2$)$_6$CF$_3$, —O(CH$_2$)$_3$CF$_2$CF$_3$, —O(CH$_2$)$_3$(CF$_2$)$_2$CF$_3$, —OCH$_2$CHF(CH$_2$)$_3$CH$_3$, —O(CH$_2$)$_3$(CF$_2$)$_3$CF$_3$, —OCH$_2$CHF(CH$_2$)$_4$CH$_3$, —O(CH$_2$)$_3$(CF$_2$)$_4$CF$_3$, —OCH$_2$CHF(CH$_2$)$_5$CH$_3$, —O(CH$_2$)$_3$(CF$_2$)$_5$CF$_3$, —OCH$_2$CHF(CH$_2$)$_6$CH$_3$, —O(CH$_2$)$_3$(CF$_2$)$_6$CF$_3$ and —OCH$_2$CHF(CH$_2$)$_7$CH$_3$.

Specific examples of most preferred R include —C$_3$H$_7$, —C$_4$H$_9$, —O$_5$H$_{11}$, —C$_6$H$_{13}$, —C$_7$H$_{15}$, —C$_8$H$_{17}$, —C$_9$H$_{19}$, —C$_{10}$H$_{21}$, —OC$_2$H$_5$, —OC$_3$H$_7$, —OC$_4$H$_9$, —OC$_5$H$_{11}$, —OCH(CH$_3$)C$_3$H$_7$, —OC$_6$H$_{13}$, —OCH(CH$_3$)C$_4$H$_9$, —OC$_7$H$_{15}$, —OCH(CH$_3$)C$_5$H$_{11}$, —OC$_8$H$_{17}$, —OCH(CH$_3$)C$_6$H$_{13}$, —OC$_9$H$_{19}$, —OC$_{10}$H$_{21}$, —SC$_4$H$_9$, —SC$_5$H$_{11}$, —SCH(CH$_3$)C$_3$H$_7$, —SC$_6$H$_{13}$, —SCH(CH$_3$)C$_4$H$_9$, —SC$_7$H$_{15}$, —SCH(CH$_3$)C$_5$H$_{11}$, —SC$_8$H$_{17}$, —SCH(CH$_3$)C$_6$H$_{13}$, —SC$_9$H$_{19}$, —SC$_{10}$H$_{21}$ and —SCH(CH$_3$)C$_8$H$_{17}$.

In the formula (1), Ar represents naphthylene, anthrylene, phenanthrylene, or phenylene in which every hydrogen is replaced by halogen, preferably naphthylene, anthrylene, or phenylene in which every hydrogen is replaced by halogen, more preferably naphthylene, or phenylene in which every hydrogen is replaced by halogen.

Any hydrogen in naphthylene, anthrylene and phenanthrylene may be replaced by halogen. In case where any hydrogen in naphthylene, anthrylene and phenanthrylene is replaced by halogen, preferred are groups in which every hydrogen in the ring is replaced by halogen.

The halogen is preferably fluorine and chlorine from the viewpoint of the carrier mobility and the thermal stability, more preferably fluorine.

When Ar in the formula (1) is naphthylene, the compound (1) tends to be a compound of which the liquid-crystal phase-isotropic liquid temperature (hereinafter this may be referred to as "clear point") is high. When Ar in the formula (1) is anthrylene, the compound (1) tends to be a compound of which the clear point is further high. When Ar in the formula (1) is phenanthrylene, the compound (1) tends to be a compound having a low clear point. When Ar in the formula (1) is phenylene in which every hydrogen is replaced by halogen, the compound (1) tends to be a compound having a low clear point.

When Ar in the formula (1) is naphthylene, anthrylene or phenanthrylene in which any hydrogen is not replaced by halogen, the compound (1) tends to be a compound excellent in transport of both holes and electrons. When Ar in the formula (1) is phenylene, naphthylene, anthrylene or phenanthrylene in which every hydrogen is replaced by halogen, the compound (1) tends to be a compound especially excellent in transport of electrons.

Examples of phenylene in which every hydrogen is replaced by halogen include 2,3,5,6-tetrachloro-1,4-phenylene, 2,4,5,6-tetrachloro-1,3-phenylene and compounds wherein chlorine in these compounds are replaced by fluorine.

Examples of naphthylene in which any hydrogen is replaced by halogen include 1-chloronaphthalene-2,6-diyl, 4-chloronaphthalene-2,6-diyl, 3,4-dichloronaphthalene-2,6-diyl, 1,3-dichloronaphthalene-2,6-diyl, 1,4-dichloronaphthalene-2,6-diyl, 1,5-dichloronaphthalene-2,6-diyl, 4,7-dichloronaphthalene-2,6-diyl, 1,7-dichloronaphthalene-2,6-diyl, 1,8-dichloronaphthalene-2,6-diyl, 2,3-dichloronaphthalene-1,5-diyl, 3,7-dichloronaphthalene-2,6-diyl, 3,6-dichloronaphthalene-2,7-diyl, 2,3,4-trichloronaphthalene-1,5-diyl, 1,3,4-trichloronaphthalene-2,6-diyl, 3,4,8-trichloronaphthalene-2,6-diyl, 3,4,7-trichloronaphthalene-2,6-diyl, 3,4,6-trichloronaphthalene-2,7-diyl, 3,4,5-trichloronaphthalene-2,6-diyl, 2,3,8-trichloronaphthalene-1,5-diyl, 2,3,6-trichloronaphthalene-1,5-diyl, 2,3,7-trichloronaphthalene-1,5-diyl, 1,4,5,8-tetrachloronaphthalene-2,6-diyl, 2,3,6,7-tetrachloronaphthalene-1.5-diyl, 1,3,4,5,7,8-hexachloronaphthalene-2,6-diyl, 2,3,4,6,7,8-hexachloronaphthalene-1,5-diyl,1,3,4,6,7,8-hexa chloronaphthalene-2,5-diyl and compounds wherein chlorine in these compounds are replaced by fluorine.

Examples of anthrylene in which any hydrogen is replaced by halogen include 1-chloroanthracene-2,6-diyl, 3-chloroanthracene-2,6-diyl, 9-chloroanthracene-2,6-diyl, 3,4-dichloroanthracene-2,6-diyl, 1,3-dichloroanthracene-2,6-diyl, 1,4-dichloroanthracene-2,6-diyl, 1,5-dichloroanthracene-2,6-diyl, 4,7-dichloroanthracene-2,6-diyl, 1,7-dichloroanthracene-2,6-diyl, 1,8-dichloroanthracene-2,6-diyl, 1,9-dichloroanthracene-2,6-diyl, 1,10-dichloroanthracene-2,6-diyl, 2,3-dichloroanthracene-1,6-diyl, 3,7-dichloroanthracene-2,6-diyl, 3,6-dichloroanthracene-2,7-diyl, 3,10-dichloroanthracene-2,6-diyl, 3,9-dichloroanthracene-2,6-diyl, 9,10-dichloroanthracene-2,6-diyl, 2,3,4-trichloroanthracene-1,6-diyl, 1,3,4-trichloroanthracene-2,6diyl, 3,4,8-trichloroanthracene-2,6-diyl, 3,4,7-trichloroanthracene-2,6-diyl, 3,4,6-trichloroanthracene-2,7-diyl, 3,4,5-trichloroanthracene-2,6-diyl, 3,4,10-trichloroanthracene-2,6-diyl, 3,4,9-trichloroanthracene-2,6-diyl, 2,3,5-trichloroanthracene-1,6-diyl, 2,3,7-trichloroanthracene-1,6-diyl, 2,3,9-trichloroanthracene-1,6-diyl, 1,9,10-trichloroanthracene-2,6-diyl, 3,9,10-trichloroanthracene-2,6-diyl, 1,4,5,8-tetrachloroanthracene-2,6-diyl, 2,3,6,7-tetrachloroanthracene-1,5-diyl, 1,5,9,10-tetrachloroanthracene-2,6-diyl, 3,7,9,10-tetrachloroanthracene-2,6-diyl, 1,3,5,7-tetrachloroanthracene-2,6-diyl, 3,4,7,8-tetrachloroanthracene-2,6-diyl, 5,6,7,8-tetrachloroanthracene-1,4-diyl, 2,3,4,8-tetrachloroanthracene-1,6-diyl, 2,3,4,7-tetrachloroanthracene-1,6-diyl, 2,3,4,6-tetrachloroanthracene-1,5-diyl, 2,3,4,5-tetrachloroanthracene-1,6-diyl, 2,3,4,10-tetrachloroanthracene-1,6-diyl, 2,3,4,9-tetrachloroanthracene-1,6-diyl, 2,3,4,6,7,8,9,10-octachloroanthracene-1,5-diyl, 1,3,4,5,7,8,9,10-octachloroanthracene-2,6-diyl, 1,3,4,5,6,8,9,10-octachloroanthracene-2,7-diyl, 1,3,4,5,6,7,9,10-octafluoroanthracene-2,8-diyl and compounds wherein chlorine in these compounds are replaced by fluorine.

Examples of phenanthrylene in which any hydrogen is replaced by halogen include 1-chlorophenanthrene-2,7-diyl, 2-chlorophenanthrene-1,7-diyl, 3-chlorophenanthrene-2,7-diyl, 4-chlorophenanthrene-2,7-diyl, 9-chlorophenanthrene-2,7-diyl, 7,8-dichlorophenanthrene-2,6-diyl, 1,3-dichlorophenanthrene-2,7-diyl, 1,4-dichlorophenanthrene-2,7-diyl, 1,5-dichlorophenanthrene-2,7-diyl, 1,6-dichlorophenanthrene-2,7-diyl, 2,8-dichlorophenanthrene-1,7-diyl, 1,8-dichlorophenanthrene-2,7-diyl, 1,9-dichlorophenanthrene-2,7-diyl, 1,10-dichlorophenanthrene-2,7-diyl, 2,3-dichlorophenanthrene-1,7-diyl, 2,4-dichlorophenanthrene-1,7-diyl, 2,5-dichlorophenanthrene-1,7-diyl, 2,6-dichlorophenanthrene-1,7-diyl, 2,7-dichlorophenanthrene-1,6-diyl, 2,9-dichlorophenanthrene-1,7-diyl, 2,10-dichlorophenanthrene-1,7-diyl, 3,4-dichlorophenanthrene-2,7-diyl, 3,5-dichlorophenanthrene-2,7-diyl, 3,6-dichlorophenanthrene-2,7-diyl, 3,9-dichlorophenanthrene-2,7-diyl, 3,10-dichlorophenanthrene-2,7-diyl, 4,5-dichlorophenanthrene-2,7-diyl, 4,9-dichlorophenanthrene-2,7-diyl, 4,10-dichlorophenanthrene-2,7-diyl, 6,7,8-trichlorophenanthrene-1,5-diyl, 5,7,8-trichlorophenanthrene-2,6-diyl, 4,7,8-trichlorophenanthrene-2,6-diyl, 3,7,8-trichlorophenanthrene-2,6-diyl, 2,7,8-trichlorophenanthrene-2,6-diyl, 1,7,8-trichlorophenanthrene-1,6-diyl, 7,8,10-trichlorophenanthrene-2,6-diyl, 7,8,9-trichlorophenanthrene-2,6-diyl, 1,3,4-trichlorophenanthrene-2,7-diyl, 1,3,5-trichlorophenanthrene-2,7-diyl, 1,3,6-trichlorophenanthrene-2,7-diyl, 2,6,8-trichlorophenanthrene-1,7-diyl, 1,3,8-trichlorophenanthrene-2,7-diyl, 1,3,9-trichlorophenanthrene-2,7-diyl, 1,3,10-trichlorophenanthrene-2,7-diyl, 1,4,5-trichlorophenanthrene-2,7-diyl, 1,4,6-trichlorophenanthrene-2,7-diyl, 2,5,8-trichlorophenanthrene-1,7-diyl, 1,4,8-trichlorophenanthrene-2,7-diyl, 1,4,9-trichlorophenanthrene-2,7-diyl, 1,4,10-trichlorophenanthrene-2,7-diyl, 2,3,4-trichlorophenanthrene-2,7-diyl, 2,3,5-trichlorophenanthrene-1,7-diyl, 2,3,6- trichlorophenanthrene-1,7-diyl, 2,3,7-trichlorophenanthrene-1,6-diyl, 2,3,8-trichlorophenanthrene-1,7-diyl, 2,3,9-trichlorophenanthrene-1,7-diyl, 2,3,10-trichlorophenanthrene-1,7-diyl, 3,4,5-trichlorophenanthrene-2,7-diyl, 3,4,6-trichlorophenanthrene-2,7-diyl, 2,5,6-trichlorophenanthrene-1,7-diyl, 3,4,8-trichlorophenanthrene-2,7-diyl, 3,4,9-trichlorophenanthrene-2,7-diyl, 3,4,10-trichlorophenanthrene-2,7-diyl, 1,9,10-trichlorophenanthrene-2,7-diyl, 2,9,10-trichlorophenanthrene-1,7-diyl, 3,9,10-trichlorophenanthrene-2,7-diyl, 4,9,10-trichlorophenanthrene-2,7-diyl, 1,2,7,8-tetrachlorophenanthrene-3,6-diyl, 1,3,6,8-tetrachlorophenanthrene-2,7-diyl, 1,4,5,8-tetrachlorophenanthrene-2,7-diyl, 2,3,6,7-tetrachlorophenanthrene-1,8-diyl, 2,4,5,7-tetrachlorophenanthrene-1,6-diyl, 3,4,5,6-tetrachlorophenanthrene-2,7-diyl, 1,8,9,10-tetrachlorophenanthrene-2,7-diyl, 2,7,9,10-tetrachlorophenanthrene-1,6-diyl, 3,6,9,10-tetrachlorophenanthrene-2,7-diyl, 4,5,9,10-tetrachlorophenanthrene-2,7-diyl, 1,3,4,5,6,8,9,10-octachlorophenanthrene-2,7-diyl, 1,3,4,5,6,7,9,10-octachlorophenanthrene-2,8-diyl, 1,3,4,5,7,8,9,10-octachlorophenanthrene-2,6-diyl, 1,2,4,5,7,8,9,10-octachlorophenanthrene-3,6-diyl, 1,2,4,5,6,7,9,10-octachlorophenanthrene-3,8-diyl, 2,3,4,5,6,7,9,10-octachlorophenanthrene-1,8-diyl and compounds wherein chlorine in these compounds are replaced by fluorine.

Specific examples of preferred Ar include 2,3,5,6-tetrafluoro-1,4-phenylene, naphthalene-2,6-diyl, 1-fluoronaphthalene-2,6-diyl, 4-fluoronaphthalene-2,6-diyl, 3,4-difluoronaphthalene-2,6-diyl, 1,3-difluoronaphthalene-2,6-diyl, 1,4-difluoronaphthalene-2,6-diyl, 1,5-difluoronaphthalene-2,6-diyl, 4,7-difluoronaphthalene-2,6-diyl, 1,7-difluoronaphthalene-2,6-diyl, 1,8-difluoronaphthalene-2,6-diyl, 2,3-difluoronaphthalene-1,5-diyl, 3,7-difluoronaphthalene-2,6-diyl, 3,6-difluoronaphthalene-2,7-diyl, 2,3,4-trifluoronaphthalene-1,5-diyl, 1,3,4-trifluoronaphthalene-2,6-diyl, 3,4,8-trifluoronaphthalene-2,6-diyl, 3,4,7-trifluoronaphthalene-2,6-diyl, 3,4,6-trifluoronaphthalene-2,7-diyl, 3,4,5-trifluoronaphthalene-2,6-diyl, 2,3,8-trifluoronaphthalene-1,5-diyl, 2,3,6-trifluoronaphthalene-1,5-diyl, 2,3,7-trifluoronaphthalene-1,5-diyl, 1,4,5,8-tetrafluoronaphthalene-2,6-diyl, 2,3,6,7-tetrafluoronaphthalene-1,5-diyl, 1,3,4,5,7,8-hexafluoronaphthalene-2,6-diyl, 2,3,4,6,7,8-hexafluoronaphthalene-1,5-diyl, 1,3,4,6,7,8-hexafluoronaphthalene-2,5-diyl, anthracene-2,6-diyl, 1-fluoroanthracene-2,6-diyl, 3-fluoroanthracene-2,6-diyl, 9-fluoroanthracene-2,6-diyl, 3,4-difluoroanthracene-2,6-diyl, 1,3-difluoroanthracene-2,6-diyl, 1,4-difluoroanthracene-2,6-diyl, 1,5-difluoroanthracene-2,6-diyl, 4,7-difluoroanthracene-2,6-diyl, 1,7-difluoroanthracene-2,6-diyl, 1,8-difluoroanthracene-2,6-diyl, 1,9-difluoroanthracene-2,6-diyl, 1,10-difluoroanthracene-2,6-diyl, 2,3-difluoroanthracene-1,6-diyl, 3,7-difluoroanthracene-2,6-diyl, 3,6-difluoroanthracene-2,7-diyl, 3,10-difluoroanthracene-2,6-diyl, 3,9-difluoroanthracene-2,6-diyl, 9,10-difluoroanthracene-2,6-diyl, 2,3,4-trifluoroanthracene-1,6-diyl, 1,3,4-trifluoroanthracene-2,6-diyl, 3,4,8-trifluoroanthracene-2,6-diyl, 3,4,7-trifluoroanthracene-2,6-diyl, 3,4,6-trifluoroanthracene-2,7-diyl, 3,4,5-trifluoroanthracene-2,6-diyl, 3,4,10-trifluoroanthracene-2,6-diyl, 3,4,9-trifluoroanthracene-2,6-diyl, 2,3,5-trifluoroanthracene-1,6-diyl, 2,3,7-trifluoroanthracene-1,6-diyl, 2,3,9-trifluoroanthracene-1,6-diyl, 1,9,10-trifluoroanthracene-2,6-diyl, 3,9,10-trifluoroanthracene-2,6-diyl, 1,4,5,8-tetrafluoroanthracene-2,6-diyl, 2,3,6,7-tetrafluoroanthracene-1,5-diyl, 1,5,9,10-tetrafluoroanthracene-2,6-diyl, 3,7,9,10-tetrafluoroanthracene-2,6-diyl, 1,3,5,7-tetrafluoroanthracene-2,6-diyl, 3,4,7,8-tetrafluoroanthracene-2,6-diyl, 5,6,7,8-tetrafluoroanthracene-1,4-diyl, 2,3,4,8-tetrafluoroanthracene-1,6-diyl, 2,3,4,7-tetrafluoroanthracene-1,6-diyl, 2,3,4,6-tetrafluoroanthracene-1,5-diyl, 2,3,4,5-tetrafluoroanthracene-1,6-diyl, 2,3,4,10-tetrafluoroanthracene-1,6-diyl, 2,3,4,9-tetrafluoroanthracene-1,6-diyl, 2,3,4,6,7,8,9,10-octafluoroanthracene-1,5-diyl, 1,3,4,5,7,8,9,10-octafluoroanthracene-2,6-diyl, 1,3,4,5,6,8,9,10-octafluoroanthracene-2,7-diyl, 1,3,4,5,6,7,9,10-octafluoroanthracene-2,8-diyl, phenanthrene-2,7-diyl, 1-fluorophenanthrene-2,7-diyl, 2-fluorophenanthrene-1,7-diyl, 3-fluorophenanthrene-2,7-diyl, 4-fluorophenanthrene-2,7-diyl, 9-fluorophenanthrene-2,7-diyl, 7,8-difluorophenanthrene-2,6-diyl, 1,3-difluorophenanthrene-2,7-diyl, 1,4-difluorophenanthrene-2,7-diyl, 1,5-difluorophenanthrene-2,7-diyl, 1,6-difluorophenanthrene-2,7-diyl, 2,8-difluorophenanthrene-1,7-diyl, 1,8-difluorophenanthrene-2,7-diyl, 1,9-difluorophenanthrene-2,7-diyl, 1,10-difluorophenanthrene-2,7-diyl, 2,3-difluorophenanthrene-1,7-diyl, 2,4-difluorophenanthrene-1,7-diyl, 2,5-difluorophenanthrene-1,7-diyl, 2,6-difluorophenanthrene-1,7-diyl, 2,7-difluorophenanthrene-1,6-diyl, 2,9-difluorophenanthrene-1,7-diyl, 2,10-difluorophenanthrene-1,7-diyl, 3,4-difluorophenanthrene-2,7-diyl, 3,5-difluorophenanthrene-2,7-diyl, 3,6-difluorophenanthrene-2,7-diyl, 3,9-difluorophenanthrene-2,7-diyl, 3,10-difluorophenanthrene-2,7-diyl, 4,5-difluorophenanthrene-2,7-diyl, 4,9-difluorophenanthrene-2,7-diyl, 4,10-difluorophenanthrene-2,7-diyl, 6,7,8-trifluorophenanthrene-1,5-diyl, 5,7,8-trifluorophenanthrene-2,6-diyl, 4,7,8-trifluorophenanthrene-2,6-diyl, 3,7,8-trifluorophenanthrene-2,6-diyl, 2,7,8-trifluorophenanthrene-1,6-diyl, 1,7,8-trifluorophenanthrene-2,6-diyl, 7,8,10-trifluorophenanthrene-2,6-diyl, 7,8,9-trifluorophenanthrene-2,6-diyl, 1,3,4-trifluorophenanthrene-2,7-diyl, 1,3,5-trifluorophenanthrene-2,7-diyl, 1,3,6-trifluorophenanthrene-2,7-diyl, 2,6,8-trifluorophenanthrene-1,7-diyl, 1,3,8-trifluorophenanthrene-2,7-diyl, 1,3,9-trifluorophenanthrene-2,7-diyl, 1,3,10-trifluorophenanthrene-2,7-diyl, 1,4,5-trifluorophenanthrene-2,7-diyl, 1,4,6-trifluorophenanthrene-2,7-diyl, 2,5,8-trifluorophenanthrene-1,7-diyl, 1,4,8-trifluorophenanthrene-2,7-diyl, 1,4,9-trifluorophenanthrene-2,7-diyl, 1,4,10-trifluorophenanthrene-2,7-diyl, 2,3,4-trifluorophenanthrene-1,7-diyl, 2,3,5-trifluorophenanthrene-1,7-diyl, 2,3,6-trifluorophenanthrene-1,7-diyl, 2,3,7-trifluorophenanthrene-1,6-diyl, 2,3,8-trifluorophenanthrene-1,7-diyl, 2,3,9-trifluorophenanthrene-1,7-diyl, 2,3,10-trifluorophenanthrene-1,7-diyl, 3,4,5-trifluorophenanthrene-2,7-diyl, 3,4,6-trifluorophenanthrene-2,7-diyl, 2,5,6-trifluorophenanthrene-1,7-diyl, 3,4,8-trifluorophenanthrene-2,7-diyl, 3,4,9-trifluorophenanthrene-2,7-diyl, 3,4,10-trifluorophenanthrene-2,7-diyl, 1,9,10-trifluorophenanthrene-2,7-diyl, 2,9,10-trifluorophenanthrene-1,7-diyl, 3,9,10-trifluorophenanthrene-2,7-diyl, 4,9,10-trifluorophenanthrene-2,7-diyl, 1,2,7,8-tetrafluorophenanthrene-3,6-diyl, 1,3,6,8-tetrafluorophenanthrene-2,7-diyl, 1,4,5,8-

| | |
|---|---|
| tetrafluorophenanthrene-2,7-diyl, | 2,3,6,7- |
| tetrafluorophenanthrene-1,8-diyl, | 2,4,5,7- |
| tetrafluorophenanthrene-1,6-diyl, | 3,4,5,6- |
| tetrafluorophenanthrene-2,7-diyl, | 1,8,9,10- |
| tetrafluorophenanthrene-2,7-diyl, | 2,7,9,10- |
| tetrafluorophenanthrene-1,6-diyl, | 3,6,9,10- |
| tetrafluorophenanthrene-2,7-diyl, | 4,5,9,10- |
| tetrafluorophenanthrene-2,7-diyl, | 1,3,4,5,6,8,9,10- |
| octafluorophenanthrene-2,7-diyl, | 1,3,4,5,6,7,9,10- |
| octafluorophenanthrene-2,8-diyl, | 1,3,4,5,7,8,9,10- |
| octafluorophenanthrene-2,6-diyl, | 1,2,4,5,7,8,9,10- |
| octafluorophenanthrene-3,6-diyl, | 1,2,4,5,6,7,9,10- |
| octafluorophenanthrene-3,8-diyl, | 2,3,4,5,6,7,9,10- | octafluorophenanthrene-1,8-diyl and compounds wherein chlorine in these compounds are replaced by fluorine.

The compound (1) can be produced by suitably combining methods in organic synthetic chemistry. Methods for introducing the intended terminal group, ring and binding group into starting materials are described in documents such as Organic Syntheses (John Wiley & Sons, Inc.); Organic Reactions (John Wiley & Sons, Inc.); Comprehensive Organic Synthesis (Pergamon Press); New Experimental Chemistry Course (Maruzen), etc.

One example of a production method for the compound (1) is described with reference to the following scheme.

R and Ar in the following scheme have the same meanings as those of R and Ar in the above formula (1).

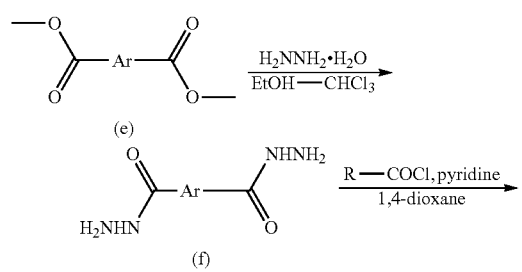

(e)

(f)

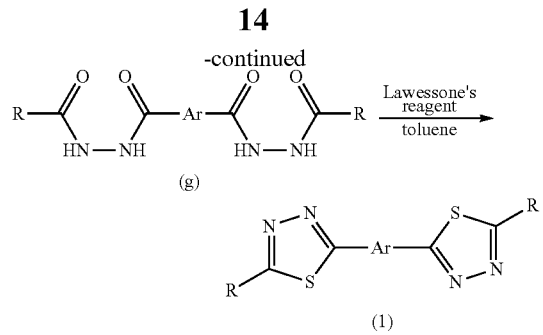

(g)

(1)

As the starting material, used is the compound (e) in which two hydrogens in the aromatic ring each are substituted with a methyl acetate group. The compound (e) is dissolved in a mixed solvent of ethanol(EtOH)-chloroform, and hydrazine hydrate is added thereto, and heated under reflux to give the compound (f).

In a nitrogen atmosphere, the compound (f) is dissolved in 1,4-dioxane, and pyridine and R—COCl are added thereto and stirred. Accordingly, the compound (g) is obtained.

The compound (g) is dissolved in toluene, and a Lawesson's reagent is added thereto, and stirred under heat with reflux. After cooled, the reaction solution is poured into an aqueous 2 N sodium hydroxide solution, and stirred. Subsequently, the solid is separated through suction filtration to give the compound (1).

The obtained compound (1) may be optionally purified, and the purification of the compound (1) may be attained according to an ordinary method of column chromatography, recrystallization or the like.

According to the above-mentioned scheme, the compound (1) of the invention can be produced; however, the invention is not always limited to the above method. Examples of the compounds to be produced according to the above-mentioned method are described below. The structure of the compound produced can be identified through proton NMR spectrometry.

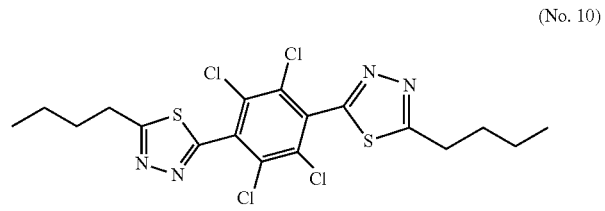

(No. 10)

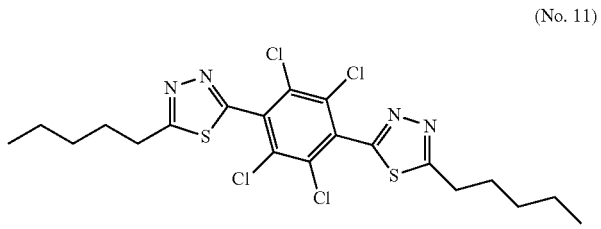

(No. 11)

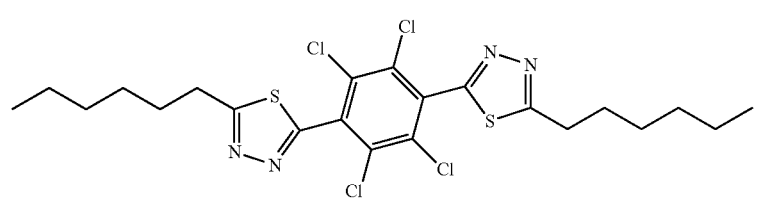

(No. 12)

-continued
(No. 13)
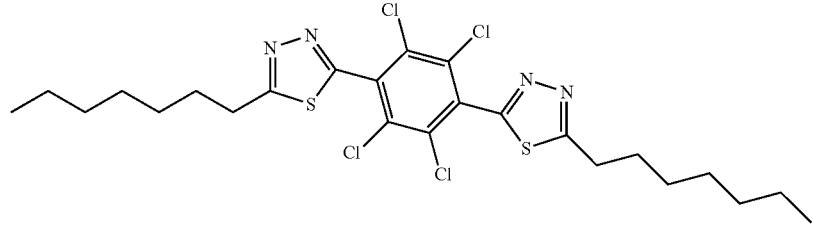
(No. 14)
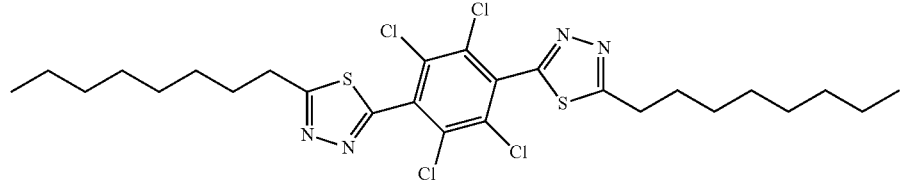
(No. 15)
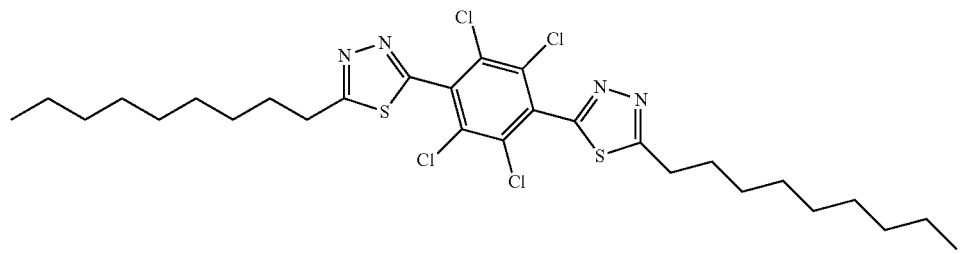
(No. 16)
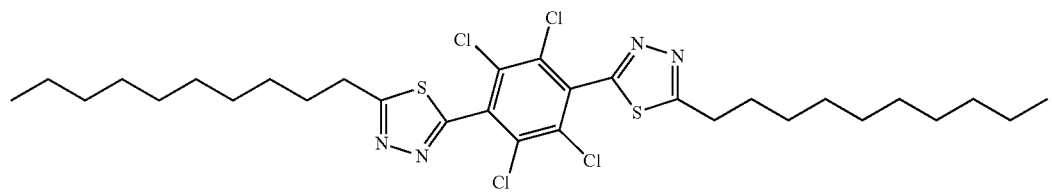
(No. 17)
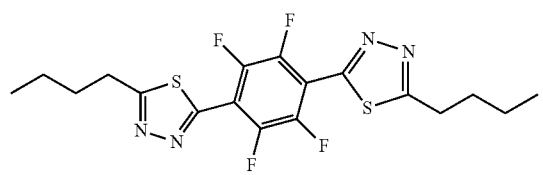
(No. 18)
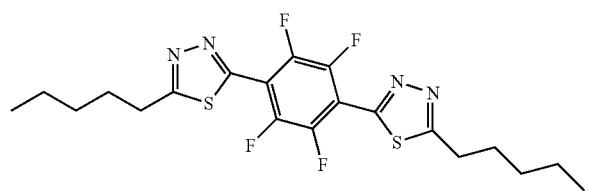
(No. 19)
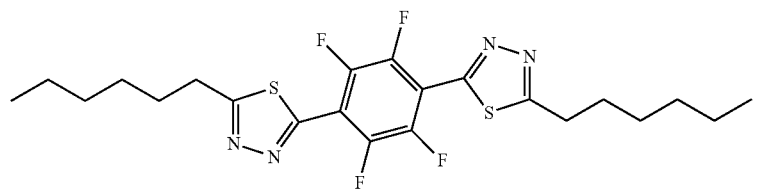
(No. 20)
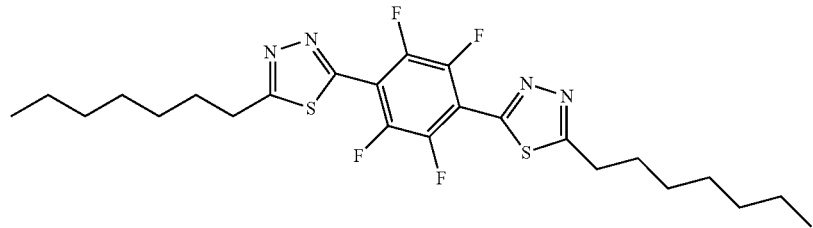

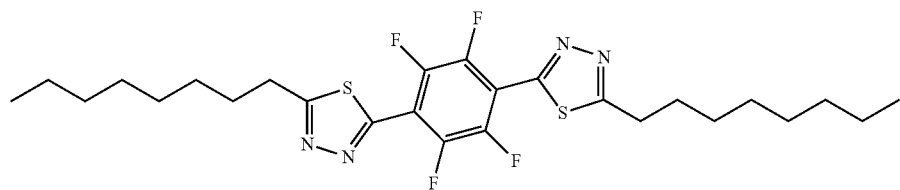
(No. 21)
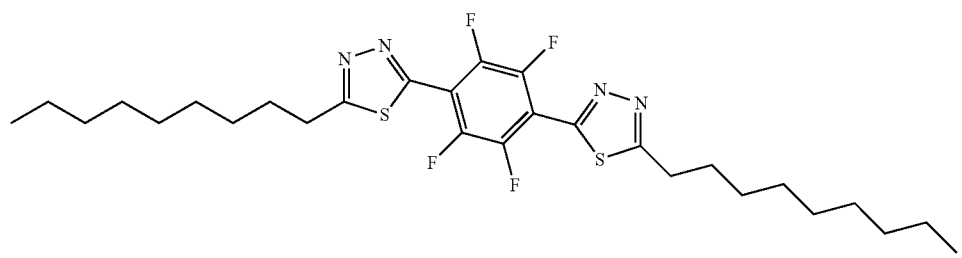
(No. 22)
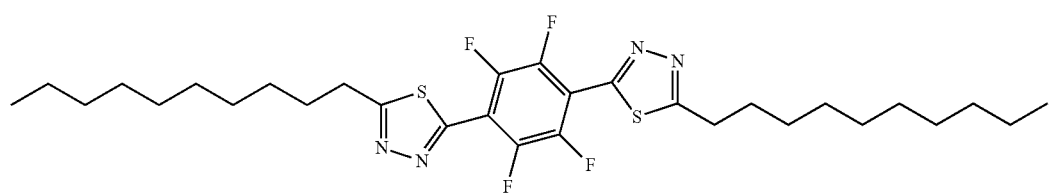
(No. 23)
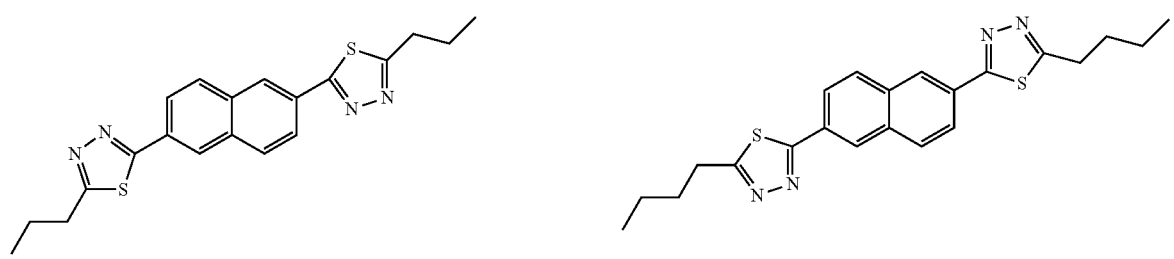
(No. 24)
(No. 25)
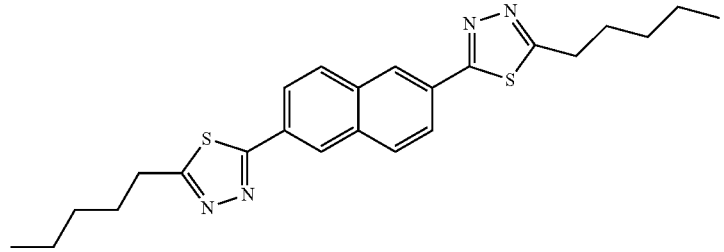
(No. 26)
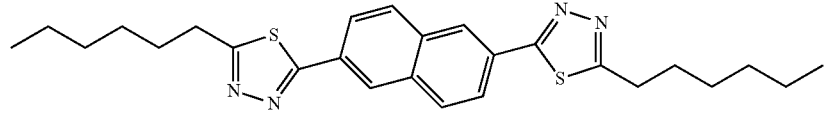
(No. 27)
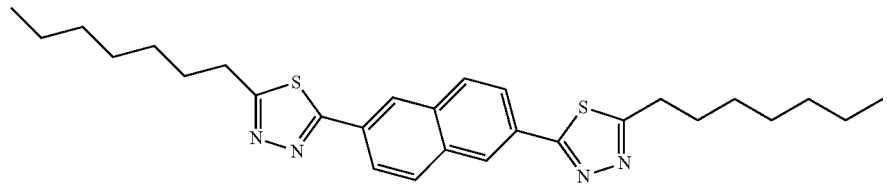
(No. 28)

-continued
(No. 29)
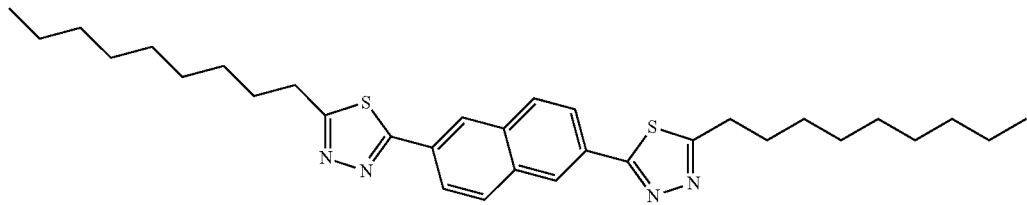
(No. 30)
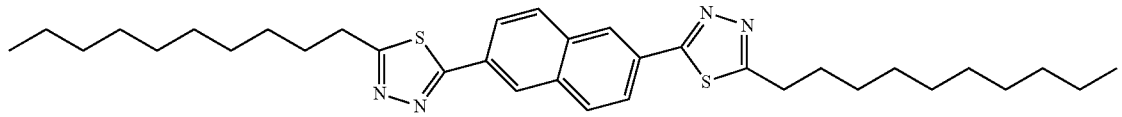
(4)
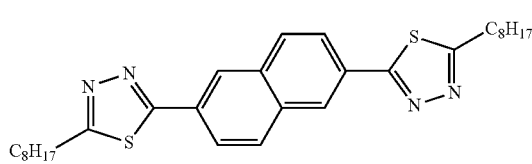
(No. 31)
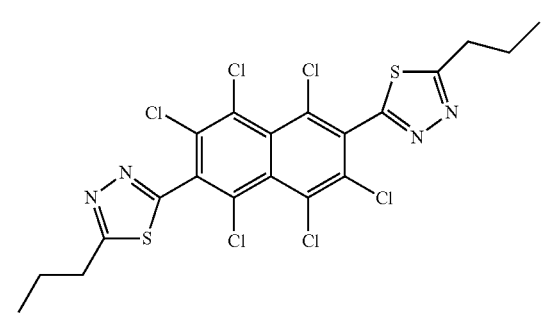
(No. 32)
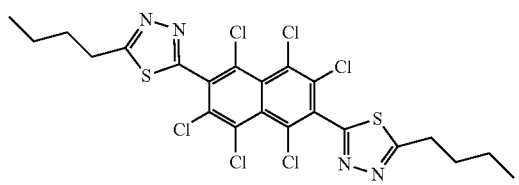
(No. 33)
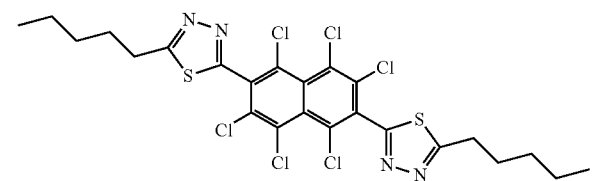
(No. 34)
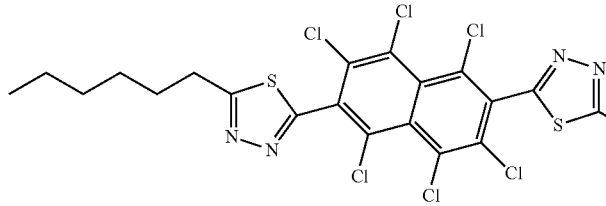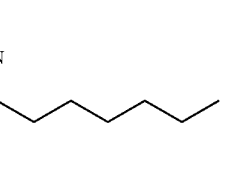
(No. 35)
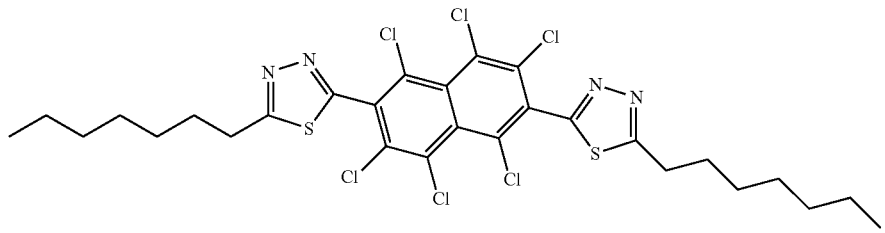
(No. 36)
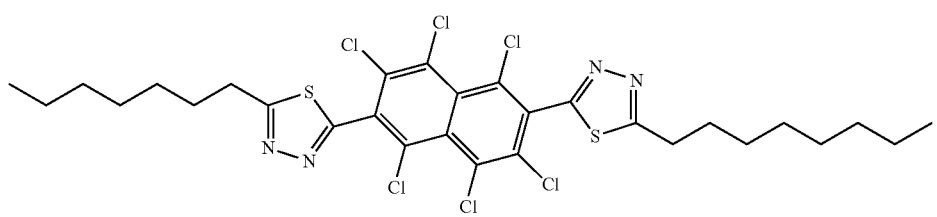

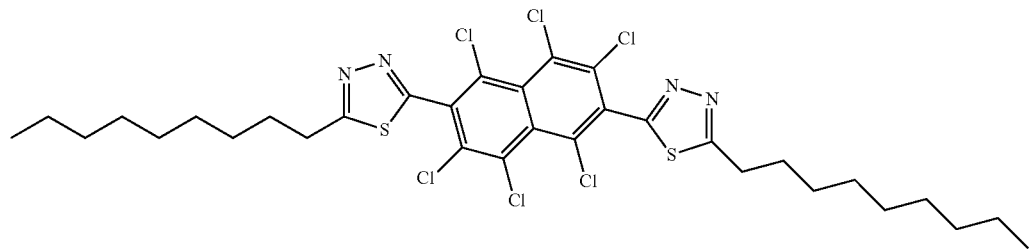
(No. 37)
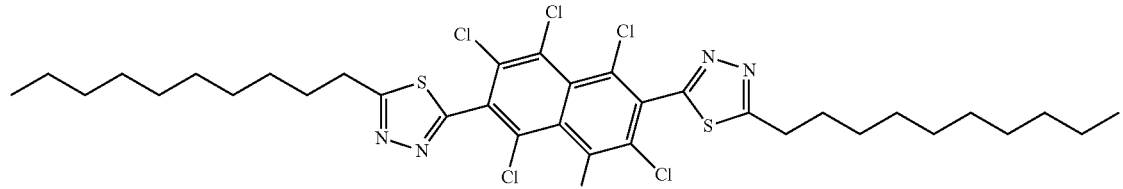
(No. 38)
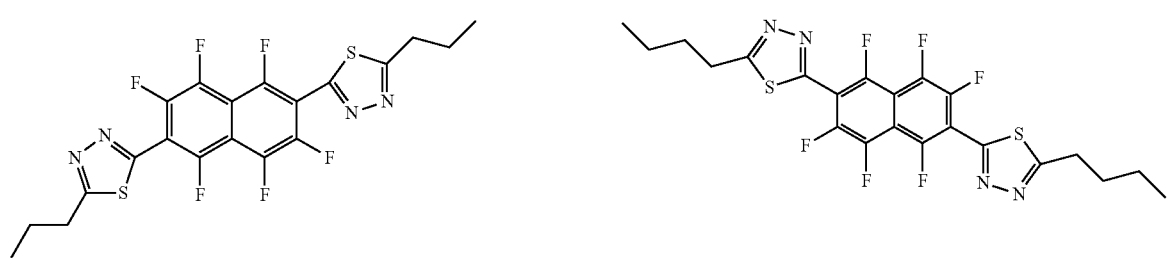
(No. 39)
(No. 40)
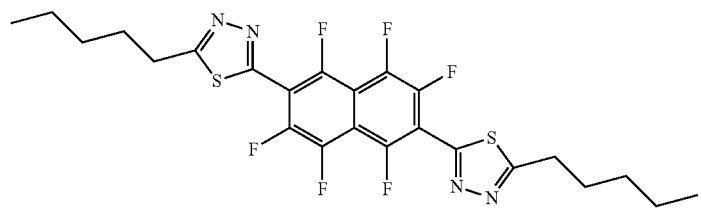
(No. 41)
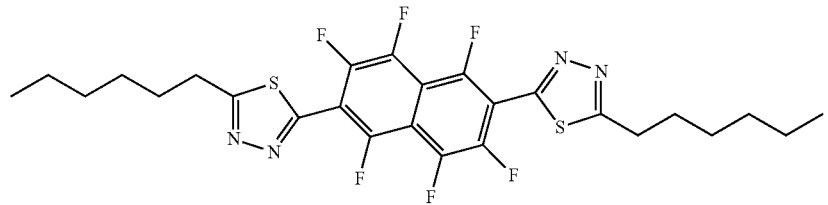
(No. 42)
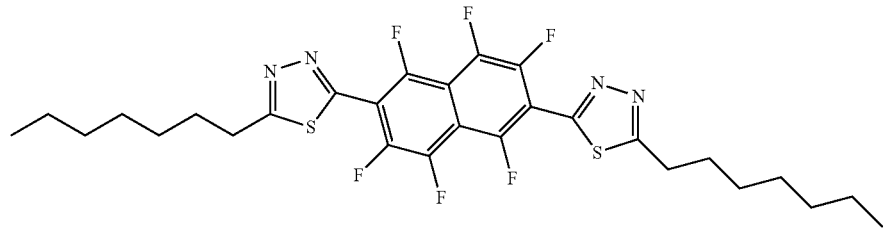
(No. 43)
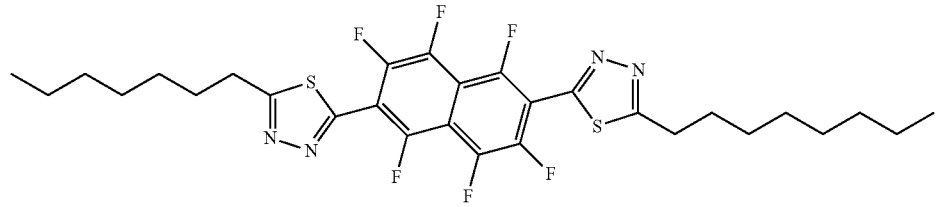
(No. 44)

-continued
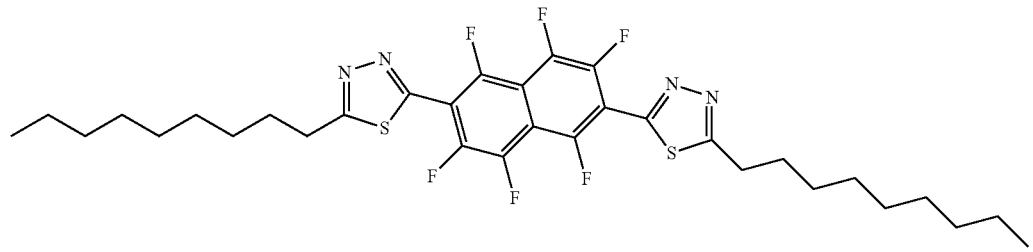
(No. 45)
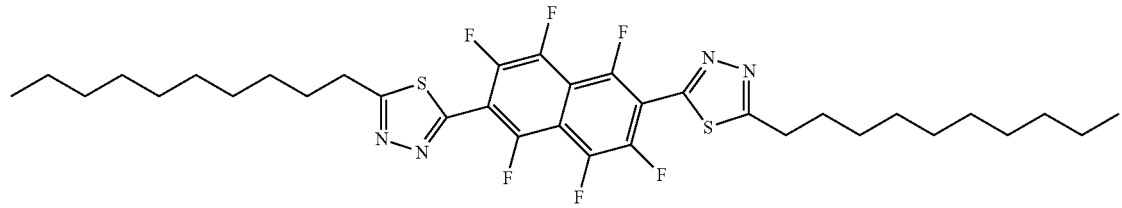
(No. 46)
(No. 47)
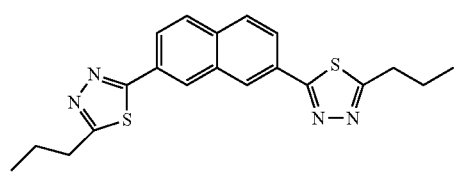
(No. 48)
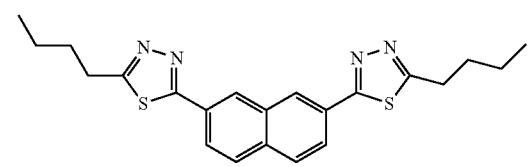
(No. 49)
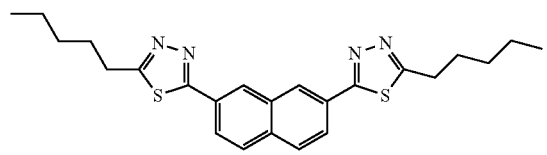
(No. 50)
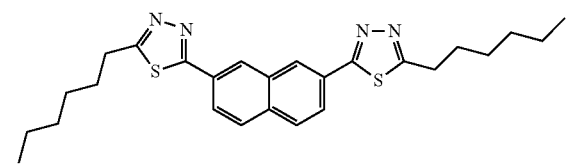
(No. 51)
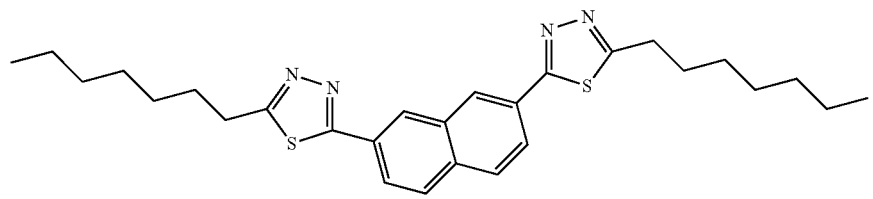
(No. 52)
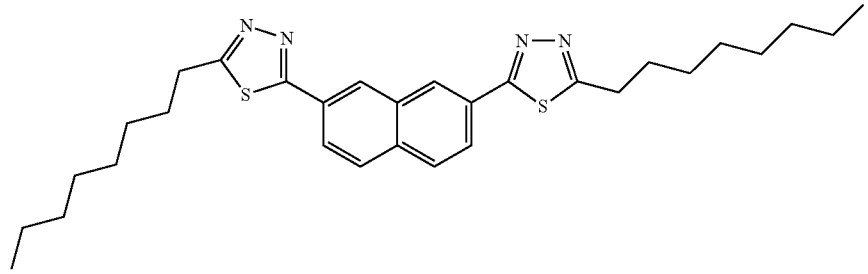
(No. 53)
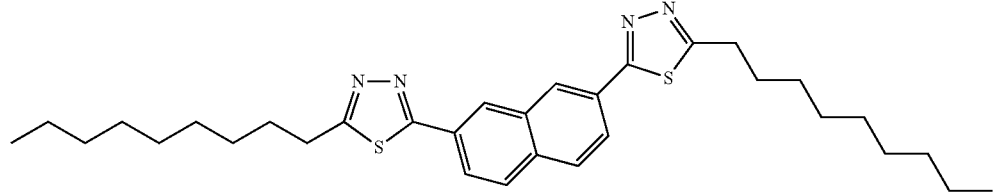

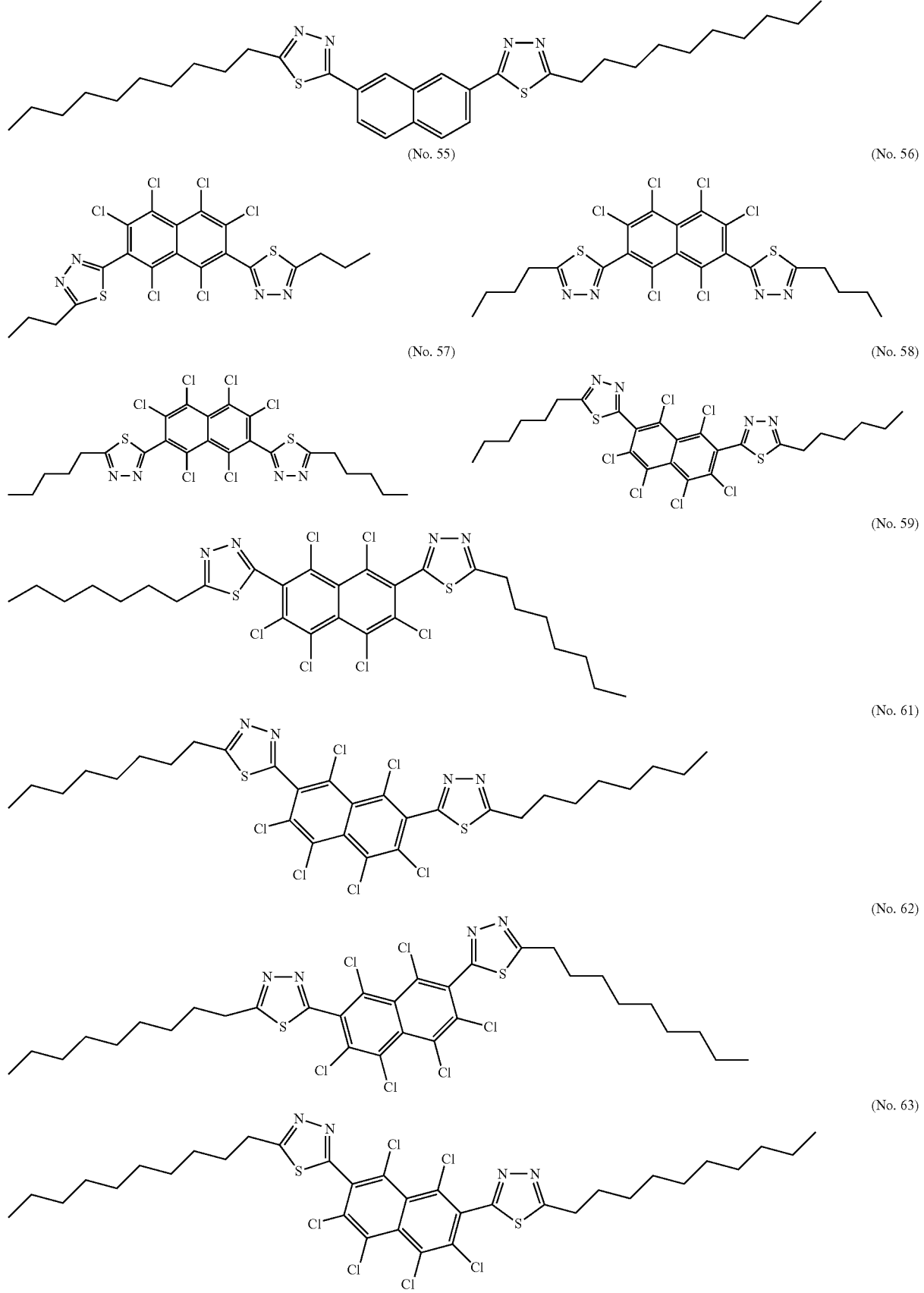

(No. 64)
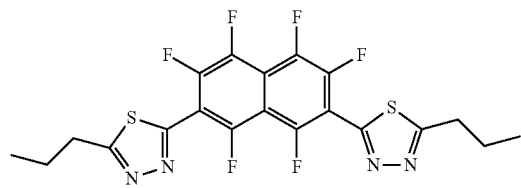
(No. 65)
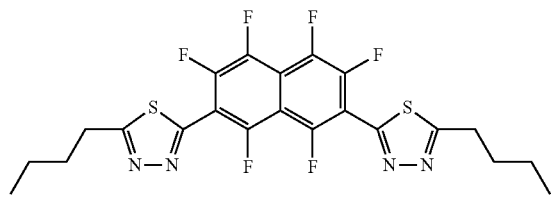
(No. 66)
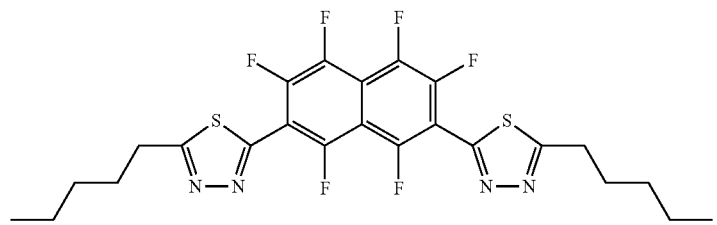
(No. 67)
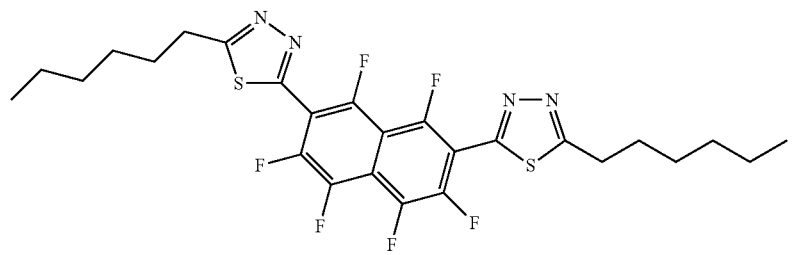
(No. 68)
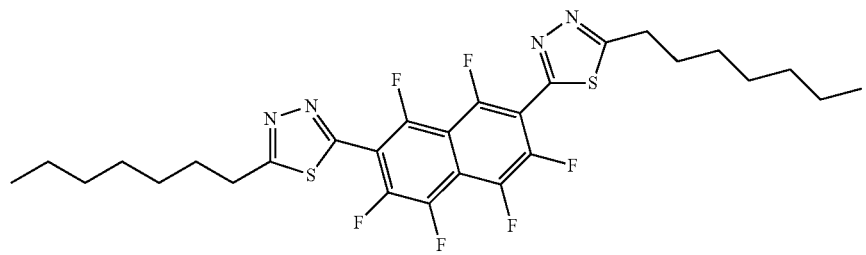
(No. 69)
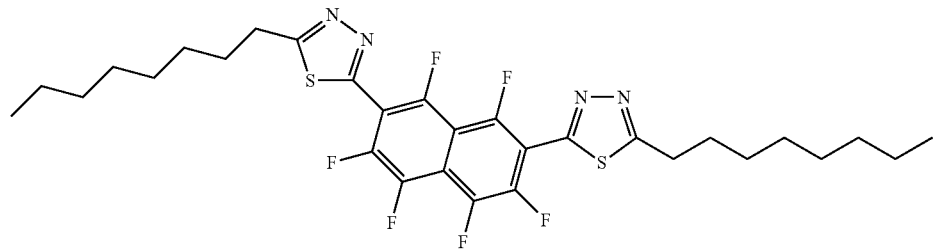
(No. 70)
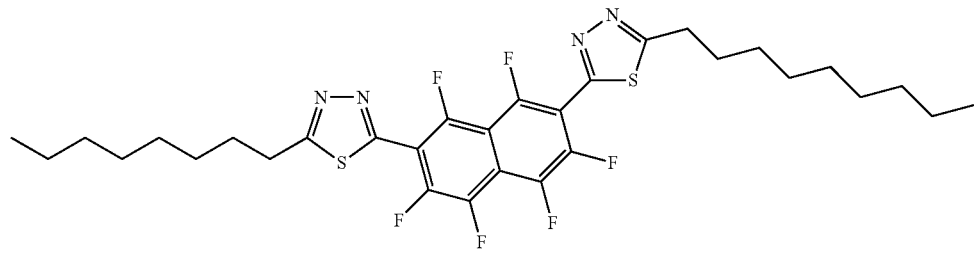

-continued
(No. 71)
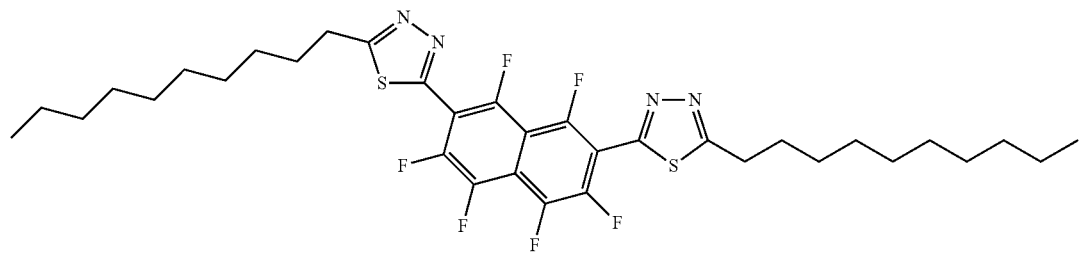
(No. 72)
(No. 73)
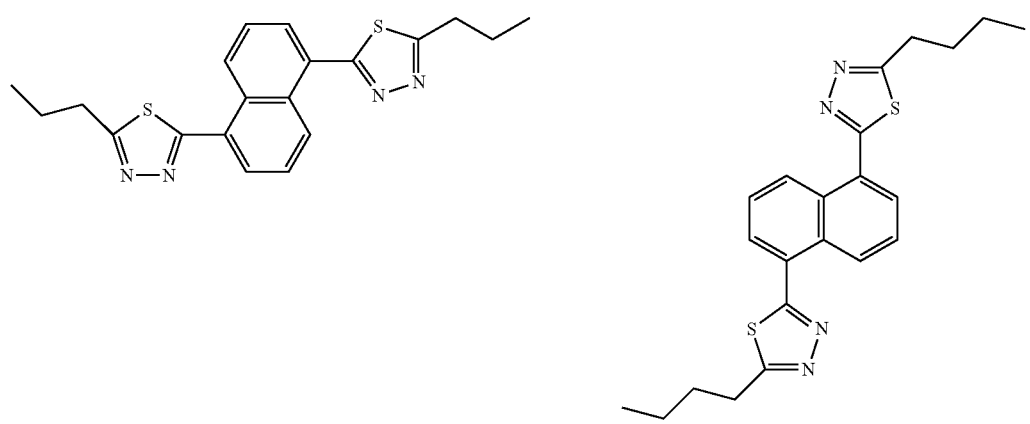
(No. 74)
(No. 75)
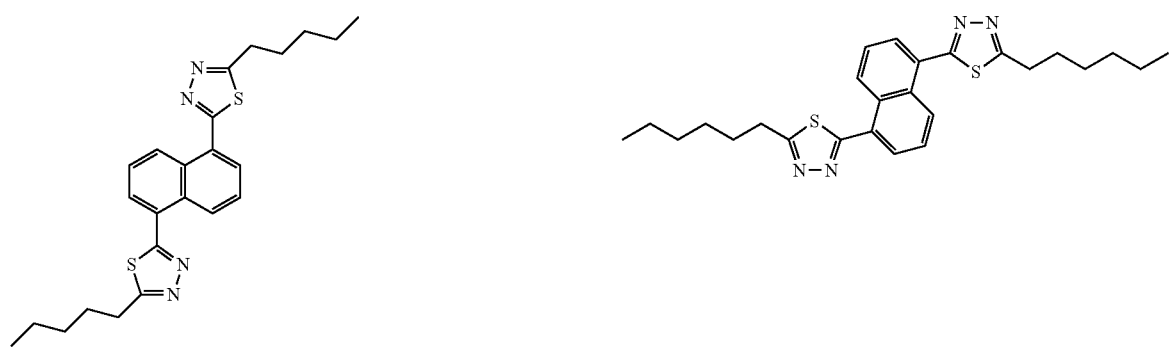
(No. 76)
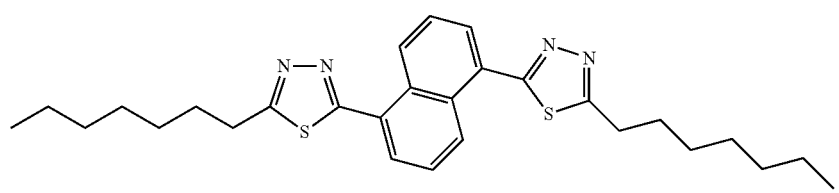
(No. 77)
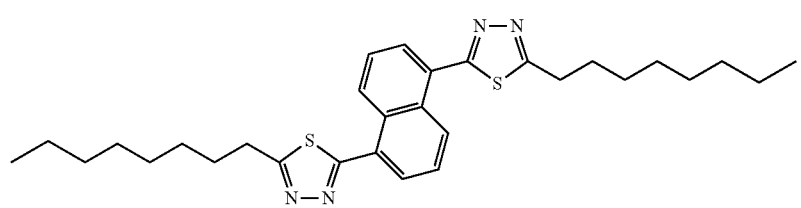

(No. 78)
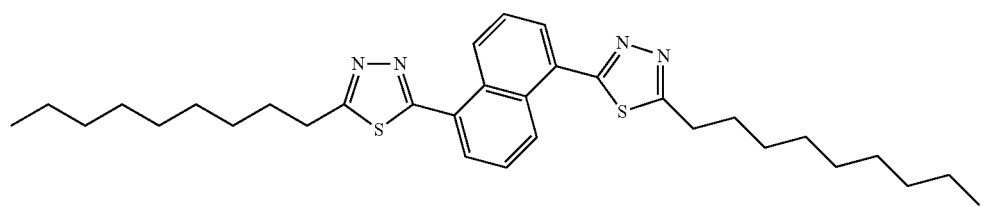
(No. 79)
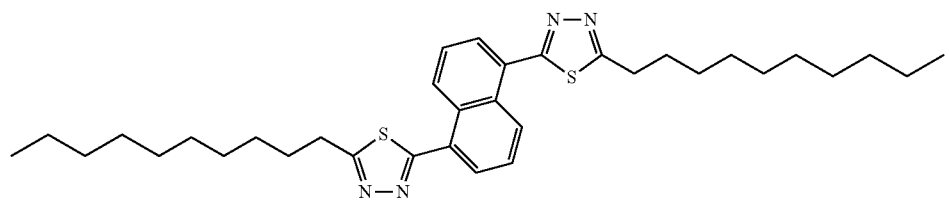
(No. 80)
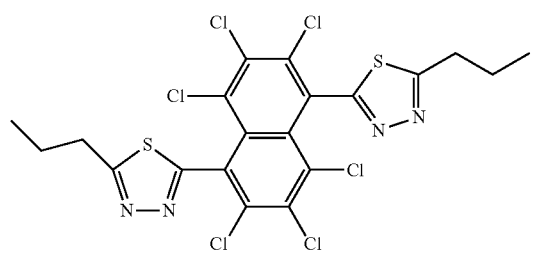
(No. 81)
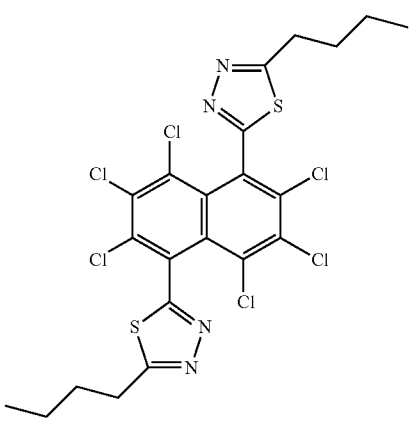
(No. 82)
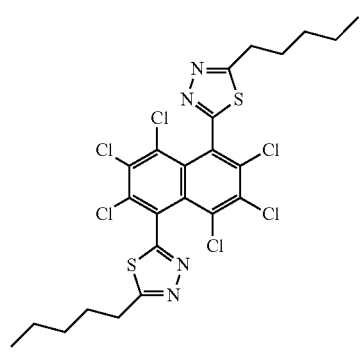
(No. 83)
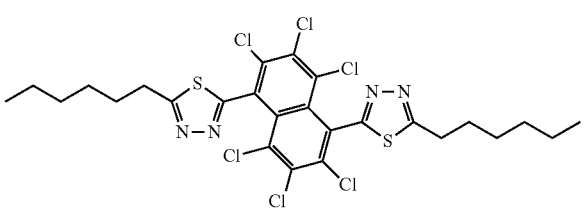
(No. 84)
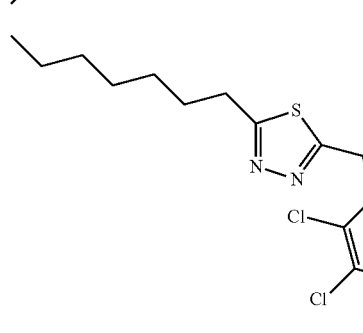

-continued
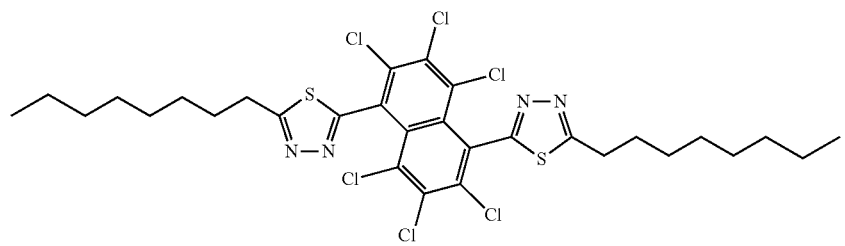
(No. 85)
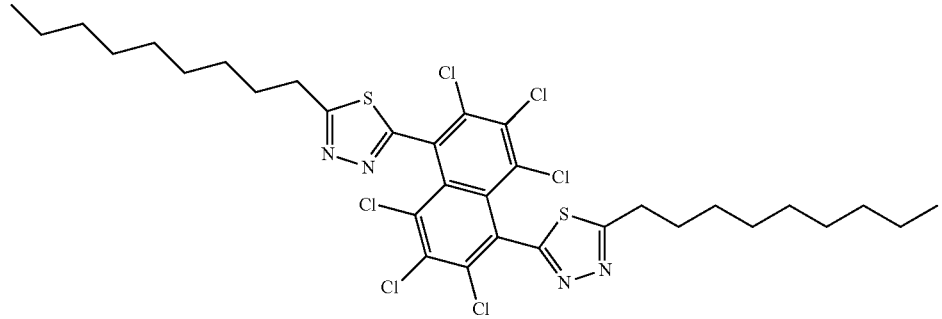
(No. 86)
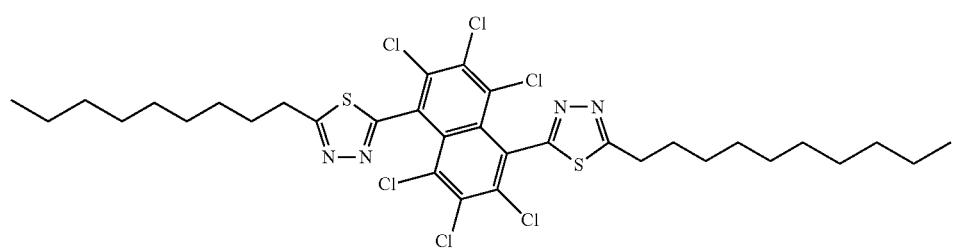
(No. 87)
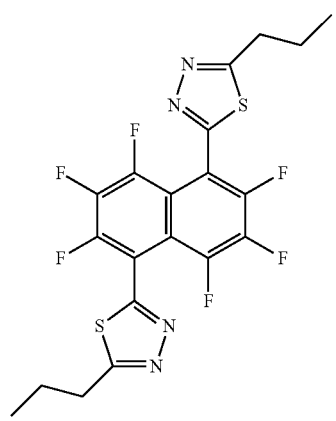
(No. 88)
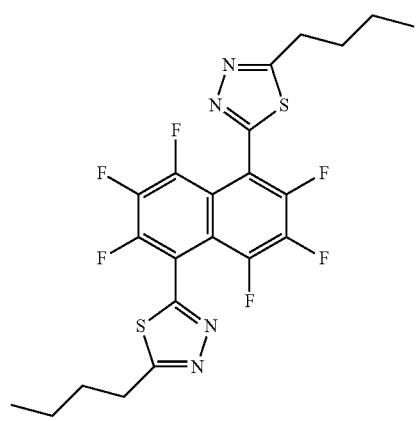
(No. 89)
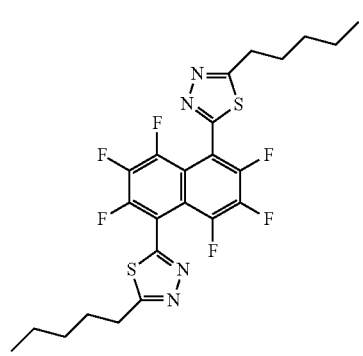
(No. 90)
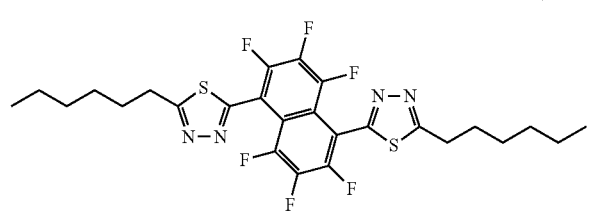
(No. 91)

-continued
(No. 92)
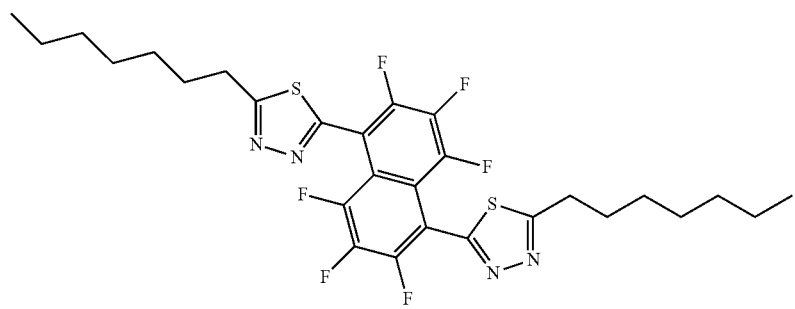
(No. 93)
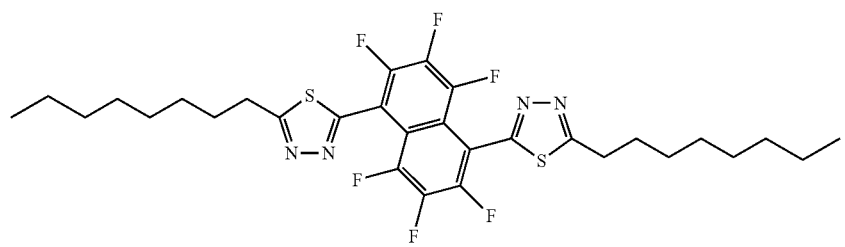
(No. 94)
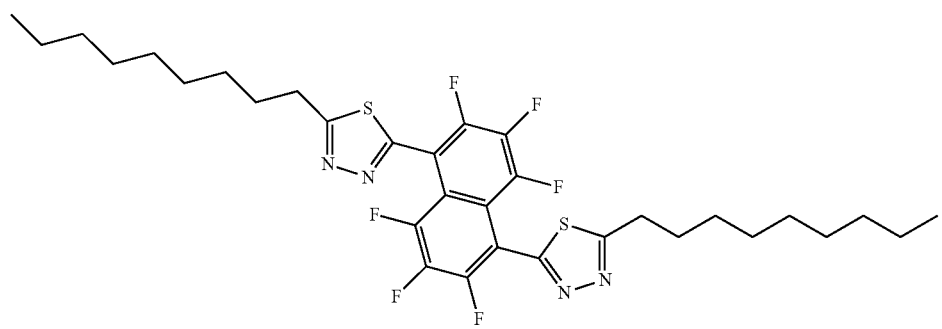
(No. 95)
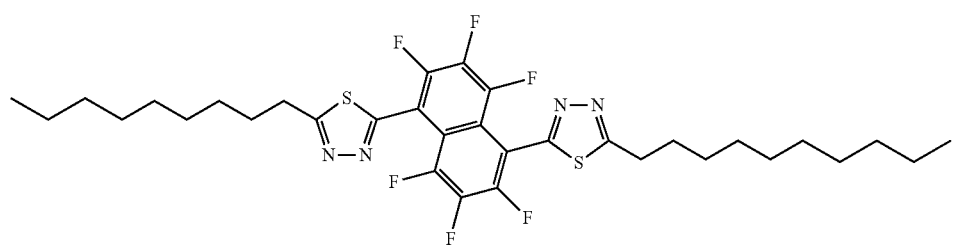
(No. 96)
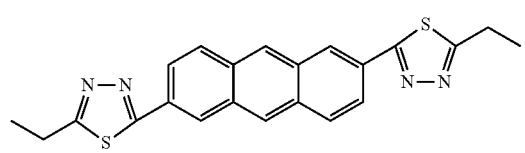
(No. 97)
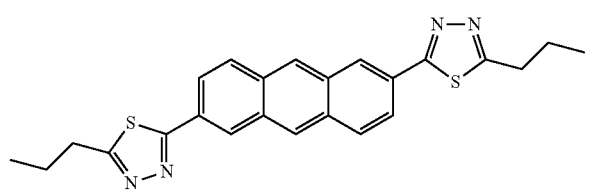
(No. 98)
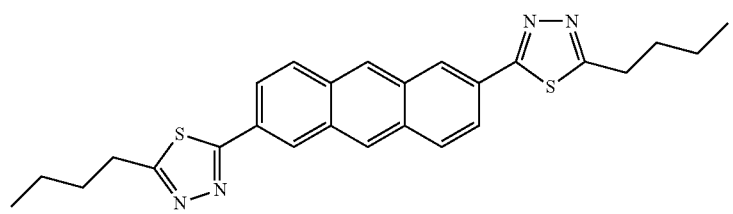

-continued
(No. 99)
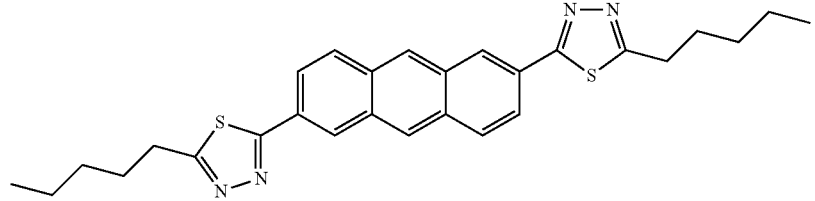
(No. 100)
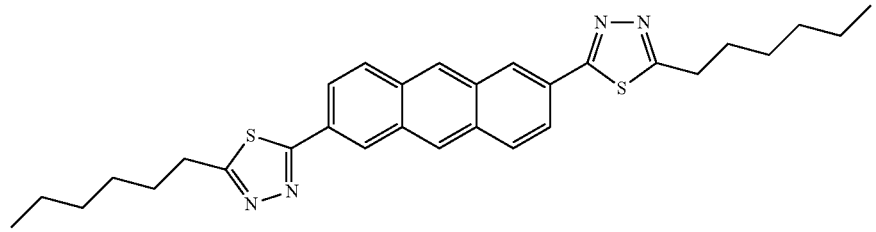
(No. 101)
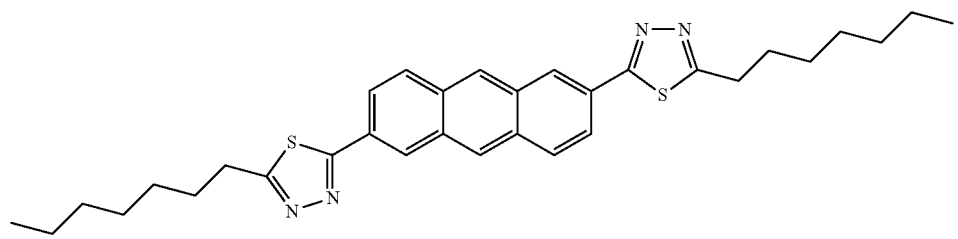
(No. 102)
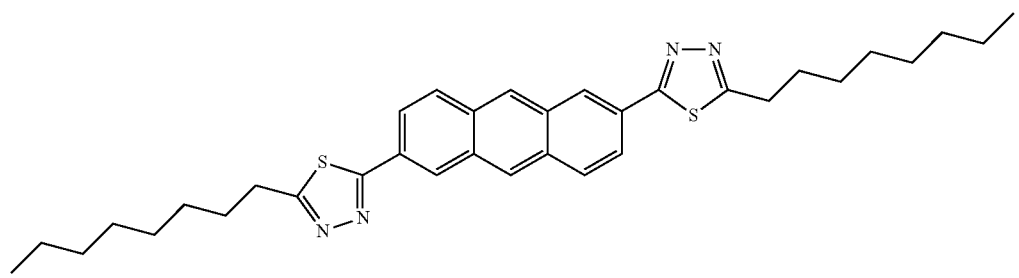
(No. 103)
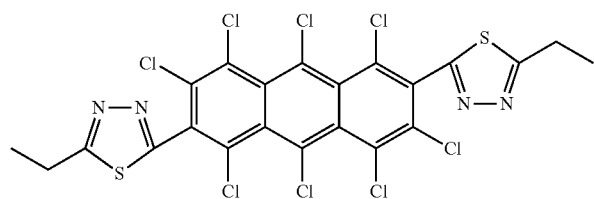
(No. 104)
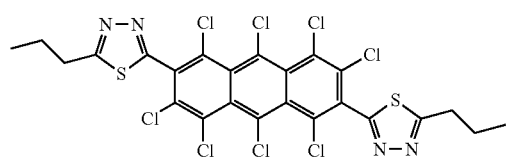
(No. 105)
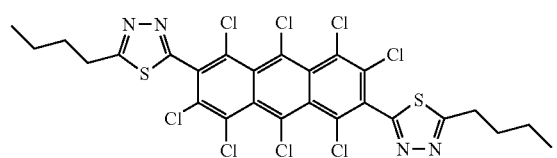
(No. 106)
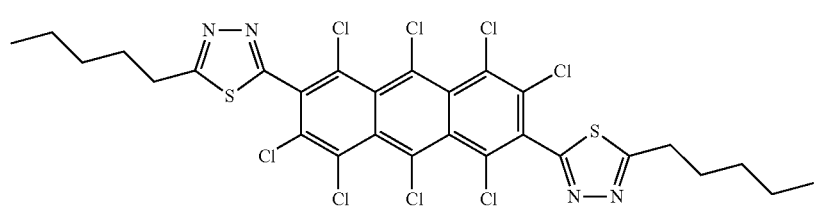

-continued
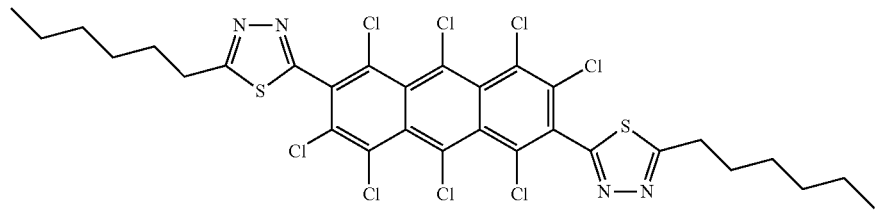
(No. 107)
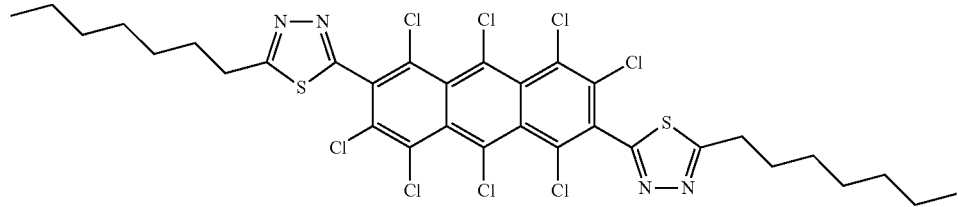
(No. 108)
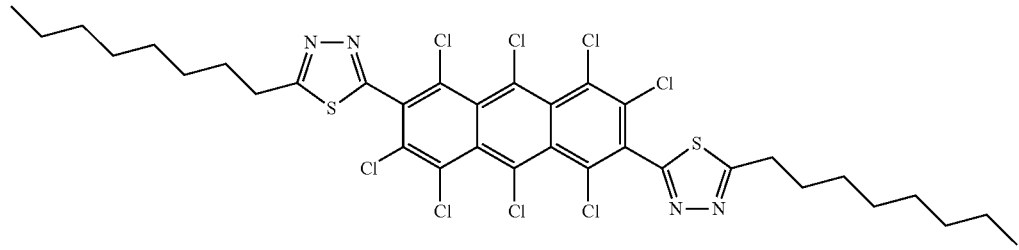
(No. 109)
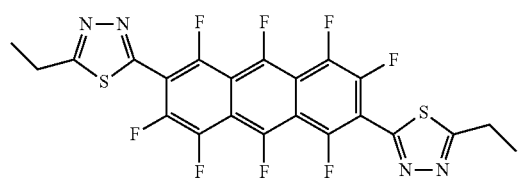
(No. 110)
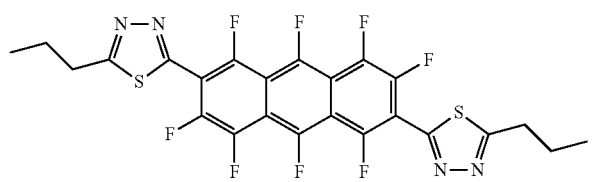
(No. 111)
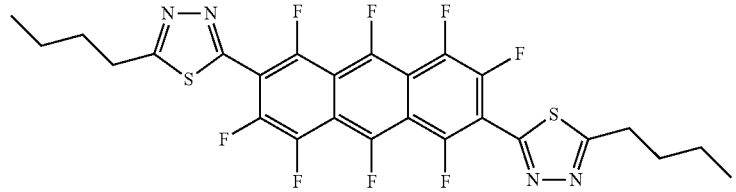
(No. 112)
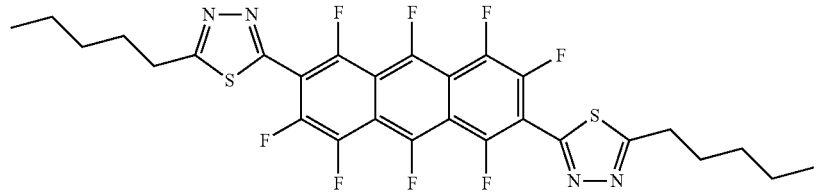
(No. 113)
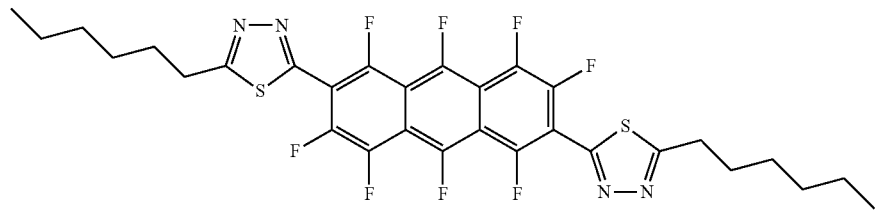
(No. 114)

-continued
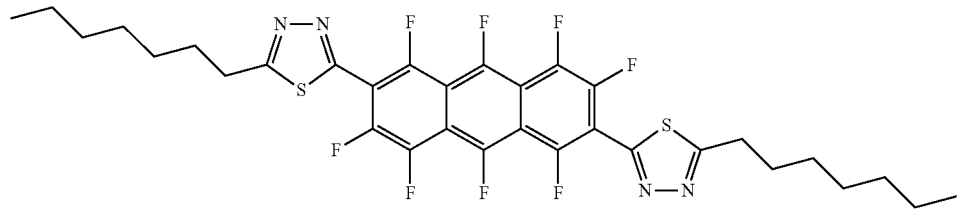
(No. 115)
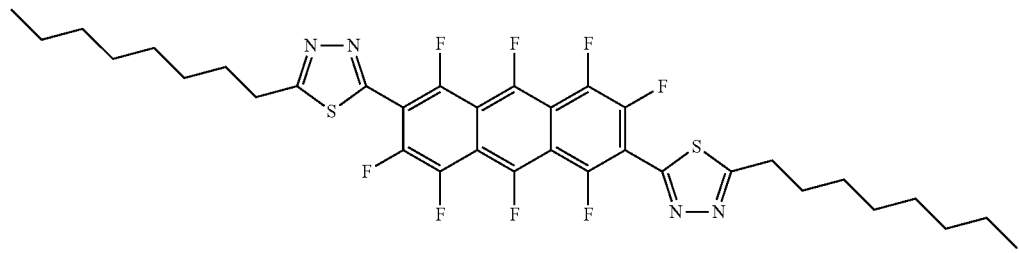
(No. 116)
(No. 117)
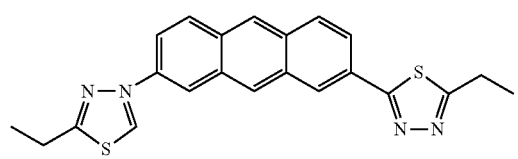
(No. 118)
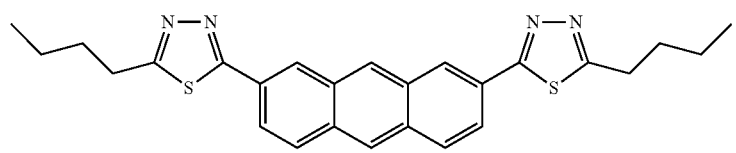
(No. 119)
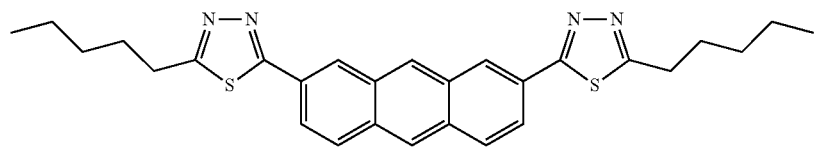
(No. 120)
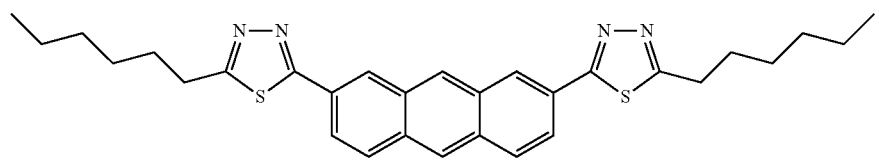
(No. 121)
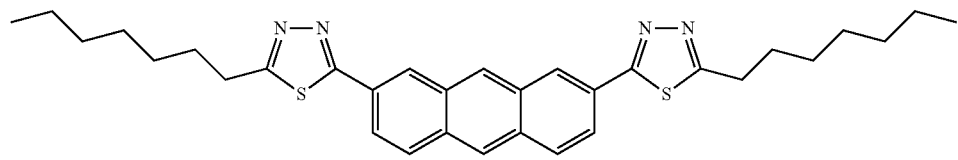
(No. 122)
(No. 123)
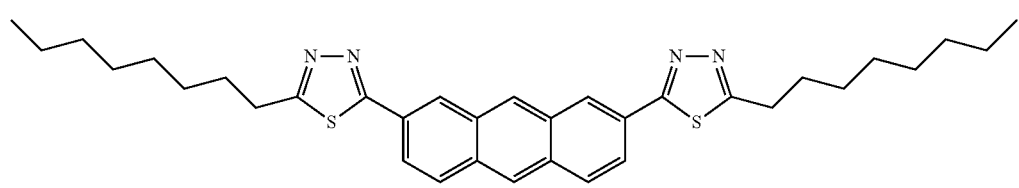

-continued
(No. 124)
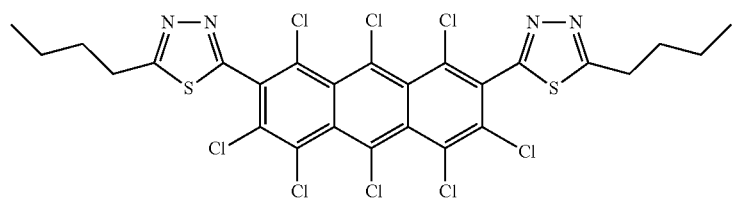
(No. 125)
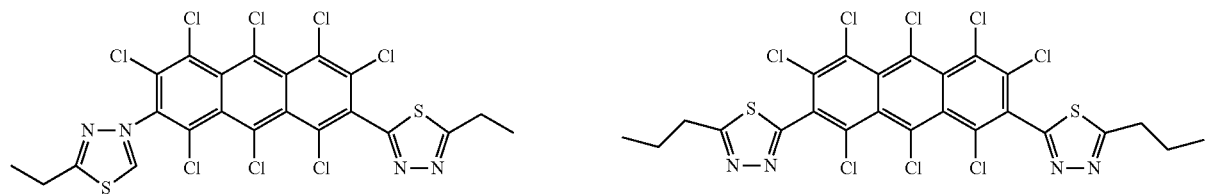
(No. 126)
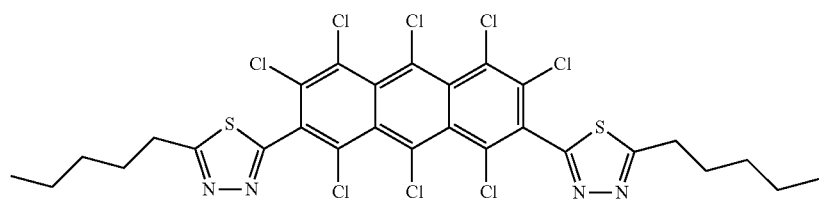
(No. 127)
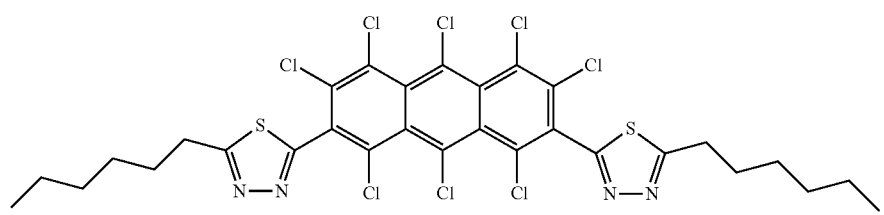
(No. 128)
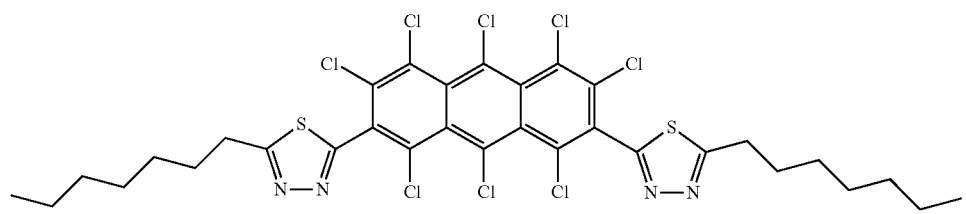
(No. 129)
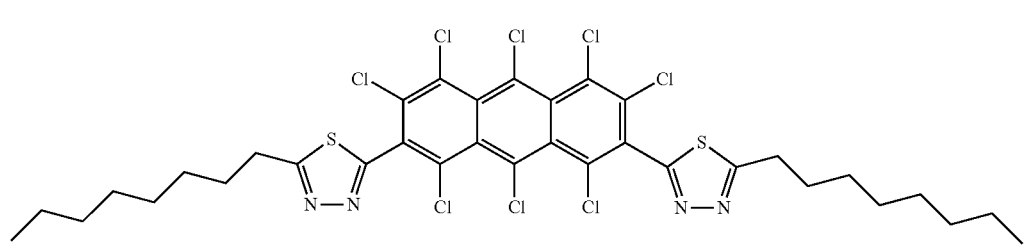
(No. 130)
(No. 131)
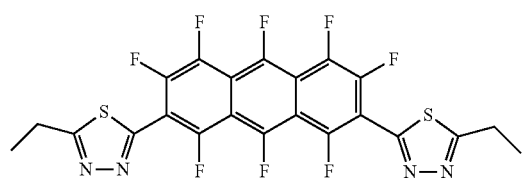
(No. 132)
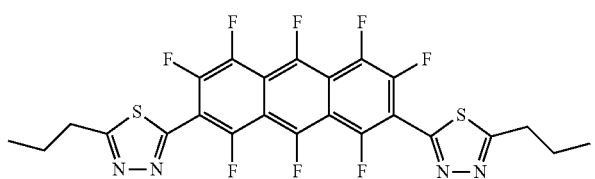

-continued
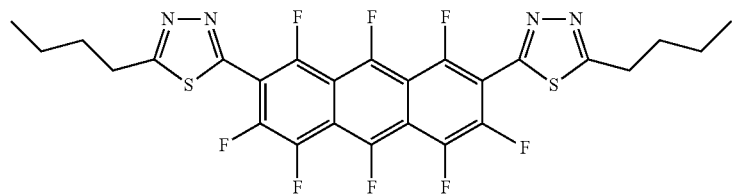
(No. 133)
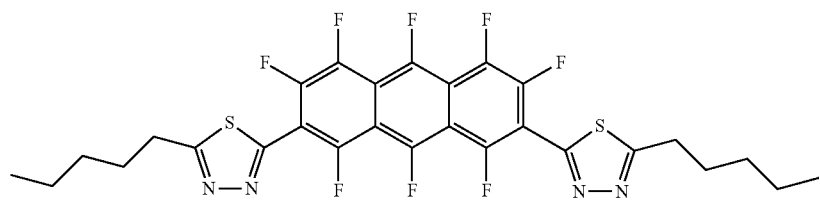
(No. 134)
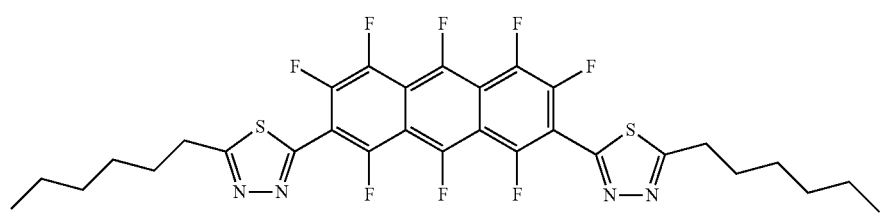
(No. 135)
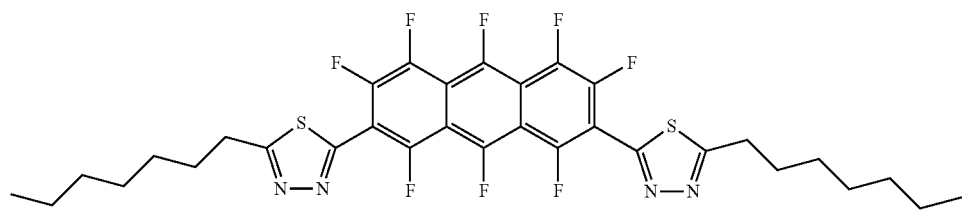
(No. 136)
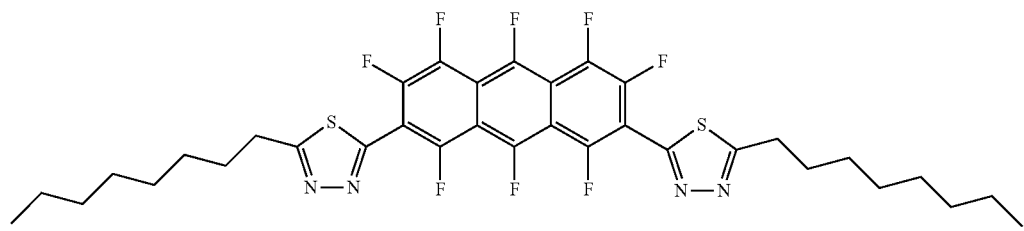
(No. 137)
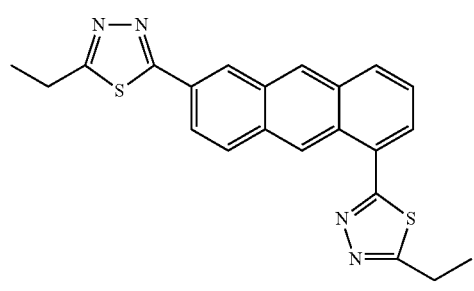
(No. 138)
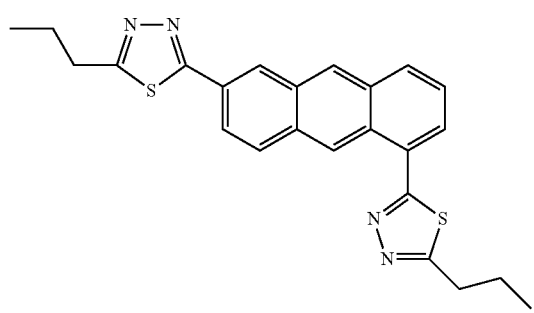
(No. 139)

-continued
(No. 140)
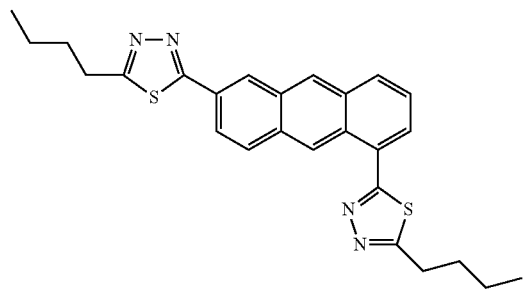
(No. 141)
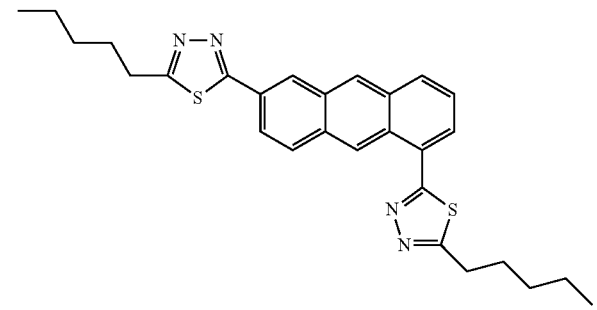
(No. 142)
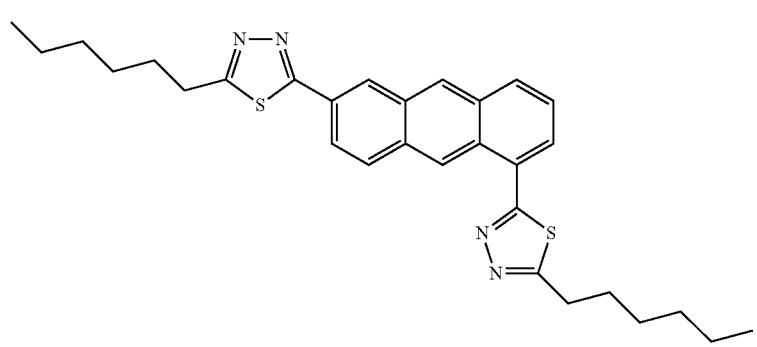
(No. 143)
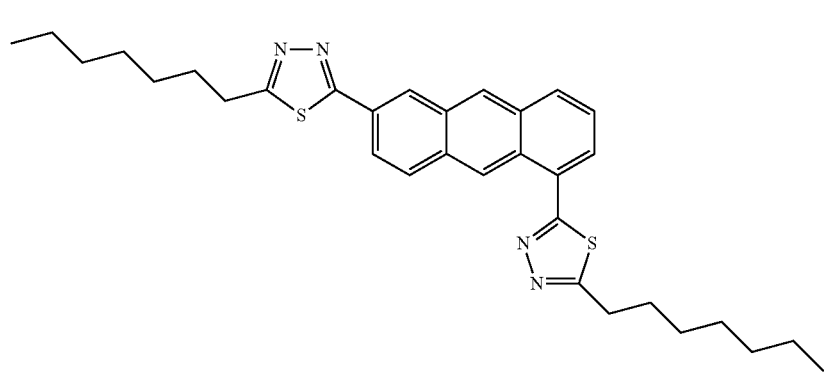
(No. 144)
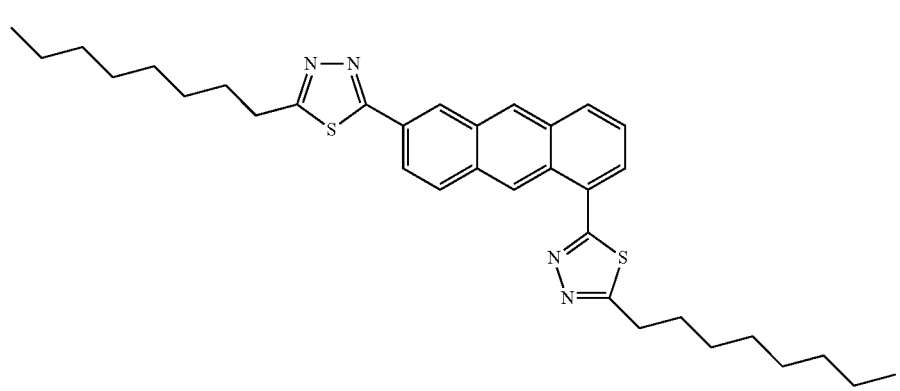

-continued
(No. 145)
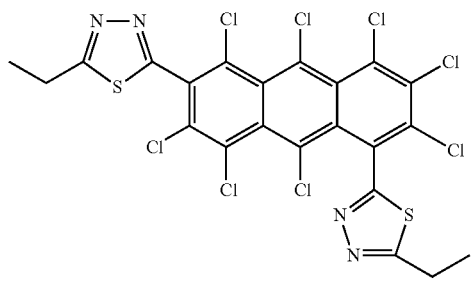
(No. 146)
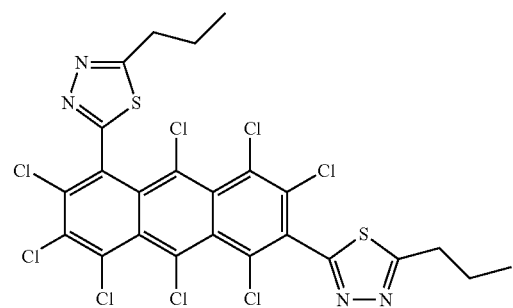
(No. 147)
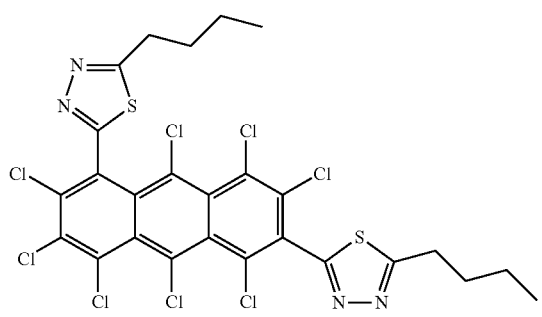
(No. 148)
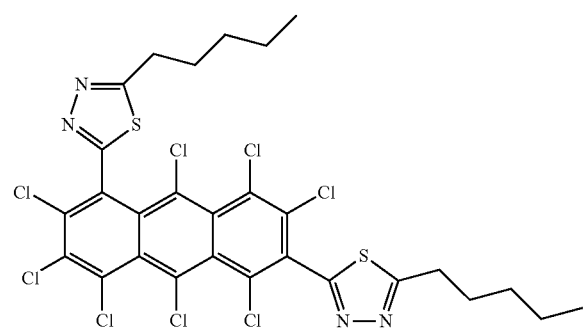
(No. 149)
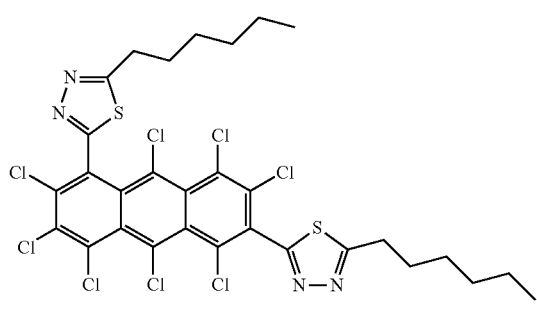
(No. 150)
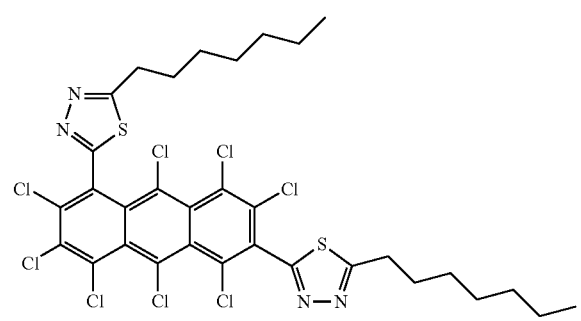
(No. 151)
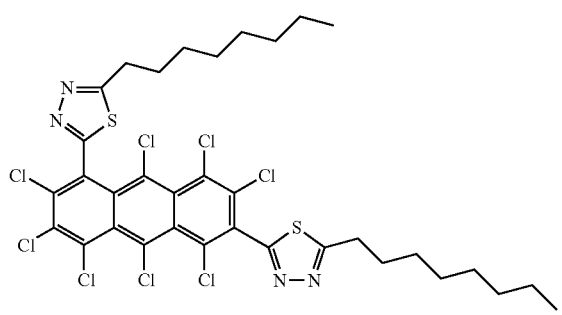
(No. 152)
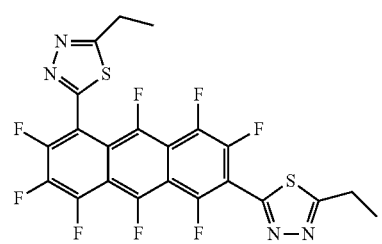

-continued
(No. 153)
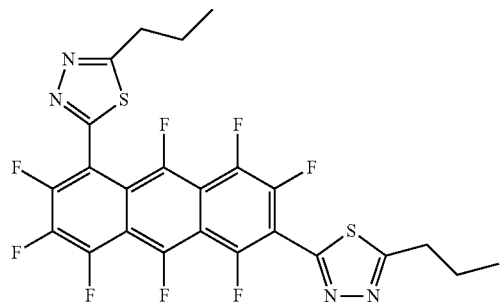
(No. 154)
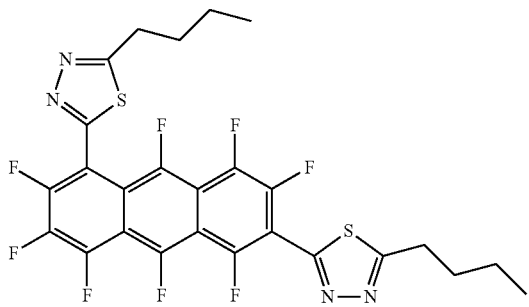
(No. 155)
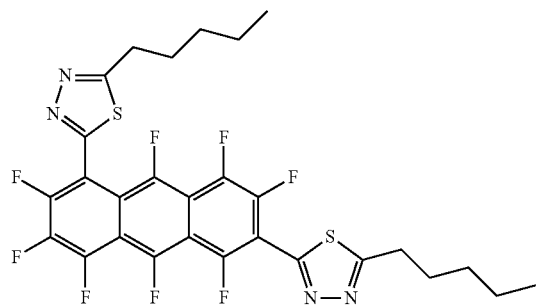
(No. 156)
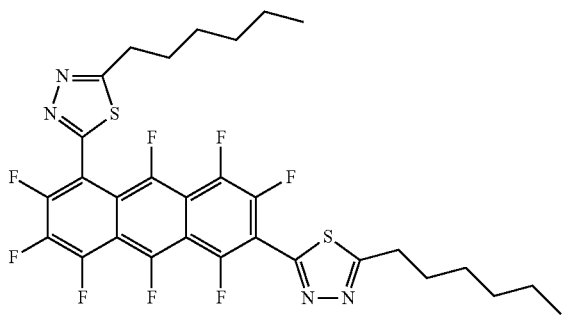
(No. 157)
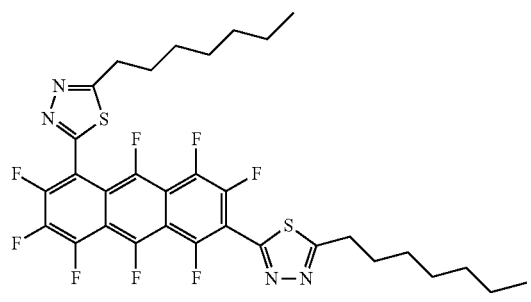
(No. 158)
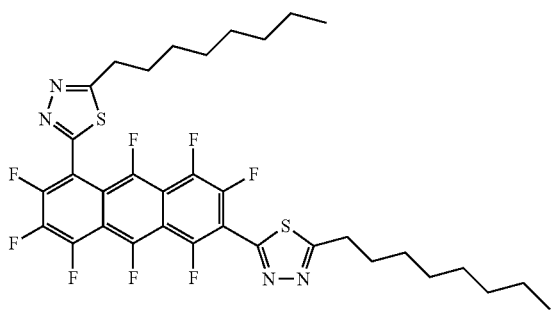
(No. 159)
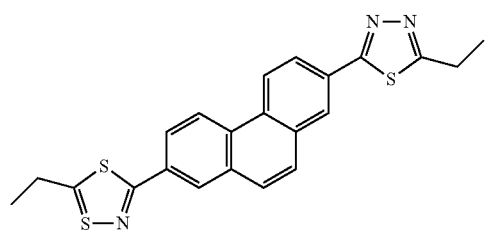
(No. 160)
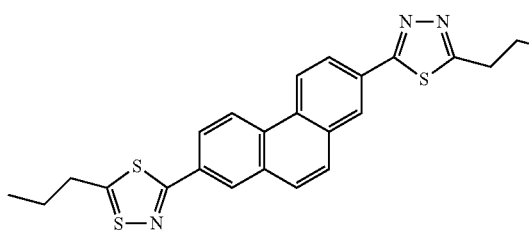
(No. 161)
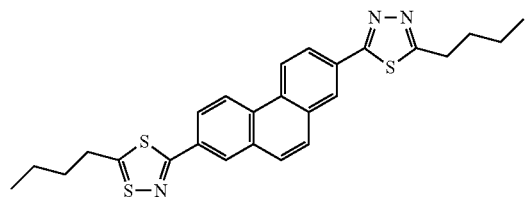
(No. 162)
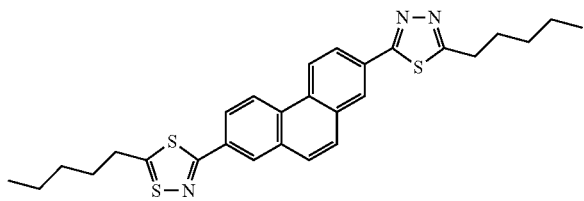

(No. 163)
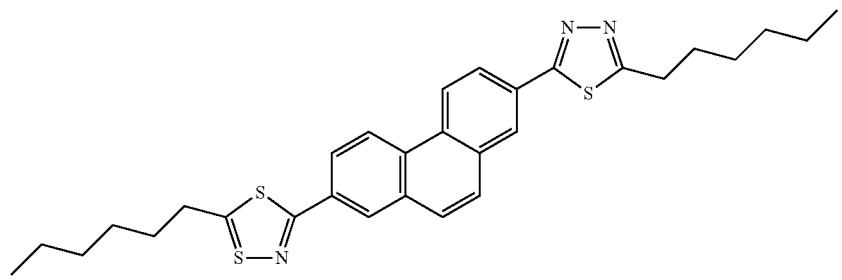
(No. 164)
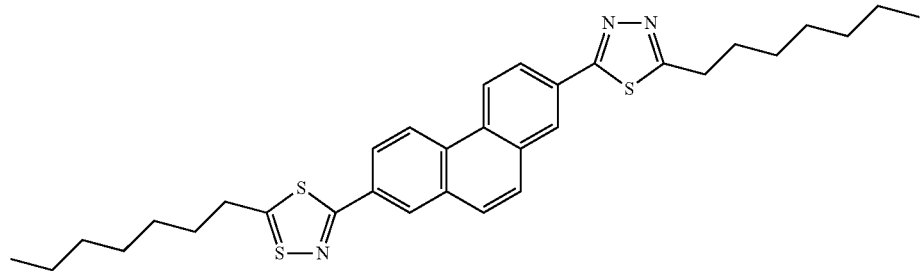
(No. 165)
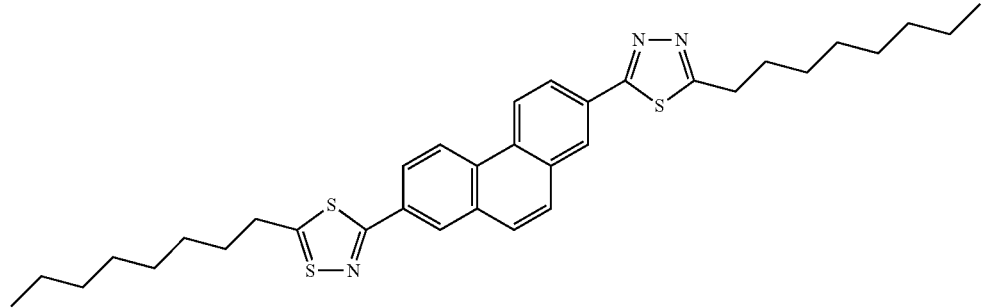
(No. 166)
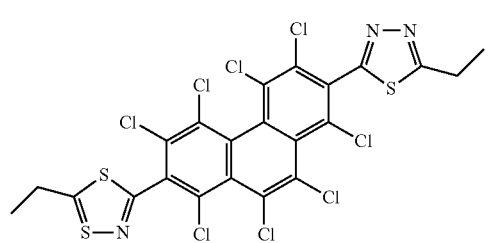
(No. 167)
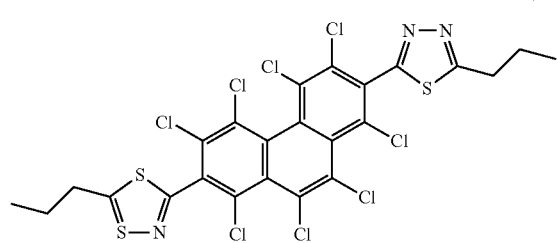
(No. 168)
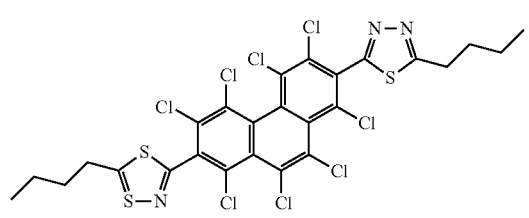
(No. 169)
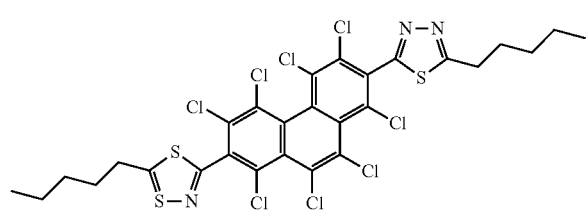
(No. 170)
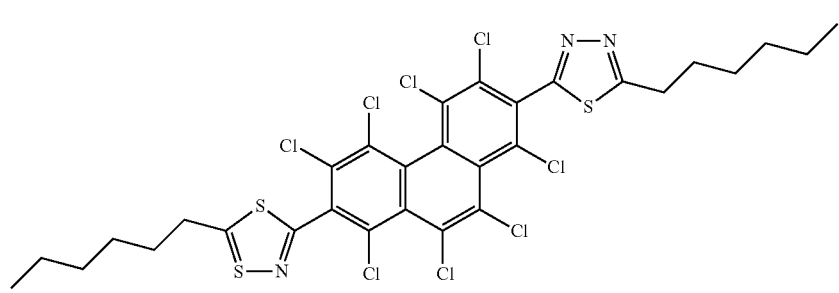

(No. 171)
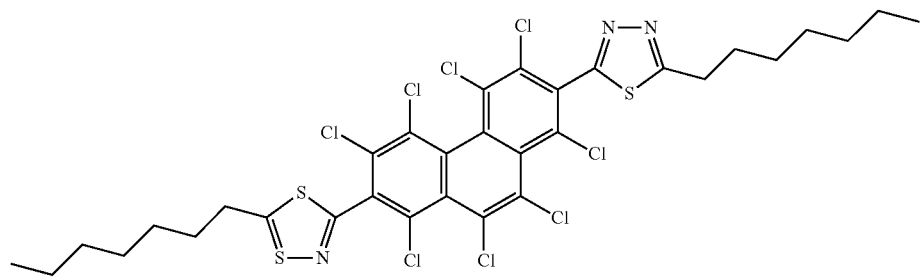
(No. 172)
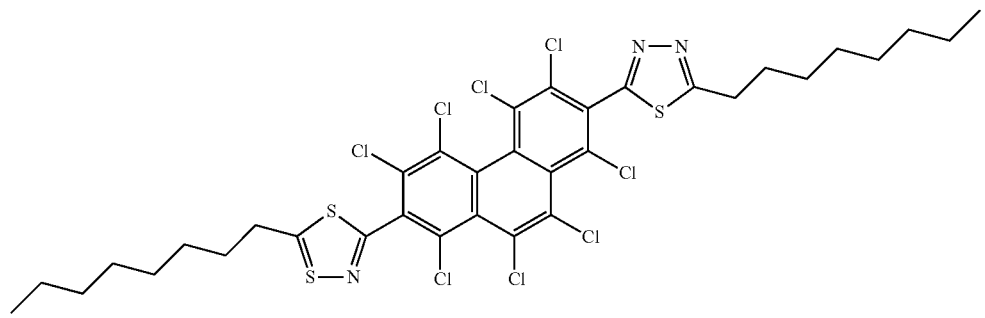
(No. 173)
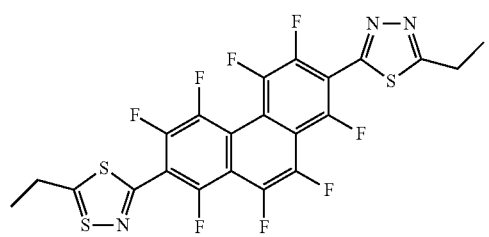
(No. 174)
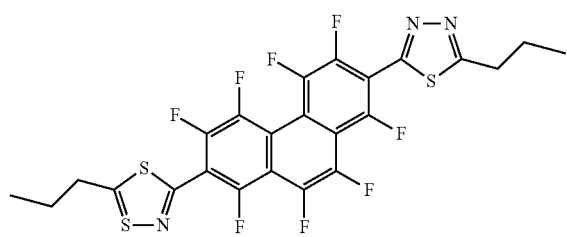
(No. 175)
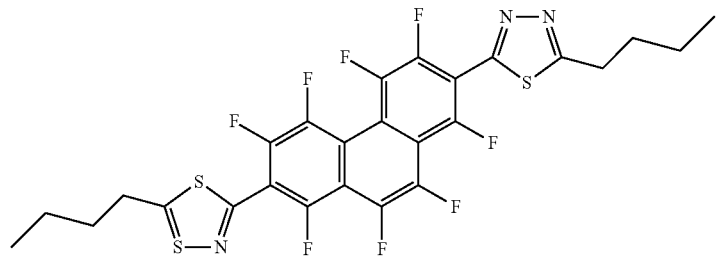
(No. 176)
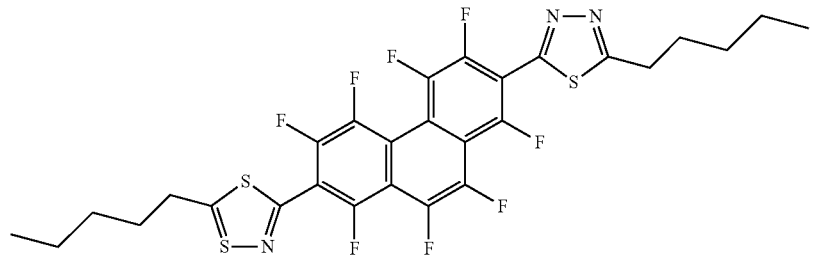
(No. 177)
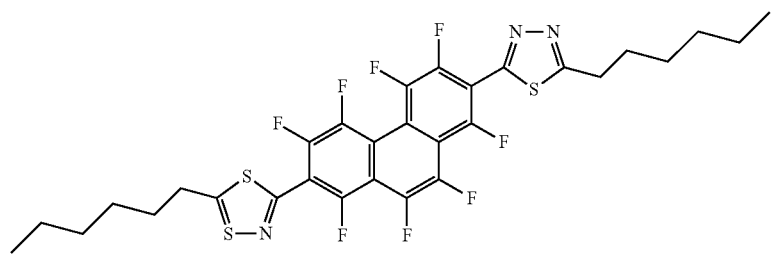

-continued
(No. 178)
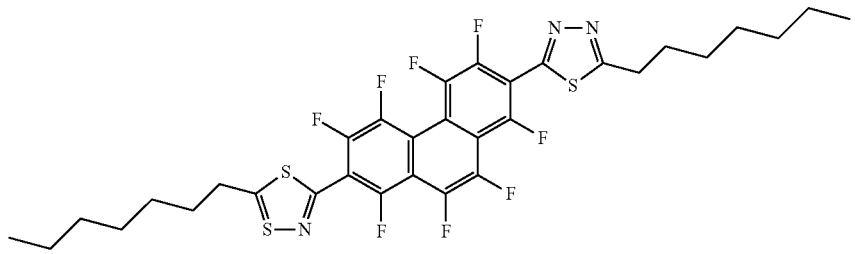
(No. 179)
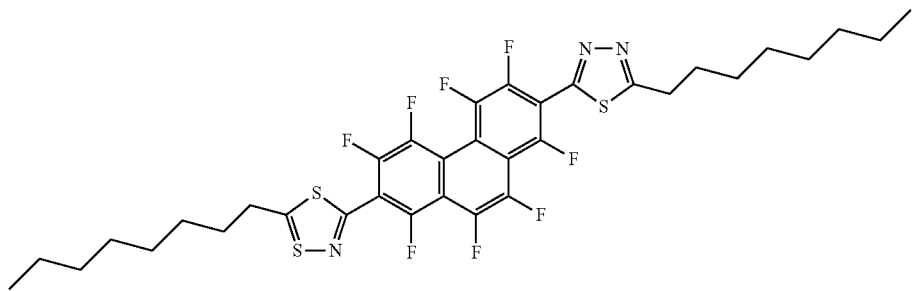
(No. 180)
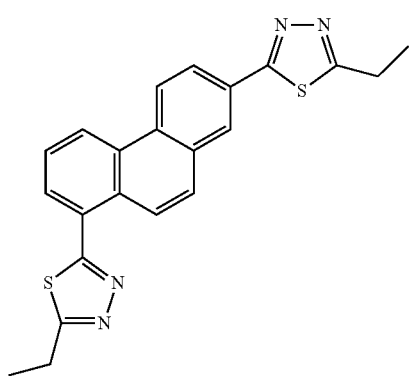
(No. 181)
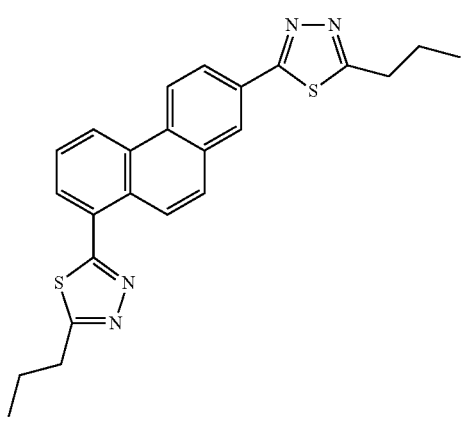
(No. 182)
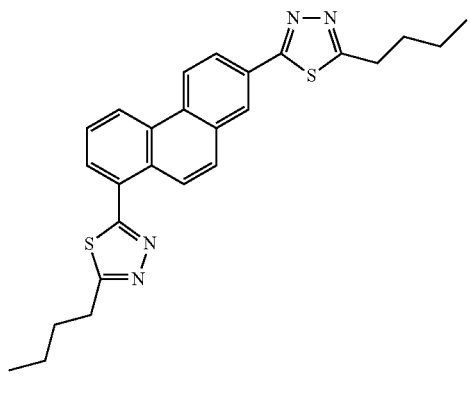
(No. 183)
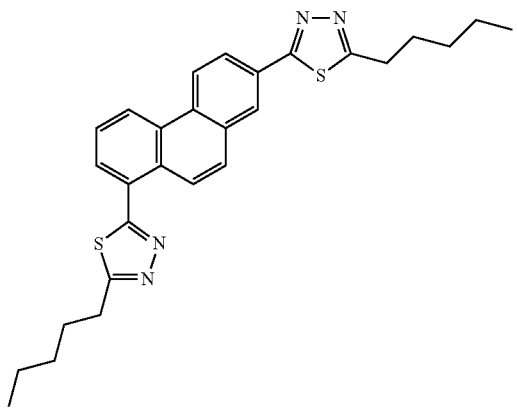

-continued
(No. 184)
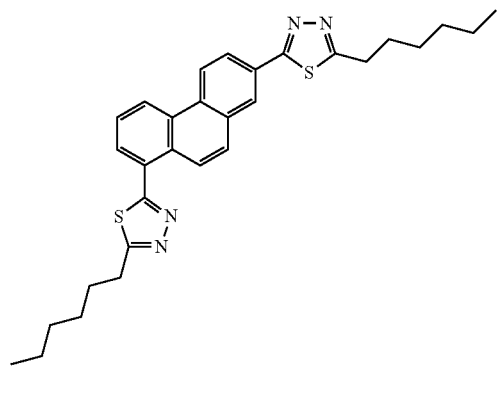
(No. 185)
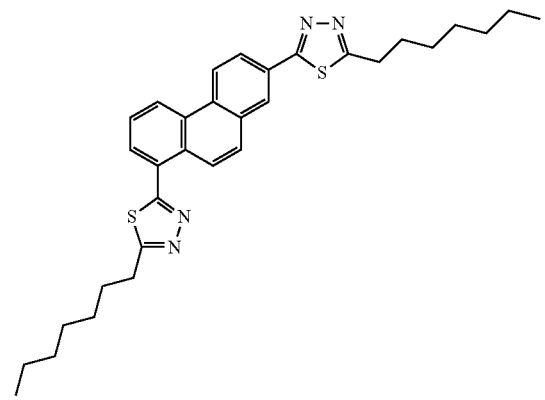
(No. 186)
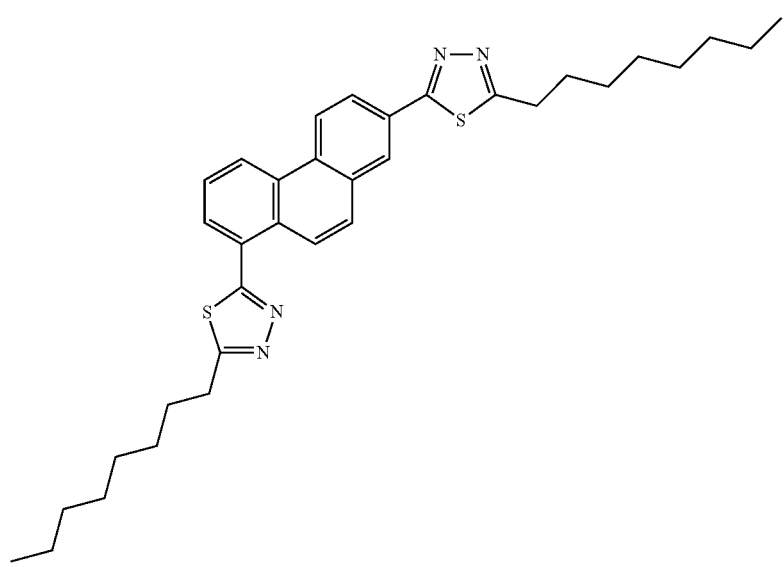
(No. 187)
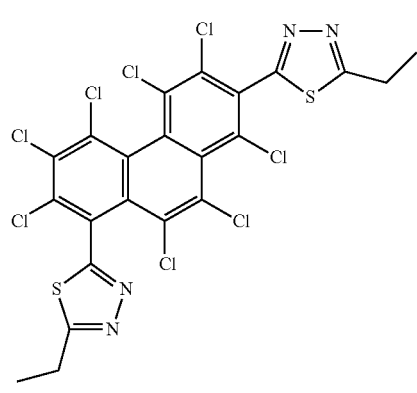
(No. 188)
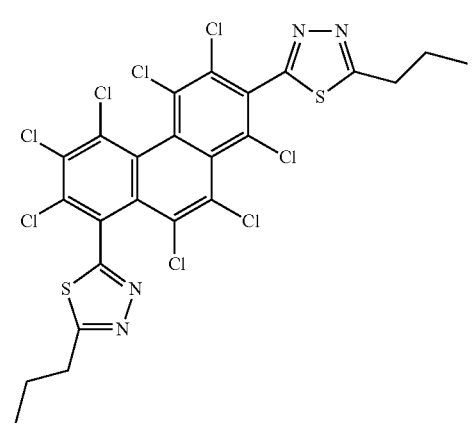

-continued
(No. 189)
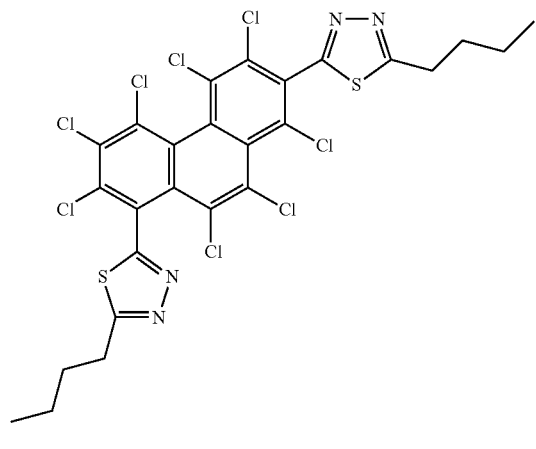
(No. 190)
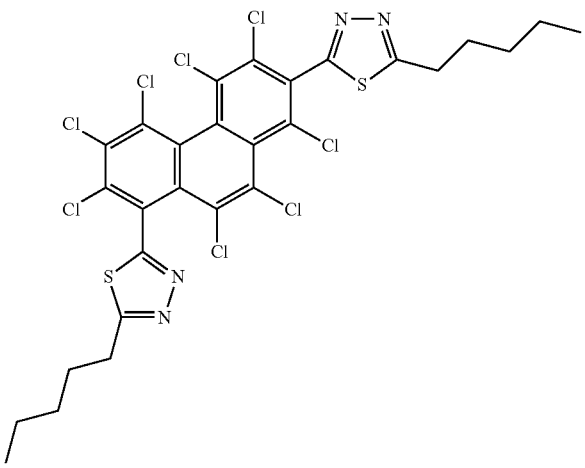
(No. 191)
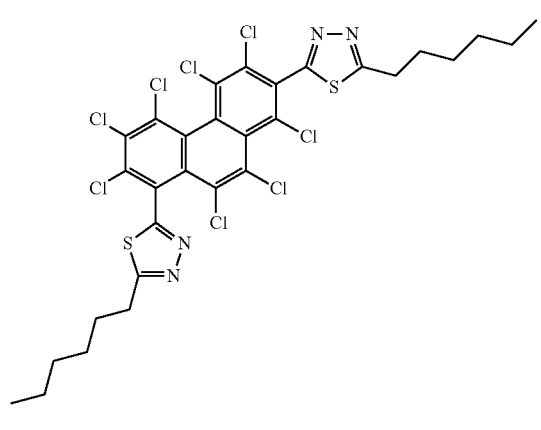
(No. 192)
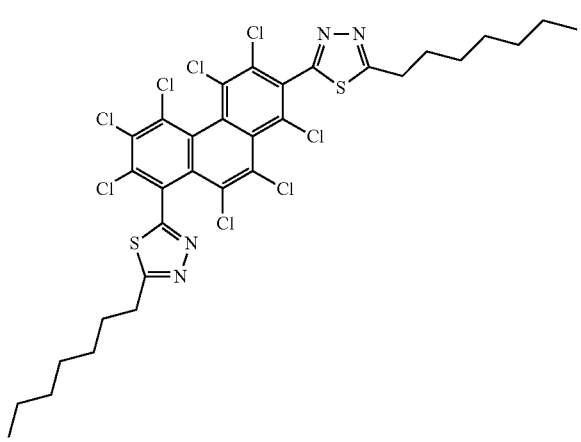
(No. 193)
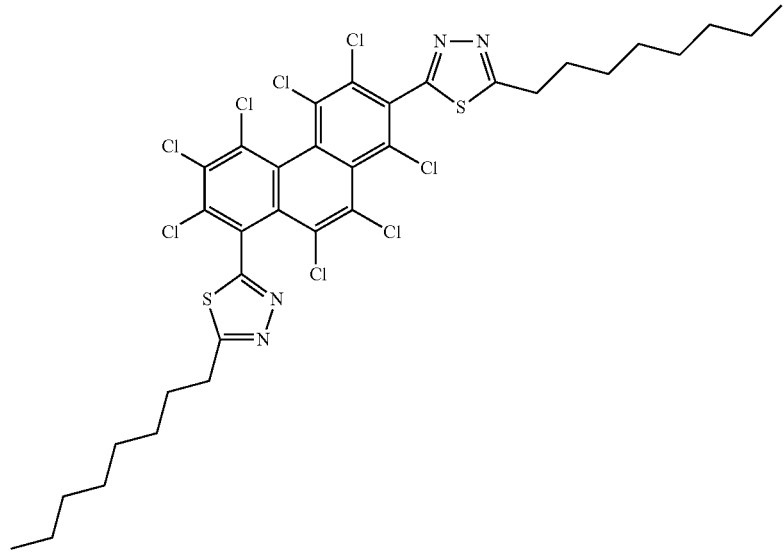

-continued
(No. 194)
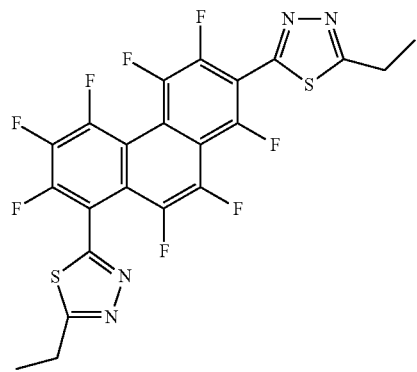
(No. 195)
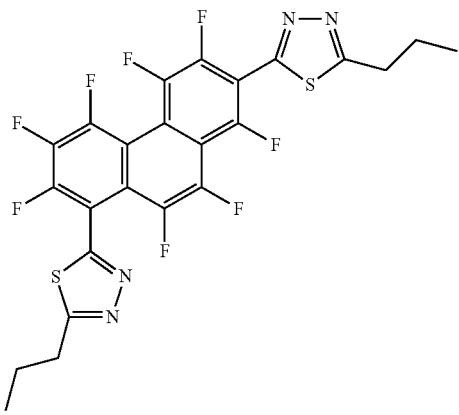
(No. 196)
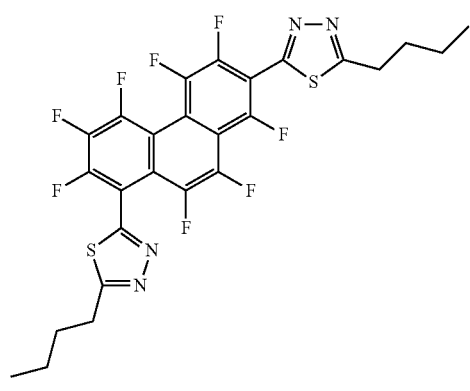
(No. 197)
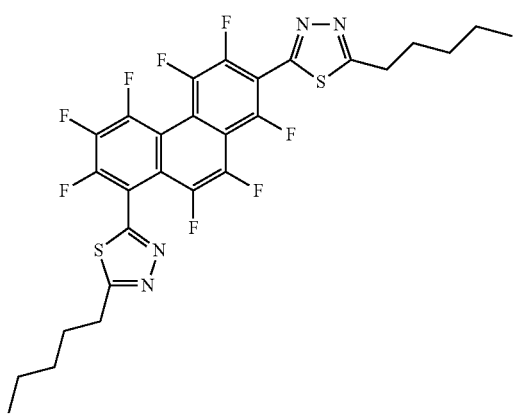
(No. 198)
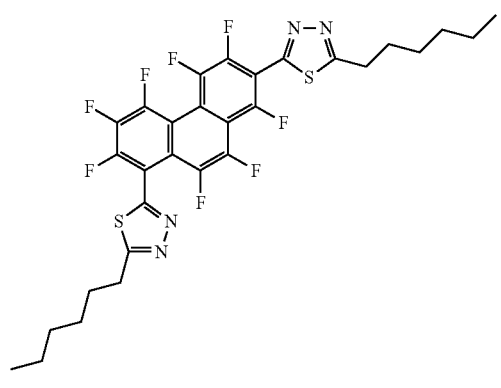
(No. 199)
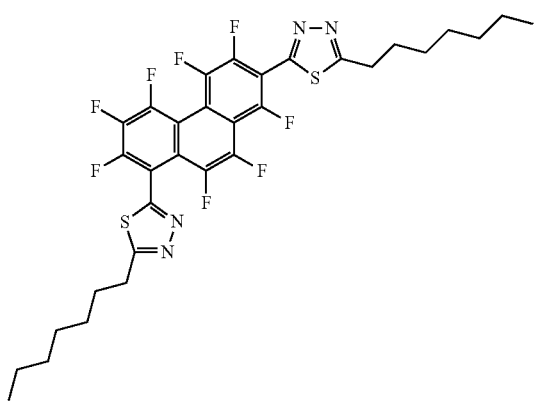

-continued
(No. 200)
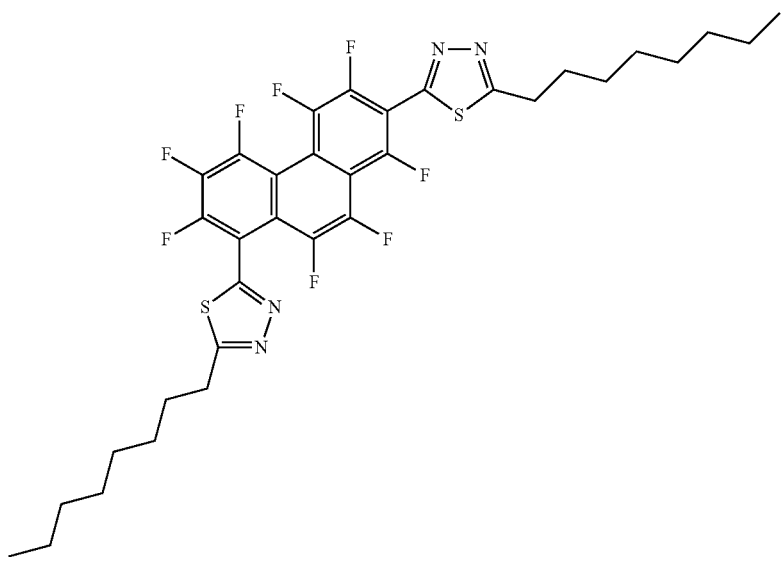
(No. 201)
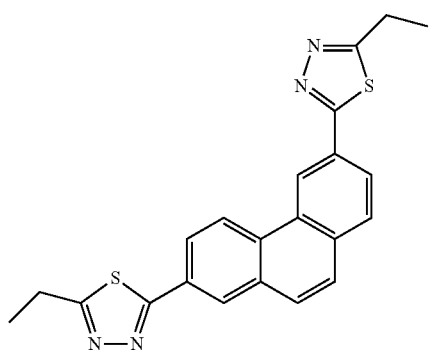
(No. 202)
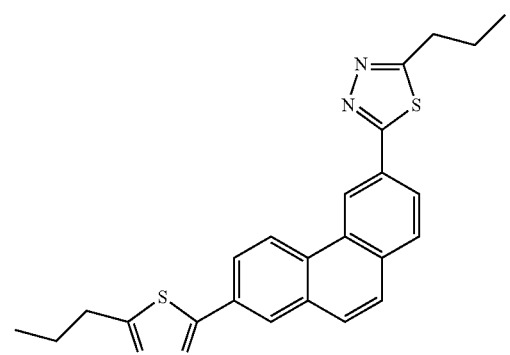
(No. 203)
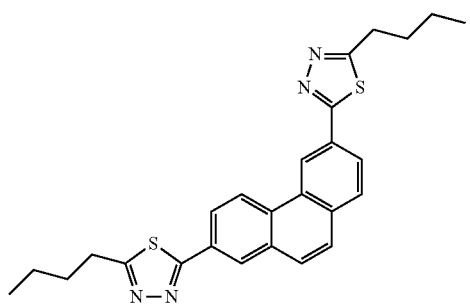
(No. 204)
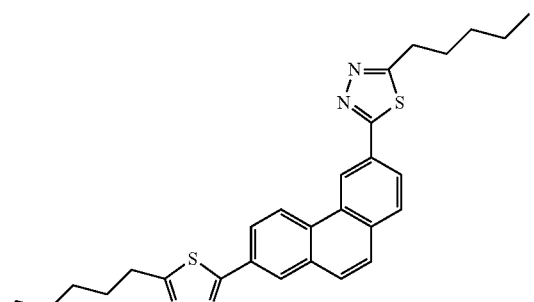
(No. 205)
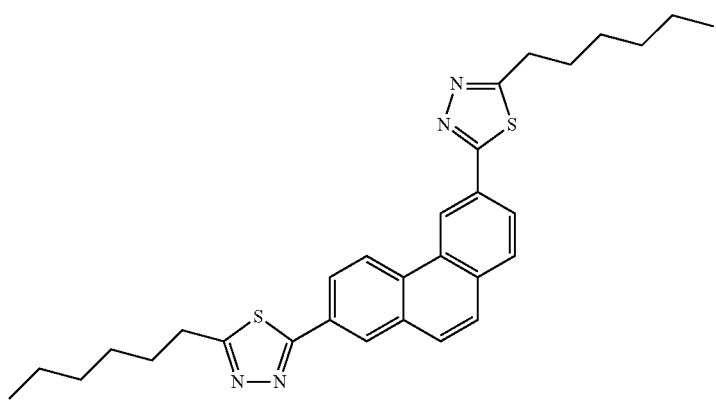

(No. 206)
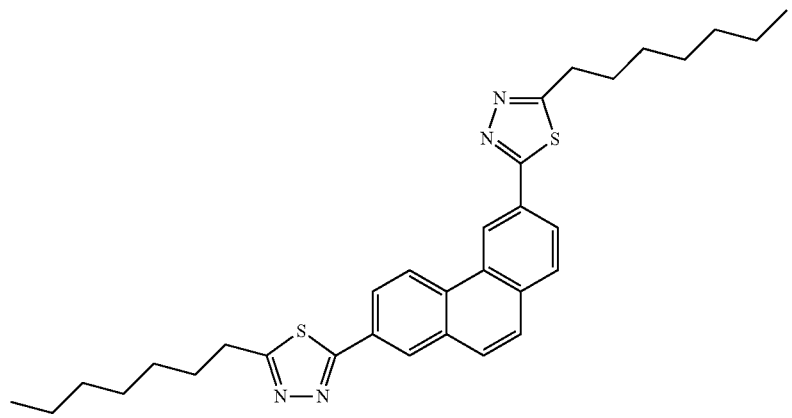
(No. 207)
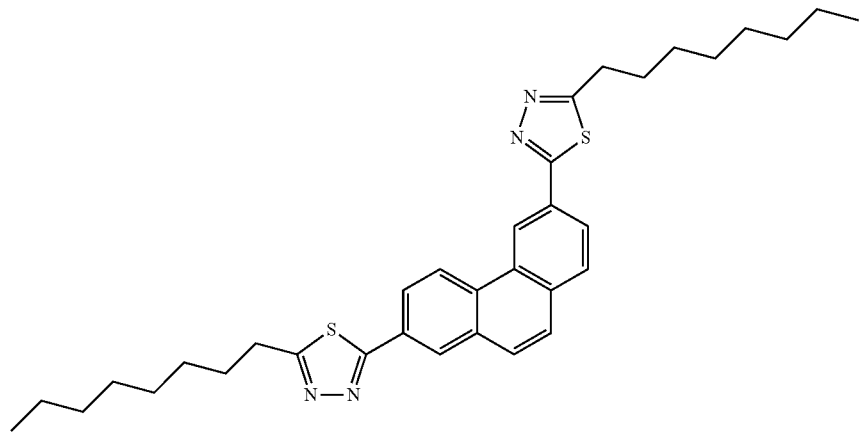
(No. 208)
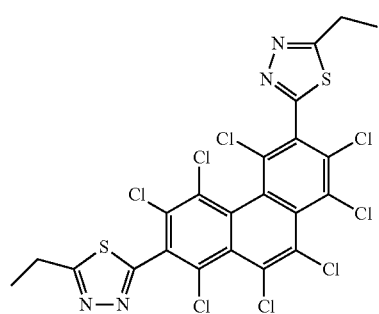
(No. 209)
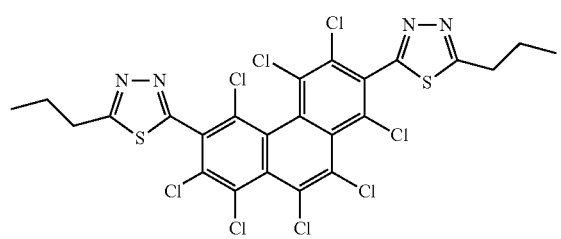
(No. 210)
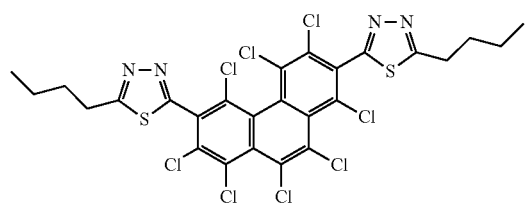
(No. 211)
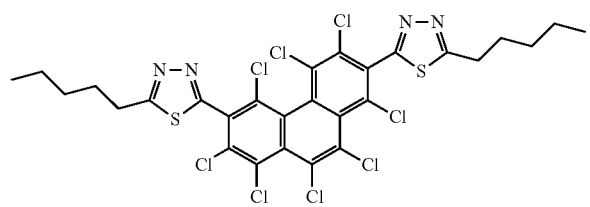

-continued
(No. 212)
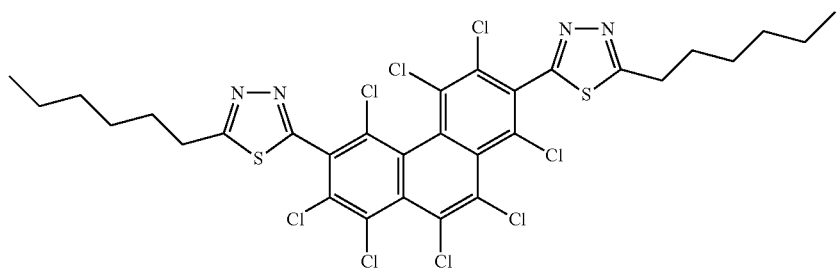
(No. 213)
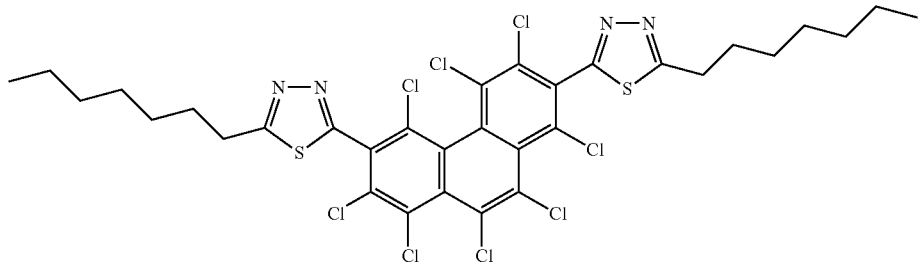
(No. 214)
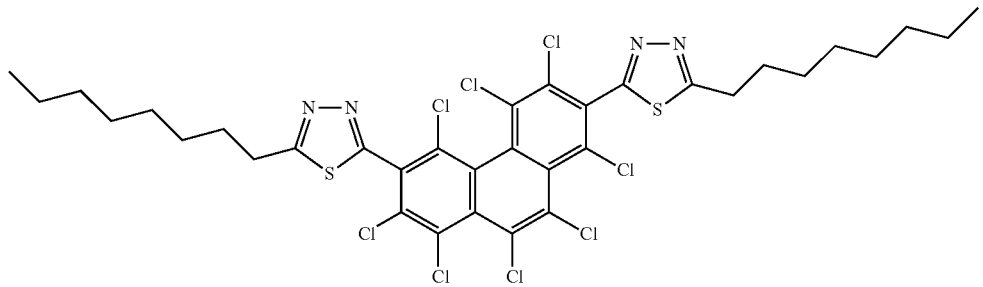
(No. 215) 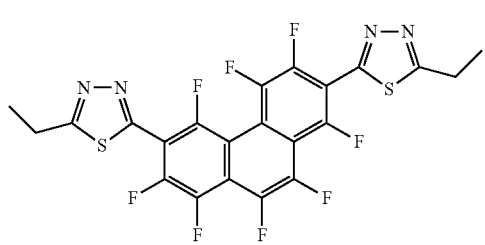 (No. 216) 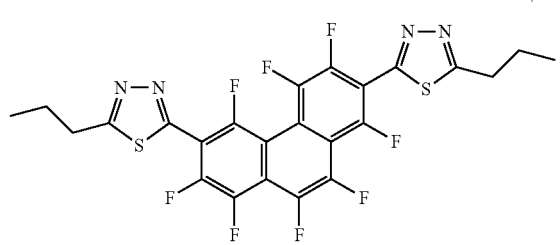
(No. 217) 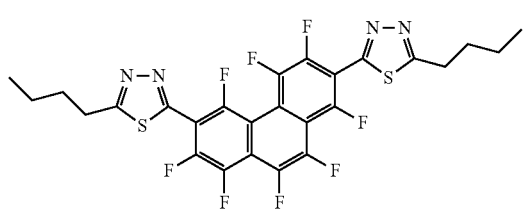 (No. 218)
(No. 219)
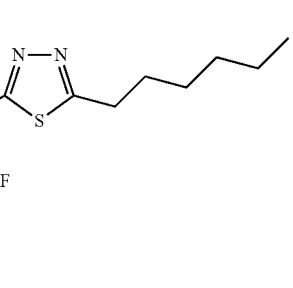

-continued
(No. 220)
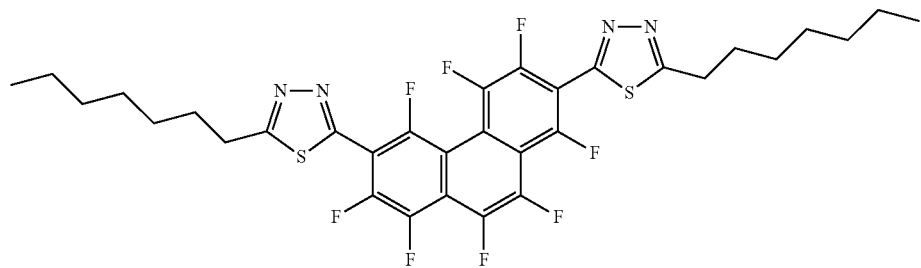
(No. 221)
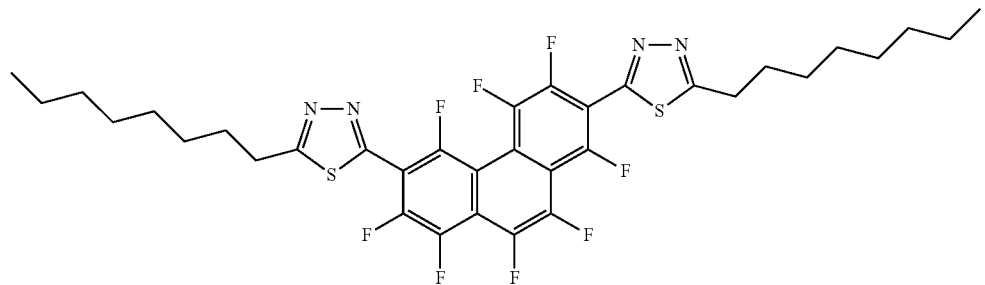
(No. 222) (No. 223)
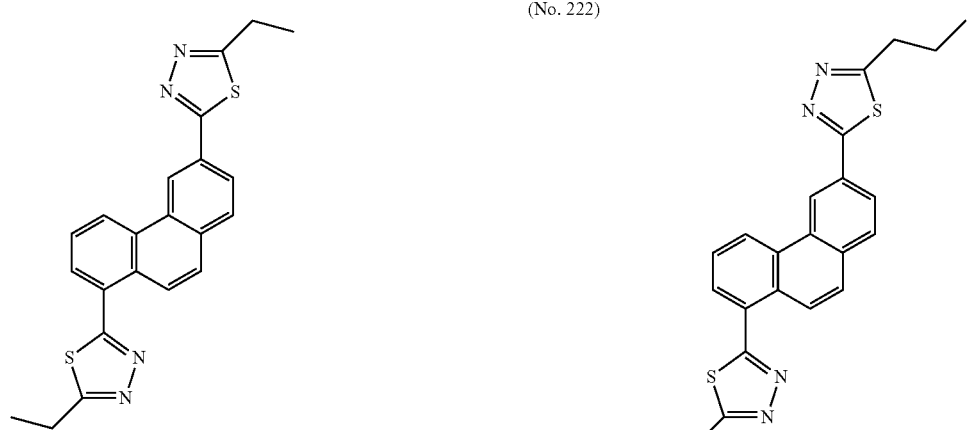
(No. 224) (No. 225)
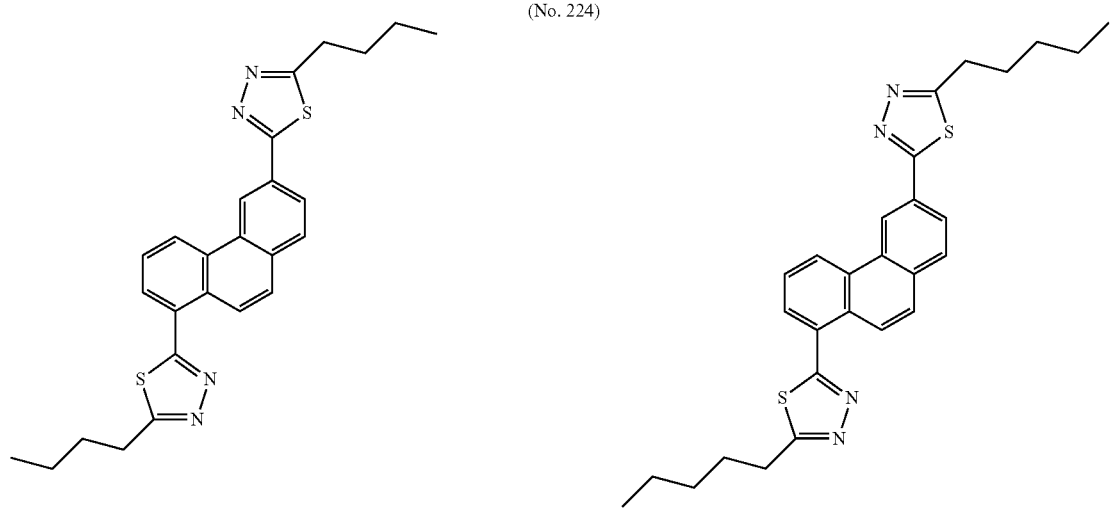

(No. 226)
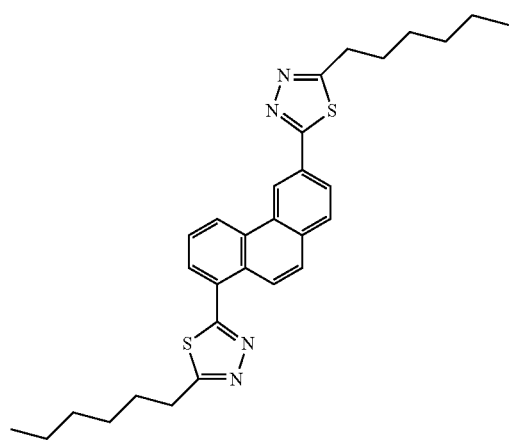
(No. 227)
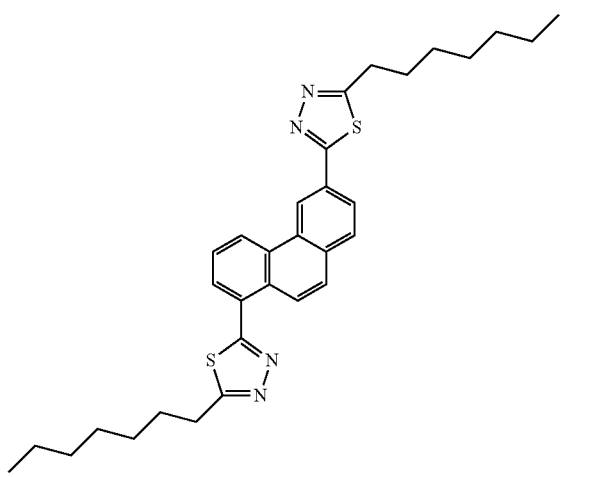
(No. 228)
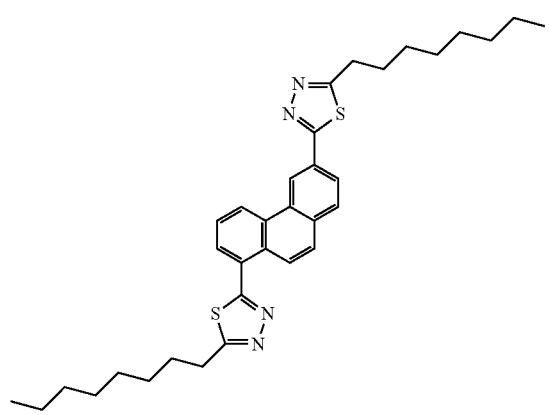
(No. 229)
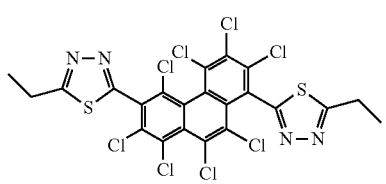
(No. 230)
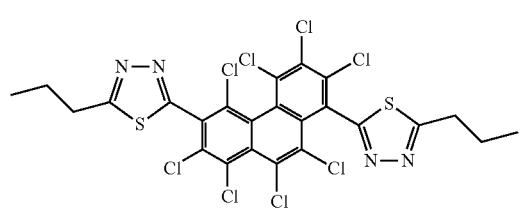
(No. 231)
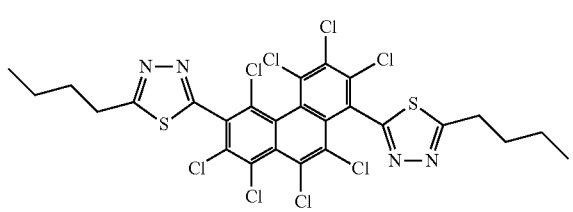
(No. 232)
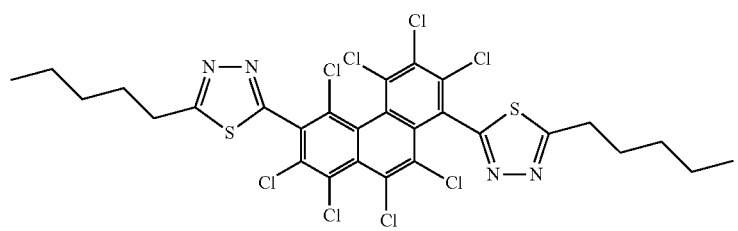
(No. 233)
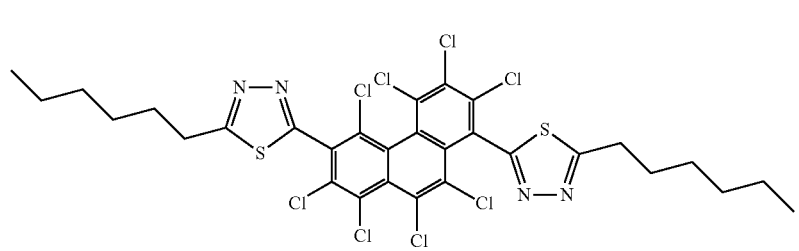

(No. 234)
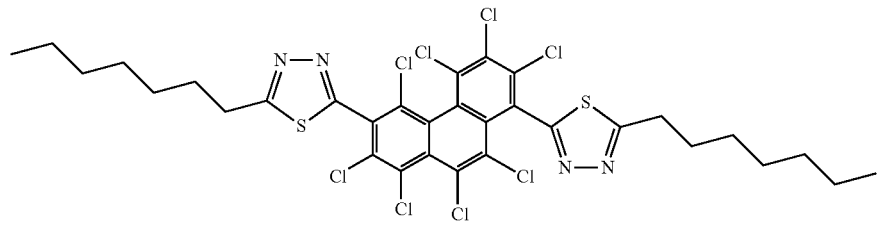
(No. 235)
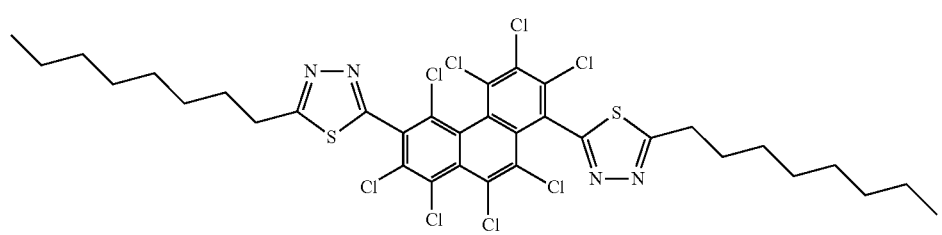
(No. 236)
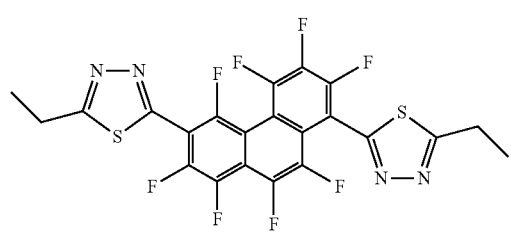
(No. 237)
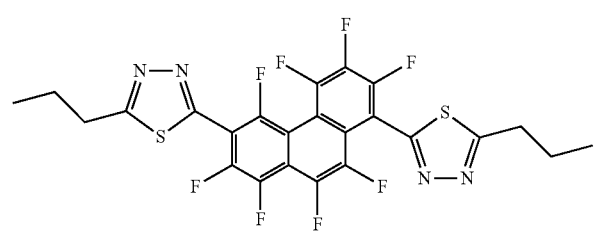
(No. 238)
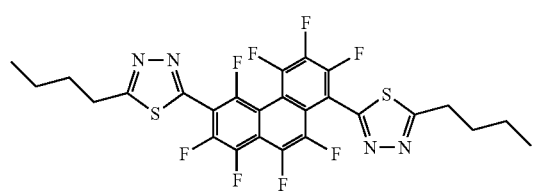
(No. 239)
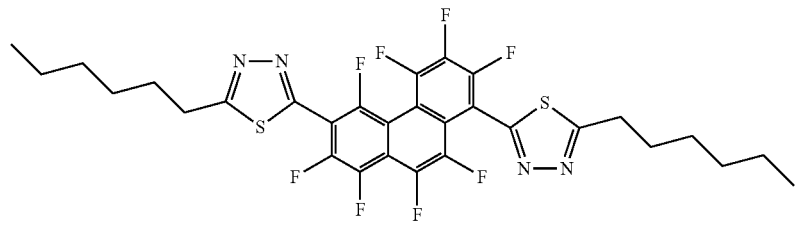
(No. 240)
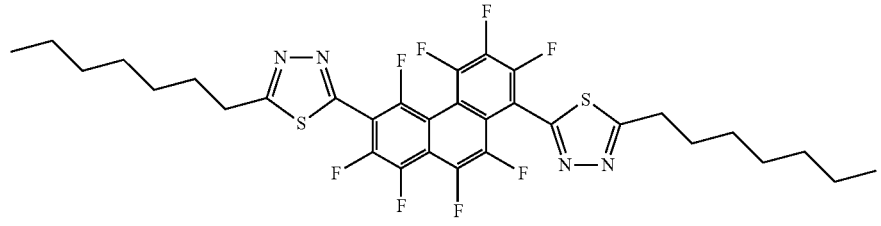
(No. 241)
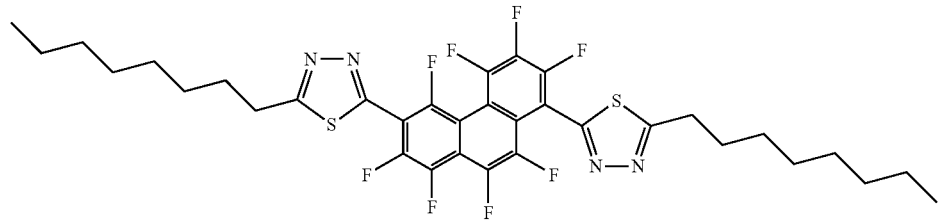
(No. 242)

<<Composition for Organic Semiconductor>>

The composition for organic semiconductor of the invention contains at least one or more types of the above compound (2), preferably for the composition for organic semiconductor of 100% by weight in an amount falling within a range of from 0.01% by weight to 100% by weight, more preferably from 1% by weight to 80% by weight.

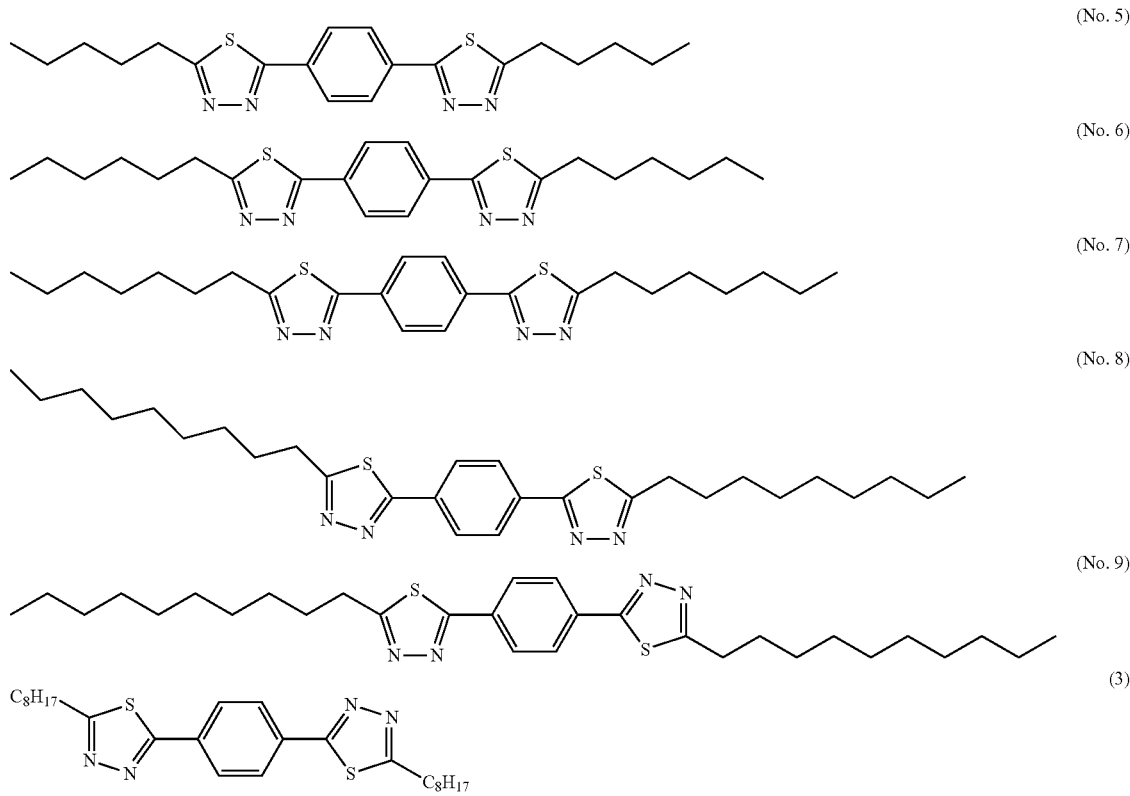

(No. 5)

(No. 6)

(No. 7)

(No. 8)

(No. 9)

(3)

The composition for organic semiconductor can be favorably used in the organic semiconductor film and the organic semiconductor device of the invention mentioned below.

The composition for organic semiconductor of the invention may consist essentially of the compound (2), to which, if desired, solvent and various additives may be added within a range not detracting from the advantage of the invention. Various additives include antioxidant, light stabilizer, surfactant, storage stabilizer, lubricant, antiaging agent, wettability improver, etc. However, it is considered that there is a high possibility that these various additives would have some negative influences on the carrier transport characteristics of the composition, and therefore, the composition for organic semiconductor of the invention preferably consists essentially of the compound (2), or a mixture of the compound (2) and a solvent.

As R in the formula (2), there may be mentioned the same groups as those concretely mentioned for R in the formula (1); and preferred groups of R in the formula (2) may be the same as those of R in the formula (1).

Ar in the formula (2) is phenylene, naphthylene, anthrylene or phenanthrylene, preferably, phenylene, naphthylene or anthrylene, more preferably phenylene or naphthylene.

Any hydrogen in these rings may be replaced by halogen. In case where any hydrogen is replaced by halogen, preferably every hydrogen in these rings is replaced by halogen. As the halogen, preferred are fluorine and chlorine from the viewpoint of the carrier mobility and the heat stability, and more preferred is fluorine.

When Ar in the formula (2) is phenylene, the compound (2) tends to exhibit excellent hole and electron-transport characteristics. Examples of the compounds of the formula (2) where Ar is phenylene are shown below.

Examples of phenylene in which any hydrogen is replaced by halogen include 2-fluoro-1,4-phenylene, 2,3-difluoro-1,4-phenylene, 2,5-difluoro-1,4-phenylene, 2,3,5-trifluoro-1,4-phenylene, 2,3,5,6-tetrafluoro-1,4-phenylene. Of those, preferred is 2,3,5,6-tetrafluoro-1,4-phenylene.

Compounds of the above formula (2) where Ar is phenylene in which any hydrogen may be replaced by halogen tends to come to have larger electron mobility than a compound (1), and the other characteristics exhibit a similar effect. But when it is replaced some hydrogen by halogen in a compound of the above formula (2) where Ar is phenylene, the compound has decreased symmetry properties of molecules, and crystalline tend to decrease. This effect may not increase the carrier mobility or may decrease the carrier mobility.

As examples of naphthylene, anthrylene and phenanthrylene in which any hydrogen is replaced by halogen, there are mentioned the same groups as those concretely mentioned for Ar in the formula (1), and preferred groups thereof are also the same as those for Ar in the formula (1).

The compound (2) may be produced in the similar method as that for the compound (1), which, however, is not limitative. Examples of the compound (2) to be produced according to the method include the same as those of the compound (1)

mentioned above. The structure of the compound (2) may be identified through proton NMR spectrometry.

Not specifically defined, solvent usable for the composition for organic semiconductor of the above may be any one capable of dissolving the compound (2).

The solvent of the type includes, for example, pentane, hexane, heptane, diethyl ether, t-butyl methyl ether, tetrahydrofuran, methanol, ethanol, 2-propanol, ethyl acetate, ethyl lactate, dioxane, benzene, toluene, xylene, dichloromethane, chloroform, acetonitrile, acetone, cyclohexane, cyclopentanone, cyclohexanone, γ-butyrolactone, butyl cellosolve, N-methyl-2-pyrrolidone, dimethylformamide, dimethyl sulfoxide, water, and their mixtures.

<<Liquid-Crystal Composition for Organic Semiconductor>>

The liquid-crystal composition for organic semiconductor (hereinafter this may be referred to as "composition having a liquid-crystal phase") of the invention comprises the above-mentioned composition for organic semiconductor of the invention having a smectic phase or a nematic phase.

The above liquid-crystal composition for organic semiconductor may consist essentially of the composition having a liquid-crystal phase, or may consist essentially of a mixture of the above liquid-crystal composition having a liquid-crystal phase and the above-mentioned composition for organic semiconductor of the invention not having a liquid-crystal phase. As necessary, various additives that are the same as those mentioned above may be added to the above liquid-crystal composition for organic semiconductor within a range not detracting from the advantage of the invention.

<<Organic Semiconductor Film>>

The organic semiconductor film of the invention is formed of the above-mentioned compound (1), the above-mentioned composition for organic semiconductor of the invention or the above-mentioned liquid-crystal composition for organic semiconductor of the invention. For this reason, the organic semiconductor film can transport an electron and a hole, and it is a visible light-transmissive semiconductor film having a low defect density.

Of the compound (1) and the compound (2), the clear point can be controlled in any desired manner, and the compounds have high solubility in organic solvents, for which, therefore, simple film formation methods such as a casting method, a printing method or the like may be employed. Accordingly, using the compounds (1) and (2), organic semiconductor films can be formed not detracting from the carrier mobility intrinsic to the compounds.

Accordingly, the above-mentioned organic semiconductor film is favorably used for the organic semiconductor devices below.

In case where an organic semiconductor film is formed of the compound (1), the composition for organic semiconductor, or the liquid-crystal composition for organic semiconductor, a molten liquid prepared by heating and melting the compound (1) or a solution of the compound (1) dissolved in a solvent may be used; in case where the composition for organic semiconductor or the liquid-crystal composition for organic semiconductor is a solution containing of a solvent, the solution may be used directly; a solution further added a solvent to the solvent to improve coating properties and print performance may be used; or a molten liquid prepared by heating and melting the composition for organic semiconductor or the liquid-crystal composition for organic semiconductor which does not contain a solvent may be used. The solvent include in the same solvent as mentioned above may be used the composition for organic semiconductor. The compound (1), the composition for organic semiconductor and the liquid-crystal composition for organic semiconductor extremely well dissolves in organic solvents, and thus may form high-concentration solutions.

Preferably, the molten liquid or the solution is applied or printed on a substrate to thereby form an organic semiconductor film thereon.

The concentration of the compound (1) or the compound (2) in the solution where a solvent is used is preferably from 0.1 to 30% by weight, more preferably from 10 to 30% by weight, even more preferably from 10 to 20% by weight.

When the concentration of the compound (1) or the compound (2) in the solution falls within the above range, then a thin film having an nm-order thickness may be readily formed, and an organic semiconductor film having a reduced defect density may be readily formed.

In case where an organic semiconductor film is formed by the use of a solvent, the formed film may tend to have defects when the solvent is removed and the semiconductor film is dried. In this case, preferably, the formed film is annealed from the viewpoint of obtaining a film having few defects.

Accordingly, in order to produce a film having a low defect density from the compound (1), the composition for organic semiconductor or the liquid-crystal composition for organic semiconductor, in a simplified manner, preferred is use of the molten liquid of the compound or the composition. In particular, forming an organic semiconductor film from the compound (1) having a liquid-crystal phase or from the liquid-crystal composition for organic semiconductor is especially preferable, because even when defects exist in the formed film, they may tend to be reduced owing to the crystallinity of the film.

Various types of substrates are usable here. Preferred are a glass substrate, a metal substrate of gold, copper, silver or the like, a crystalline silicon substrate, an amorphous silicon substrate, a triacetyl cellulose substrate, a norbornene substrate, a polyethylene terephthalate substrate, a polyester substrate, a polyvinyl substrate, a polypropylene substrate, a polyethylene substrate, etc.

Various methods may be mentioned for the coating method, including, for example, a spin coating method, a dip coating method, and a blade coating method.

For the printing method, for example, there may be mentioned various methods of screen printing, inkjet printing, mask printing, offset printing, planographic printing, intaglio printing, relief printing. In case where a molten liquid is used, the liquid may be enclosed in a narrow cell by utilizing a capillary phenomenon, for which, therefore, employable is a printing method by dropping through a nozzle. Of the above, preferred is inkjet printing with a printer in which a molten liquid is directly used as the ink, as being a simple method.

In case where the organic semiconductor film is used directly as apart of an organic semiconductor device, preferably, the organic semiconductor film is produced by pattern printing. In this case, more preferably, the high-concentration solution or molten liquid of the compound (1), or the composition for organic semiconductor, or the liquid-crystal composition for organic semiconductor is used. Using the high-concentration solution or molten liquid, inkjet printing, mask printing, screen printing or offset printing is employable. Producing the organic semiconductor film according to such a printing mode contributes toward simplifying circuits, improving production efficiency and reducing the cost and the weight of devices. Producing the organic semiconductor film according to printing does not require a process of heating or vacuum treatment and can operate in an assembly-line, therefore contributing more to dealing with production cost reduction and process modification.

The thickness of the organic semiconductor film may be determined to any desired purpose, and is generally from 10 to 1000 nm. When an organic semiconductor film having a larger thickness than 1000 nm is formed, preferably, the molten compound (1) is used directly as it is.

<<Organic Semiconductor Device>>

The organic semiconductor device of the invention comprises an electrode and the above-mentioned organic semiconductor film of the invention.

The organic semiconductor device of the invention is excellent in lightweightness and flexibility, and as comprising the organic semiconductor film that contains the compound (1) or the compound (2), the device can be made to have desired properties by suitable molecular designing of the compound (1) or the compound (2).

Since the compound (1) or the compound (2) is visible light-transmissive, the organic semiconductor device of comprising these compound can be used under visible light.

Examples of the organic semiconductor device of the invention include a power amplification device and a signal control device, and as specific examples thereof, there may be mentioned a field effect transistor.

The field effect transistor of the invention comprises a gate electrode, a dielectric layer, a source electrode, a drain electrode and a semiconductor layer comprising the organic semiconductor film of the invention.

The field effect transistor in which the gate electrode, the dielectric layer, the source electrode and the drain electrode are formed of arbitrary materials and in which the semiconductor layer comprises the organic semiconductor film of the invention may be hereinafter referred to as "transistor of the invention".

The transistor in which the gate electrode, the dielectric layer, the source electrode, the drain electrode and the semiconductor layer are formed of arbitrary materials may be referred to as "arbitrary transistor".

In the transistor of the invention, the semiconductor layer comprises an organic semiconductor layer comprising the compound (1) or the compound (2); and since the compound (1) and the compound (2) therein have suitable electron mobility and hole mobility, the transistor can be a n-channel transistor or a p-channel transistor by controlling the voltage to be applied to the source electrode and the voltage to be applied to the gate electrode therein.

The gate electrode, the source electrode and the drain electrode may be formed of arbitrary materials, and preferably, these electrodes are formed of conductive materials. As the conductive materials, herein usable are metals or metal oxides as well as inorganic or organic semiconductors having an increased conductivity.

Examples of the metals include platinum, gold, silver, nickel, chromium, copper, iron, tin, antimonial lead, tantalum, indium, aluminium, zinc, magnesium and their alloys. Examples of the metal oxides include oxides of indium and tin, indium tin oxide(ITO).

Examples of the inorganic or organic semiconductors having an improved conductivity include silicon single-crystal, polysilicone, amorphous silicon, germanium, graphite, polyacetylene, polyparaphenylene, polythiophene, polypyrrole, polyaniline, polyethylenevinylene and polyparaphenylenevinylene.

Of the above, preferred as the electrode materials are those having a low electric resistance in the face thereof kept in contact with the adjacent organic semiconductor layer.

The dielectric layer may be formed of an arbitrary material, for which preferred is one having a high dielectric constant and having a low conductivity. Examples of the dielectric layer of the type include a layer formed of an inorganic oxide or nitride such as silicon oxide, silicon nitride, aluminum oxide, titanium oxide, and tantalum oxide; and a layer formed of polyacrylate, polymethacrylate, polyethylene terephthalate, polyimide, polyether, and siloxane-containing polymer. Of those, preferred are ones having a high effect of planarizing the surface of the layer.

The field effect transistor may be produced, for example, according to the method mentioned below.

First, a gate electrode is formed on a glass substrate or a polymer substrate. If desired, a dielectric layer may be laminated on the substrate having the gate electrode formed thereon. Onto this, a molten liquid of the compound (1), or a solution of the compound (1) dissolved in a solvent, or a molten liquid of the above-mentioned composition for organic semiconductor or a molten liquid of the above-mentioned liquid-crystal composition for organic semiconductor, or the above-mentioned composition for organic semiconductor or the above-mentioned liquid-crystal composition for organic semiconductor, or a solution of the above-mentioned composition for organic semiconductor dissolved in a solvent or a solution of the above-mentioned liquid-crystal composition for organic semiconductor dissolved in a solvent may be printed, or applied or dropped to thereby form a semiconductor layer thereon, and if desired, a dielectric layer may be formed on the semiconductor layer, and a source electrode and a drain electrode may be formed thereon.

The transistor of the invention may be used as a liquid-crystal display device or an electroluminescence (EL) device. In addition, since current to run between the source electrode and the drain electrode can be controlled by controlling the voltage to be applied to the gate electrode, the transistor can display gradations.

Another example of the organic semiconductor device of the invention is CMOS excellent in power efficiency.

Preferred embodiments of CMOS include:

(A) a semiconductor device comprising an n-channel transistor (1) and a p-channel transistor (2), wherein the n-channel transistor (1) is the transistor of the invention, the p-channel transistor (2) is an arbitrary transistor, the drain electrode of the n-channel transistor (1) and the drain electrode of the p-channel transistor (2) are connected to each other via a material having a transistor on-resistance of less than 10%, and the gate electrode of the n-channel transistor (1) and the gate electrode of the p-channel transistor (2) are connected to each other via a material having a transistor on-resistance of less than 10%; and (B) a semiconductor device comprising an n-channel transistor (3) and a p-channel transistor (4), wherein the n-channel transistor (3) is an arbitrary transistor, the p-channel transistor (4) is the transistor of the invention, the drain electrode of the n-channel transistor (3) and the drain electrode of the p-channel transistor (4) are connected to each other via a material having a transistor on-resistance of less than 10%, and the gate electrode of the n-channel transistor (3) and the gate electrode of the p-channel transistor (4) are connected to each other via a material having a transistor on-resistance of less than 10%.

An especially preferred CMOS is (C) a semiconductor device comprising the n-channel transistor (1) and the p-channel transistor (4), wherein the drain electrode of the n-channel transistor (1) and the drain electrode of the p-channel transistor (4) are connected to each other via a material having a transistor on-resistance of less than 10%, and the gate electrode of the n-channel transistor (1) and the gate electrode of the p-channel transistor (4) are connected to each other via a material having a transistor on-resistance of less than 10%. In the CMOS (C), the semiconductor layer of the n-channel transistor and that of the p-channel transistor may comprise a substantially same composition, and therefore the CMOS (C) can be produced at low cost with ease, can have a uniform carrier mobility as a whole and can be excellent in mechanical strength.

Not specifically defined, the material of which the transistor on-resistance is less than 10% includes gold, copper, metal aluminium, ITO, ZnO, etc.

In the organic semiconductor device of the invention, the organic semiconductor device of the type includes rectification devices, as well as thyristors, triacs, diacs and the like for switching operation. These may be obtained from the organic semiconductor film if necessary combined with any other semiconductive organic or inorganic material. Further, the organic semiconductor device of the invention is also usable as display devices, and in particular, can be favorably used as display devices in which all the parts are formed of organic compounds.

The display devices include, for example, flexible sheet-like display devices such as electronic papers, IC card tags, etc.; and liquid-crystal display devices. These display devices may be produced by forming the organic semiconductor film of the invention and at least one layer that comprises a constituent element to make the film function, on an insulating substrate formed of a flexible polymer. The display device produced according to the method is flexible and is therefore portable in pockets of clothes or in wallets, etc.

Also, An organic semiconductor device having flexibility can be applied to RFID (Radio Frequency Identification) tags. The RFID tags are formed on a reusable ticket or membership card, a means for payment settlement, an identification seal for baggage and commercial products, a paper acting as baggage tags or stamps, a paper used in company or government services, etc.

EXAMPLES

The invention is described more concretely with reference to the following Examples that are to demonstrate the possibility of producing the compound (1) or the compound (2) according to the above-mentioned scheme; however, the invention is not limited to these Examples.

[Method for Measurement of Phase Transition Point]

For identifying the phase and determining the phase transition temperature thereof, the compounds were analyzed according to the following methods 1) and 2).

1) Phase Identification:

A compound obtained in the following example was put on the hot plate (Mettler FP-52 hot stage) of a melting point measuring device equipped with a polarizing microscope, and heated thereon at a rate of 1° C./min. The exhibited phases were identified by the optical textures thereof observed through the polarizing microscope.

2) Phase Transition Temperature:

This was measured with Perkin Elmer scanning colorimeters, DSC-7 System and Diamond DSC System. The heating rate was 3° C./min.

hereinafter, crystal is represented by Cry. Distinguishable crystals are represented by $Cry_1$ or $Cry_2$. SmX represents a smectic X phase; SmA represents a smectic A phase. Liquid (isotropic) is represented by Iso. Regarding the expression of phase transition temperature, "Cry 133 SmX 308 Iso" means that the phase transition temperature from crystal to smectic X phase is 133° C., and the phase transition temperature from smectic X phase to liquid is 308° C. The same shall apply to the other expressions.

[Method of UV/Visible Absorption Spectrometry]

JASCO V-660 was used for absorption spectrometry. The compound obtained in Example mentioned below was dissolved in tetrahydrofuran (THF) to make a solution having a concentration of the compound of 20 μM solution. The solution put in a quartz cell having an optical path length of 10 mm, and analyzed.

[$^1$H-NMR Analysis]

A solution prepared by dissolving the compound (3) or the compound (4) obtained in Example 1 or 2, in $CDCl_3$ was analyzed at room temperature with a nuclear magnetic resonator DRX-500 (by Bruker Biospin). As the standard substance of which the δ value is point 0 (zero), used was tetramethylsilane (TMS).

Example 1

Synthesis of Compound (3)

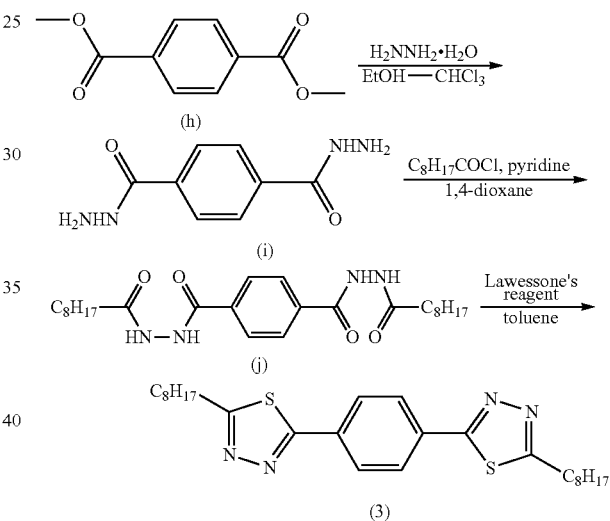

<First Step>

10 g (51.5 mmol) of dimethyl terephthalate (h) was dissolved in a mixed solvent of 15 mL of ethanol and 10 mL of chloroform, and 25.8 g (515 mmol) of hydrazine monohydrate was added thereto and heated under reflux for 4 hours. After cooled, the solid in the reaction solution was collected through filtration, and the residue was washed twice each with 10 mL of ethanol, and thereafter dried under reduced pressure to give 10 g of the compound (i).

<Second Step>

24.4 g (309 mmol) of pyridine was added to 10 g of the compound (i) dissolved in 200 mL of 1,4-dioxane in a nitrogen atmosphere, and subsequently, 21.8 g (123.6 mmol) of nonanoyl chloride was added thereto and stirred overnight. Afterwards, the reaction liquid was poured into water, the solid was collected through suction filtration, and the residue was washed a few times with distilled water, and then dried under reduced pressure to give 23.7 g of the compound (j).

<Third Step>

23.7 g of the compound (j) was dissolved in 300 mL of toluene, and 52.1 g (128.8 mmol) of Lawesson's reagent was added thereto and stirred under heat with reflux for 4 hours.

After cooled, the reaction solution was poured into 200 mL of aqueous 2 N sodium hydroxide solution, and stirred for 30 minutes. Subsequently, the solid was collected through suction filtration. The resulting solid was purified through silica gel column chromatography (eluent: chloroform/ethyl acetate=4/1 (v/v)), and recrystallized in a heptane/methanol mixed solvent to give 4.5 g of the compound (3) as a colorless crystal.

The $^1$H-NMR data of the obtained compound (3) are as follows:

$^1$H-NMR (CDCl$_3$): δ (ppm); 8.19 (s, 4H), 3.19 (t, 4H), 1.89 (quint, 4H), 1.48 (quint, 4H), 1.41-1.27 (m, 16H), 0.91 (t, 6H).

[Phase Transition Temperature (° C.)]
Cry$_1$ 86.7 Cry$_2$ 126.8 SmX 128.5 SmA 134.5 Iso
[Absorption Spectrum]
Visible light absorption was not detected.

Example 2

Synthesis of Compound (4)

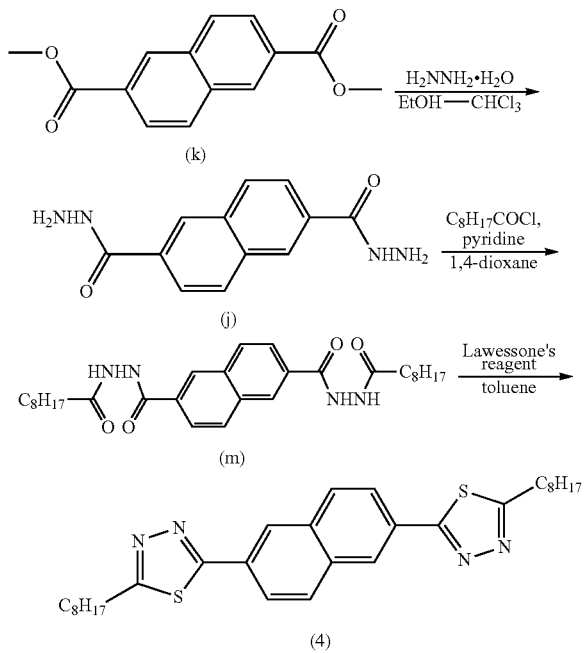

<First Step>
10 g (41 mmol) of dimethyl 2,6-naphthalenedicarboxylate (k) was dissolved in 15 mL of ethanol, and 22.3 g (446 mmol) of hydrazine monohydrate was added thereto and heated under reflux for 4 hours. After cooled, the solid in the reaction solution was collected through filtration, and the residue was washed twice each with 10 mL of ethanol, and thereafter dried under reduced pressure to give 6.01 g of the compound (1).

<Second Step>
11.7 g (147.6 mmol) of pyridine was added to 6.01 g of the compound (1) (24.6 mmol) dissolved in 150 mL of 1,4-dioxane in a nitrogen atmosphere, and subsequently, 10.4 g (59.0 mmol) of nonanoyl chloride was added thereto and stirred overnight. Afterwards, the reaction liquid was poured into water, the solid was collected through suction filtration, and the residue was washed a few times with distilled water, and then dried under reduced pressure to give 12.8 g of the compound (m).

<Third Step>
12.8 g of the compound (m) (24.4 mmol) was dissolved in 300 mL of toluene, and 25.0 g (62.0 mmol) of Lawesson's reagent was added thereto and stirred under heat with reflux for 4 hours. After cooled, the reaction solution was poured into 200 mL of aqueous 2 N sodium hydroxide solution, and stirred for 30 minutes. Subsequently, the solid was collected through suction filtration. The resulting solid was purified through silica gel column chromatography (eluent: chloroform/ethyl acetate=9/1 (v/v)), and recrystallized in a heptane/methanol mixed solvent to give 7.6 g of the compound (4) as a colorless crystal.

The $^1$H-NMR data of the obtained compound (4) are as follows:

$^1$H-NMR (CDCl$_3$): δ (ppm); 8.40 (s, 2H), 8.17 (dd, 2H), 8.02 (d, 2H), 3.19 (t, 4H), 1.89 (quint, 4H), 1.48 (quint, 4H), 1.41-1.27 (m, 16H), 0.91 (t, 6H).

[Phase Transition Temperature (° C.)]
Cry 123.1 SmX 136.9 SmA 222.5 Iso
[Absorption Spectrum]
Visible light absorption was not detected.

Example 3

Measurement of Carrier Mobility (electron mobility, hole mobility) of Compound (3):

The carrier mobility of the compound (3) synthesized in Example 1 was measured according to a time-of-flight method (TOF method). FIG. 1 shows a schematic outline view of the cell used in the measurement method.

First, a spacer was sprayed on the electrode surface of a glass substrate 1 with an indium tin oxide (ITO) electrode 2 fitted thereon. A glass substrate 4 with an ITO electrode 5 was stuck thereto via the spacer in such a manner that the ITO electrode 5 could face the spacer, thereby preparing a TOF method sample cell.

The prepared cell was heated to 150° C., and a crystal of the compound (3) was inserted into the space between the two substrates, where the compound (3) melted and rapidly diffused between the ITO electrodes owing to the capillary phenomenon thereof. When the cell was got back to room temperature, then the compound (3) solidified inside the cell.

Measurement of carrier mobility carried out according to the following procedure. The ITO electrode 2 and the ITO electrode 5 were connected to each other via a lead wire, and the lead wire-fitted cell was set on a temperature-variable hot stage. A voltage was applied to the cell, and the compound (3) was irradiated with a nanosecond pulse of a nitrogen laser (wavelength: 337 nm), where the time-dependent current change was determined with an oscilloscope.

Compute of carrier mobility carried out according to the following procedure. According to the method of Harvey Scher and Elliott W. Montroll, Phys. Rev. B, 12, 2455 (1975), the time (t) taken by the carrier to run from the neighborhood electrode irradiated with the laser pulse to reach the counter electrode was obtained from the time-dependent current change wave. From the time (t) taken for the carrier to reach the counter electrode after the application of laser pulse light, the applied voltage and the electrode-to-electrode distance, the carrier mobility was computed.

The carrier mobility at 55° C. of the compound (3) exhibiting a Cry$_1$ phase was measured at an electrode-to-electrode distance of 16.5 The hole mobility was $3.5 \times 10^{-4}$ cm$^2$/Vs within an applied voltage range of from 50 V to 83 V. The electron mobility was $9.0 \times 10^{-4}$ cm$^2$/Vs within the applied voltage range of from 50 V to 83 V.

Example 4

Measurement of Carrier Mobility of Compound (4)

According to the same method as in Example 3 but using the compound (4) synthesized in Example 2, a TOF method sample cell was prepared. The cell was heated at a temperature of 250° C.

The carrier mobility at 90° C. of the compound (4) exhibiting a Cry phase was measured at an electrode-to-electrode distance of 19.54 μm. The hole mobility was $1.0 \times 10^{-1}$ cm$^2$/Vs within an applied voltage range of from 15 V to 30 V. The electron mobility was $1.2 \times 10^{-1}$ cm$^2$/Vs within the applied voltage range of from 15 V to 30 V.

Comparative Example 1

The compounds 5a to 5c in JP 2009-242339 A, which has a description of absorption spectra and has a description of transmission of both holes and electrons, and the compound (4) synthesized in Example 2 were compared in point of the physical properties thereof. As a result, the carrier mobility of the comparative compounds was on the lowered level of $10^{-3}$ cm$^2$/Vs as that of the compound (4). The comparative compounds had a large absorption corresponding to a molar absorption coefficient of $10^5$ M$^{-1}$cm$^{-1}$ at around 600 nm. Not having the absorption in range of visible light, the compound (4) is advantageous in application to display devices for use under visible light. In addition, the compound (4) is visible light-transmissive, and therefore can be used in various applications with no limitation. In view of these points, the compound (4) is excellent.

Comparative Example 2

The Nonpatent Reference 1 describes a 2,7-bis(4-tert-butylphenyl-9,9'-spirobifluorene (the following No. 243) as compound that have not absorb visible light that may be transmission of both holes and electrons. In addition, the result that measured the carrier mobility of No. 243 compound is described in non-patent document 1 by using the TOF method to the same method as in Example 4. In the result, electron mobility and a hole mobility indicated both slightly above $1 \times 10^{-3}$ cm$^2$/Vs at 60° C. The electron mobility of the compound (4) is bigger about 10 times than electron mobility of No. 243 compound. In addition, the hole mobility of the compound (4) is bigger about 100 times than hole mobility of No. 243 compound. In this respect, the compound (4) is superior to No. 243 compound.

(No. 243)

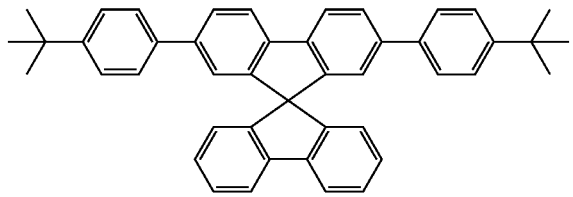

What is claimed is:

1. A compound represented by a formula (1):

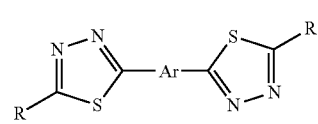

wherein,

R independently represents hydrogen, or alkyl having from 1 to 24 carbon atoms, and any —CH$_2$— in the alkyl may be replaced by —O—, —S—, —CO— or —SiH$_2$—, any —(CH$_2$)$_2$— may be replaced by —CH=CH— or —C≡C—, and any hydrogen may be replaced by halogen;

Ar represents naphthylene, anthrylene, phenanthrylene, or phenylene; and every hydrogen in phenylene is replaced by halogen, and any hydrogen in naphthylene, anthrylene and phenanthrylene may be replaced by halogen.

2. The compound as claimed in claim 1, wherein in the formula (1), R is independently hydrogen, alkyl having from 1 to 20 carbon atoms, alkoxy having from 1 to 20 carbon atoms, alkenyl having from 2 to 20 carbon atoms, alkynyl having from 2 to 20 carbon atoms, alkoxyalkyl having from 2 to 20 carbon atoms, alkenyloxy having from 2 to 20 carbon atoms, thioalkyl having from 1 to 20 carbon atoms, alkylthioalkyl having from 2 to 20 carbon atoms, or thioalkenyl having from 2 to 20 carbon atoms, and any hydrogen in these groups may be replaced by fluorine.

3. The compound as claimed in claim 1, wherein in the formula (1), Ar is naphthylene, anthrylene, phenanthrylene, or phenylene; and every hydrogen in phenylene is replaced by chlorine or fluorine, and any hydrogen in naphthylene, anthrylene and phenanthrylene may be replaced by fluorine.

4. The compound as claimed in claim 1, which has an electron mobility and a hole mobility of from $1.0 \times 10^{-4}$ to $1.0 \times 10^2$ cm$^2$/Vs.

5. A composition for organic semiconductor, which comprises a compound represented by a formula (2):

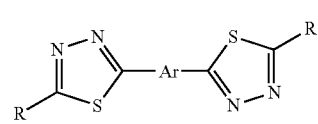

wherein,

R independently represents hydrogen, or alkyl having from 1 to 24 carbon atoms, and any —CH$_2$— in the alkyl may be replaced by —O—, —S—, —CO— or —SiH$_2$—, any —(CH$_2$)$_2$— may be replaced by —CH=CH— or —C≡C— and any hydrogen may be replaced by halogen;

Ar represents phenylene, naphthylene, anthrylene, or phenanthrylene; and every hydrogen in phenylene is replaced by halogen, and any hydrogen in naphthylene, anthrylene and phenanthrylene may be replaced by halogen.

6. The composition for organic semiconductor as claimed in claim 5, wherein in the formula (2), R is independently hydrogen, alkyl having from 1 to 20 carbon atoms, alkoxy having from 1 to 20 carbon atoms, alkenyl having from 2 to 20 carbon atoms, alkynyl having from 2 to 20 carbon atoms, alkoxyalkyl having from 2 to 20 carbon atoms, alkenyloxy having from 2 to 20 carbon atoms, thioalkyl having from 1 to 20 carbon atoms, alkylthioalkyl having from 2 to 20 carbon atoms, or thioalkenyl having from 2 to 20 carbon atoms, and any hydrogen in these groups may be replaced by fluorine.

7. The composition for organic semiconductor as claimed in claim 5, wherein in the formula (2), Ar is phenylene, naphthylene, anthrylene, or phenanthrylene; and every hydrogen in phenylene is replaced by fluorine, and any hydrogen in naphthylene, anthrylene, or phenanthrylene may be replaced by fluorine.

8. A liquid-crystal composition for organic semiconductor wherein the composition for organic semiconductor of claim 5 has a smectic phase or a nematic phase.

9. An organic semiconductor film formed of the composition for organic semiconductor of claim 5.

10. An organic semiconductor device comprising an electrode and the organic semiconductor film of claim 9.

11. A field effect transistor comprising a gate electrode, a dielectric layer, a source electrode, a drain electrode and a semiconductor layer, wherein the semiconductor layer comprises the organic semiconductor film of claim 9.

12. A semiconductor device comprising an n-channel transistor (1) and a p-channel transistor (2),
wherein the n-channel transistor (1) is the transistor of claim 11,
the p-channel transistor (2) is formed of an arbitrary material,
the drain electrode of the n-channel transistor (1) and the drain electrode of the p-channel transistor (2) are connected to each other via a material having a transistor on-resistance of less than 10%, and the gate electrode of the n-channel transistor (1) and the gate electrode of the p-channel transistor (2) are connected to each other via a material having a transistor on-resistance of less than 10%.

13. A semiconductor device comprising an n-channel transistor (3) and a p-channel transistor (4),
wherein the n-channel transistor (3) is formed of an arbitrary material,
the p-channel transistor (4) is the transistor of claim 11,
the drain electrode of the n-channel transistor (3) and the drain electrode of the p-channel transistor (4) are connected to each other via a material having a transistor on-resistance of less than 10%, and the gate electrode of the n-channel transistor (3) and the gate electrode of the p-channel transistor (4) are connected to each other via a material having a transistor on-resistance of less than 10%.

14. A semiconductor device comprising an n-channel transistor (1) and a p-channel transistor (4),
wherein the n-channel transistor (1) and the p-channel transistor (4) each are the transistor of claim 11,
the drain electrode of the n-channel transistor (1) and the drain electrode of the p-channel transistor (4) are connected to each other via a material having a transistor on-resistance of less than 10%, and the gate electrode of the n-channel transistor (1) and the gate electrode of the p-channel transistor (4) are connected to each other via a material having a transistor on-resistance of less than 10%.

15. An organic semiconductor film formed of the compound of claim 1.

16. An organic semiconductor film formed of the liquid-crystal composition for organic semiconductor of claim 8.

17. An organic semiconductor device comprising an electrode and the organic semiconductor film of claim 15.

18. An organic semiconductor device comprising an electrode and the organic semiconductor film of claim 16.

* * * * *